US011332756B2

(12) United States Patent
Balachandran et al.

(10) Patent No.: US 11,332,756 B2
(45) Date of Patent: May 17, 2022

(54) RNA VIRUS VECTORS CARRYING DAI AND RIPK3

(71) Applicant: Institute For Cancer Research, Philadelphia, PA (US)

(72) Inventors: Siddharth Balachandran, Philadelphia, PA (US); Roshan Thapa, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 254 days.

(21) Appl. No.: 16/315,420

(22) PCT Filed: Jul. 5, 2017

(86) PCT No.: PCT/US2017/040719
§ 371 (c)(1),
(2) Date: Jan. 4, 2019

(87) PCT Pub. No.: WO2018/009541
PCT Pub. Date: Jan. 11, 2018

(65) Prior Publication Data
US 2019/0211359 A1  Jul. 11, 2019

Related U.S. Application Data

(60) Provisional application No. 62/359,465, filed on Jul. 7, 2016.

(51) Int. Cl.
| *C12N 15/79* | (2006.01) |
| *C07H 21/04* | (2006.01) |
| *C12N 15/86* | (2006.01) |
| *A61P 37/04* | (2006.01) |
| *A61K 39/39* | (2006.01) |
| *C07K 14/47* | (2006.01) |
| *C12N 9/12* | (2006.01) |
| *A61K 39/00* | (2006.01) |

(52) U.S. Cl.
CPC .............. *C12N 15/86* (2013.01); *A61K 39/39* (2013.01); *A61P 37/04* (2018.01); *C07K 14/47* (2013.01); *C07K 14/4705* (2013.01); *C12N 9/12* (2013.01); *C12Y 207/11001* (2013.01); *A61K 2039/585* (2013.01); *C12N 2760/16121* (2013.01); *C12N 2760/16132* (2013.01); *C12N 2760/16143* (2013.01)

(58) Field of Classification Search
CPC .......... C12N 15/86; C12N 2760/16143; C07H 21/02; C07H 21/04
See application file for complete search history.

(56) References Cited

U.S. PATENT DOCUMENTS

| 2014/0314739 A1 | 10/2014 | Petrovsky |
| 2016/0160189 A1 | 6/2016 | Green et al. |

OTHER PUBLICATIONS

Petrovsky, Nikolai, 2014, US 20140314739 A1.*
Green et al., Jun. 9, 2016, US 20160160189 A1.*
Yang et al., 2005, GenEmbl Accession No. AY453693, computer printout, pp. 9-11.*
Pham et al., 2013, Journal of Virology, vol. 87, No. 6, p. 3076-3086.*
Elias, Jack, 2011, US 20110245323 A1.*
Yang et al., 2015, GenEmbl Accession No. KJ899663, computer printout, pp. 1-4.*
Green et al., 2014, GeneSeq Accession No. BBP87827, computer printout, pp. 1-3.*
Chen et al., "DNA-depending activator of interferon-regulatory factors inhibits hepatitis B virus replication", World J Gastroenterol, 2012, 18(22):2850-2858.
European Search Report dated Nov. 22, 2019 for corresponding International Patent Application No. PCT/US2017/040719.
Moriwaki et al., "Necroptosis-independent signaling by the RIP kinases in inflammation", Cell Mol Life Sci, 2016, 73, pp. 2325-2334.
Vanden Berghe et al., "An outline of necrosome triggers", Cell Mol Life Sci, 2016, 73, pp. 2137-2152.
Vince et al., "The intersection of cell death and inflammasome activation", Cell Mol Life Sci, 2016, 73, pp. 2349-2367.

* cited by examiner

*Primary Examiner* — Shin Lin Chen
(74) *Attorney, Agent, or Firm* — Stradley Ronon Stevens & Young, LLP

(57) ABSTRACT

RNA virus vectors comprising a gene encoding the DNA-dependent activator of interferon-regulatory factors (DAI) protein, and optionally further comprising a gene encoding the receptor-interacting serine/threonine-protein kinase 3 (RIPK3) may be used therapeutically to induce cell death, as well as an inflammatory immune response, against tumors and virally-infected cells.

5 Claims, 41 Drawing Sheets
Specification includes a Sequence Listing.

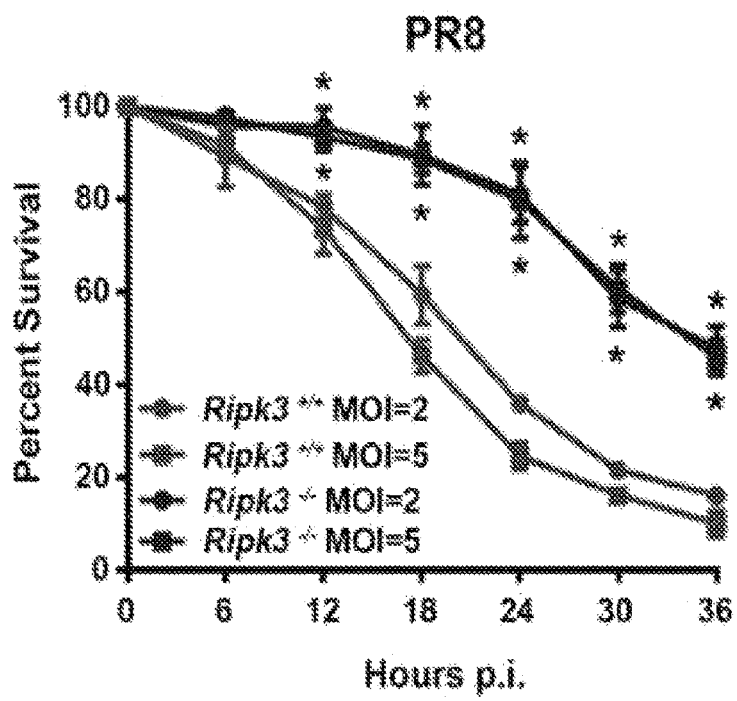
Figure 1E
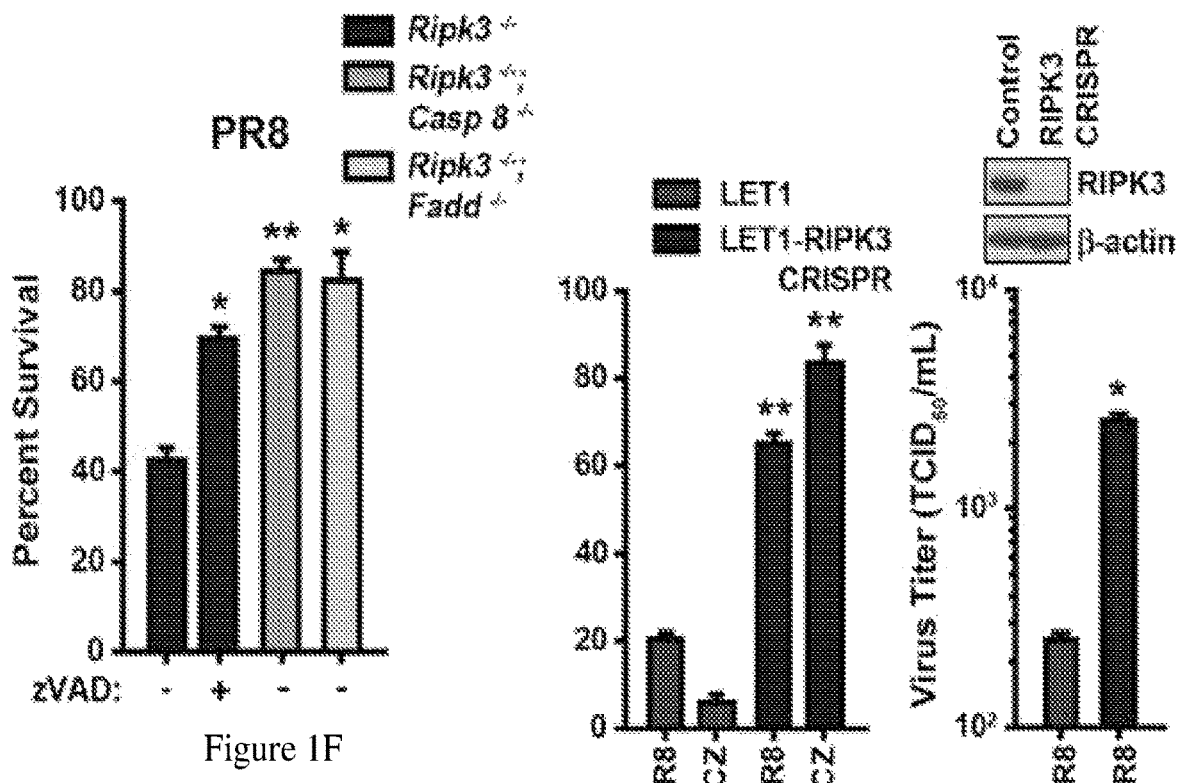
Figure 1F
Figure 1G

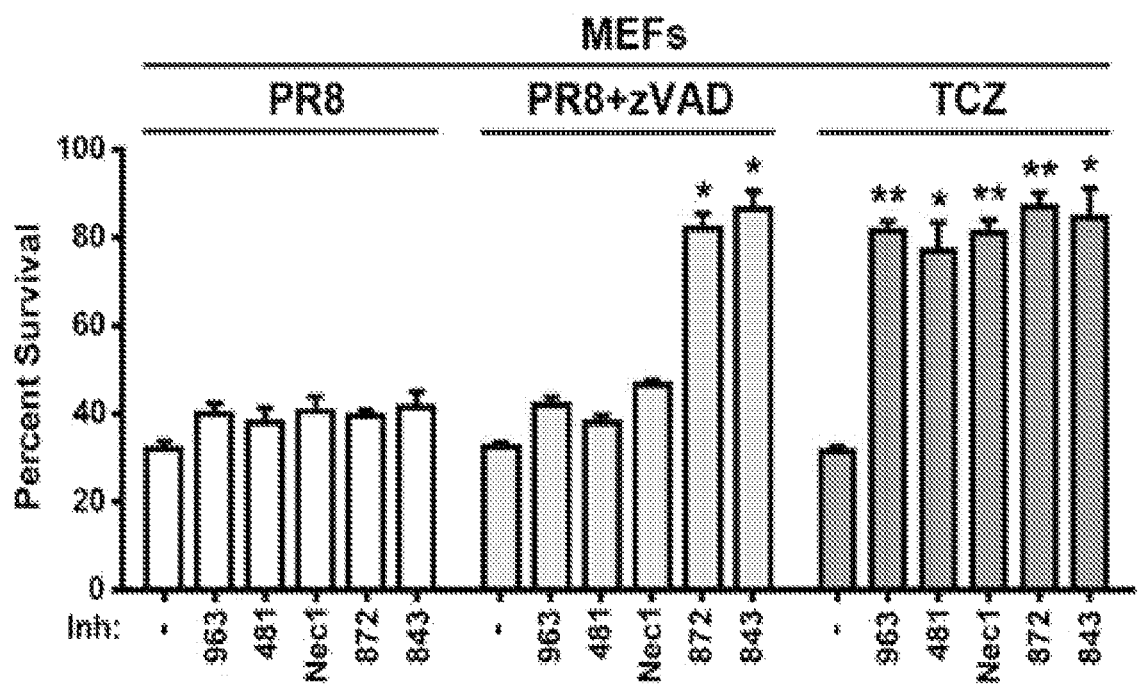
Figure 5A
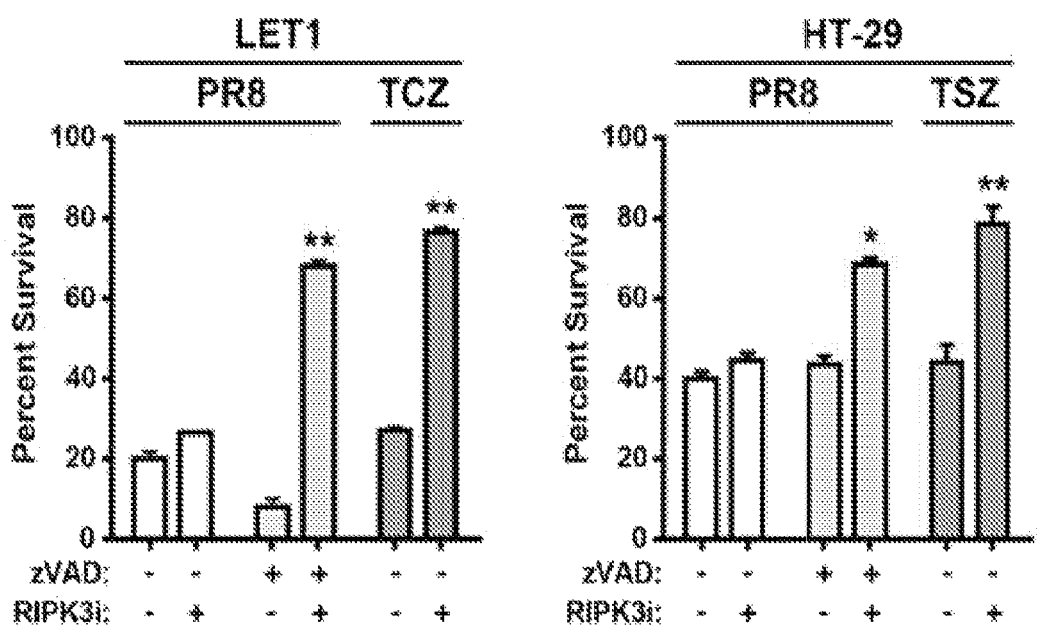
Figure 5B
Figure 5C

SEQUENCE LISTING

<160> NUMBER OF SEQ ID NOS: 21

<210> SEQ ID NO 1
<211> LENGTH: 1297
<212> TYPE: DNA
<213> ORGANISM: Artificial Sequence
<220> FEATURE:
<223> OTHER INFORMATION: ZBP1 (DAI) cDNA

<400> SEQUENCE: 1

```
agagctgcaa gaagcaccag gctcggccac ttcagaagcc ccagcctcga cctagcccac      60
cctctcaggg ccacagtgca gaagcctgca cacctgccaa gtctctccga ctccttgcag     120
ctgctgtcag catggcccag gctcctgctg acccgggcag agaaggccac cttgaacaaa     180
gaatcctgca ggtgctgaca gaggctggct ccccggtgaa acttgcccag ctggtgaagg     240
aatgccaagc acccaagagg gagctcaacc aagtcctcta ccgaatgaaa aaggagttga     300
aagtctccct cacatcccct gccacctggt gcttgggcgg gactgatcct gaaggcgagg     360
gtcctgcaga gctggccttg tccagccctg ccgagaggcc ccagcaacat gcagctacaa     420
ttccagagac ccctggccct cagttcagcc aacaacggga ggaagacatc tacaggtttc     480
tcaaagacaa tggtccccag agggccctgg tcatcgccca agcactggga atgaggacag     540
caaaagatgt gaaccgagac ttgtacagga tgaagagcag gcaccttctg acatggatg      600 agcagtccaa agcatggacg atttaccgcc cagaagattc tggaagaaga gcaaagtcag     660
cctcaattat ttaccagcac aatccaatca acatgatctg ccagaatgga cccaacagct     720
ggatttccat tgcaaactcc gaagccatcc agattggaca cgggaacatc attacaagac     780
agacagtctc cagggaggac ggttccgccg gtccacgcca cctcccttca atggcaccag     840
gtgattcctc aacttggggg accctagttg atccctgggg ccccaggac atccacatgg      900 agcagtccat actgagacgg gtgcagctgg gacacagcaa tgagatgagg ctccacggcg     960
tcccgtccga gggccctgcc cacatcccc ctggcagccc cccagtgttc cagtgcagtg     1020
ggaagcaggc agcagaggag agaggagctg aatcccagag gaagacactg acgtccagat    1080
cagccgggcg ggatcagtgg ggcagaccca ctgcgggatc agtggagcag aaagacgctt    1140
cccagacagc acaacagcac gagcggagtc tctgccactg ctgccggccc agaagcttcg    1200
tttgaagcaa gaattcccag tccaggaact cacccctgagg gggaagccgc ccagagaatc    1260
cacatgaaat cgtgctttct cgaggacgcc accatcg                              1297
```

<210> SEQ ID NO 2
<211> LENGTH: 1557
<212> TYPE: DNA
<213> ORGANISM: Artificial Sequence
<220> FEATURE:
<223> OTHER INFORMATION: RIPK3 cDNA

<400> SEQUENCE: 2

| | | |
|---|---|---|
| atgtcgtgcg tcaagttatg gcccagcggt gcccccgccc ccttggtgtc catcgaggaa | 60 |
| ctggagaacc aggagctcgt cggcaaaggc gggttcggca cagtgttccg ggcgcaacat | 120 |
| aggaagtggg gctacgatgt ggcggtcaag atcgtaaact caaaggcgat atccagggag | 180 |
| gtcaaggcca tggcaagtct ggataacgaa ttcgtgctgc gcctagaagg ggttatcgag | 240 |
| aaggtgaact gggaccaaga tcccaagccg gctctggtga ctaaattcat ggagaacggc | 300 |
| tccttgtcgg ggctgctgca gtcccagtgc cctcggccct ggccgctcct tgccgcctg | 360 |
| ctgaaagaag tggtgcttgg gatgttttac ctgcacgacc agaacccggt gctcctgcac | 420 |
| cgggacctca agccatccaa cgtcctgctg acccagagc tgcacgtcaa gctggcagat | 480 |
| tttggcctgt ccacatttca ggaggctca cagtcaggga cagggtccgg ggagccaggg | 540 |
| ggcaccctgg gctacttggc cccagaactg tttgttaacg taaaccggaa ggcctccaca | 600 |
| gccagtgacg tctacagctt cgggatccta atgtgggcag tgcttgctgg aagagaagtt | 660 |
| gagttgccaa ccgaaccatc actcgtgtac gaagcagtgt gcaacaggca gaaccggcct | 720 |
| tcattggctg agctgcccca gccgggcct gagactcccg gcttagaagg actgaaggag | 780 |
| ctaatgcagc tctgctggag cagtgagccc aaggacagac cctccttcca ggaatgccta | 840 |
| ccaaaaactg atgaagtctt ccagatggtg gagaacaata tgaatgctgc tgtctccacg | 900 |
| gtaaaggatt tcctgtctca gctcaggagc agcaatagga gattttctat cccagagtca | 960 |
| ggccaaggag ggacagaaat ggatggcttt aggagaacca tagaaaacca gcactctcgt | 1020 |
| aatgatgtca tggtttctga gtggctaaac aaactgaatc tagaggagcc tcccagctct | 1080 |
| gttcctaaaa aatgcccgag ccttaccaag aggagcaggg cacaagagga gcaggttcca | 1140 |
| caagcctgga cagcaggcac atcttcagat tcgatggccc aacctcccca gactccagag | 1200 |
| acctcaactt tcagaaacca gatgccagc cctacctcaa ctggaacacc aagtcctgga | 1260 |
| ccccgaggga tcaggggggc tgagagacaa ggcatgaact ggtcctgcag gaccccggag | 1320 |
| ccaaatccag taacagggcg accgctcgtt aacatataca actgctctgg ggtgcaagtt | 1380 |
| ggagacaaca actacttgac tatgcaacag acaactgcct tgcccacatg gggcttggca | 1440 |
| ccttcgggca aggggagggg cttgcagcac cccccaccag taggttcgca agaaggccct | 1500 |
| aaagatcctg aagcctggag caggccacag ggttggtata atcatagcgg gaaataa | 1557 |

<210> SEQ ID NO 3
<211> LENGTH: 1682
<212> TYPE: DNA
<213> ORGANISM: Artificial Sequence
<220> FEATURE:
<223> OTHER INFORMATION: MLKL cDNA

<400> SEQUENCE: 3

| | | |
|---|---|---|
| atccagcaca gagaagcaaa caccagaagc ttctctccaa ctttcagttt ttctctaaac | 60 |
| ttccagtcct tctcatactg tgtcctggtt ataatagttg ctgggacctt attctattct | 120 |
| gaatccccag cccctaaaga aggcttggta ctgacgtgta cagcgtagtt acccagtgac | 180 |

| | |
|---|---|
| tttggggaag gcaggaagag tgtggaaagg acaggaggaa ggaagggagg ggccgtggct | 240 |
| ccgagctgcc tagaaagcgg ctccaggag ccagggcacc gtgagcctgg tggttggcag | 300 |
| ctggagccac gtcggagggg gaagtgtcgc agcattctct gcaggcatca cagacctgag | 360 |
| gcagtggcct ccggagggca ctggacagaa acagccatcc aagtggctga gtggagggac | 420 |
| cctgctcaag tgcagctgca gtggccgggg tttccctcag gtagggatcg ggcgccttg | 480 |
| tcgccgccag ccacgtgtgg cgtccggtac agtcagcaga gtgcagggtg cgggcaccag | 540 |
| gaaaggggc gcagggaac tcccgcgggc ctcgcgtttg caaacttctc gcctgggcag | 600 |
| gaggcggtcg tgggaaagaa ggtggaagag cgagcttttt ggaactgtgc acggacaga | 660 |
| ttggacgcac acccctcggg aggcgcgaag gcatggaaaa tttgaagcat attatcaccc | 720 |
| ttggccaggt catccacaaa cggtgtgaag agatgaaata ctgcaagaaa cagtgccggc | 780 |
| gcctgggcca ccgcgtcctc ggcctgatca agcctctgga gatgctccag gaccaaggaa | 840 |
| agaggagcgt gccctctgag aagttaacca cagccatgaa ccgcttcaag gctgccctgg | 900 |
| aggaggctaa tggggagata gaaaagttca gcaatagatc caatatctgc aggtttctaa | 960 |
| cagcaagcca ggacaaaata ctcttcaagg acgtgaacag gaagctgagt gatgtctgga | 1020 |
| aggagctctc gctgttactt caggttgagc aacgcatgcc tgtttcaccc ataagccaag | 1080 |
| gagcgtcctg ggcacaggaa gatcagcagg atgcagacga agacaggcga gctttccaga | 1140 |
| tgctaagaag agataatgaa aaatagaag cttcactgag acgattagaa atcaacatga | 1200 |
| aagaaatcaa ggaaactttg aggcagtatt taccaccaaa atgcatgcag gagatcccgc | 1260 |
| aagagcaaat caaggagatc aagaaggagc agctttcagg atccccgtgg attctgctaa | 1320 |
| gggaaaatga agtcagcaca cttatataag gagaatacca cagagctcca gtggccataa | 1380 |
| aagtattcaa aaaactccag gctggcagca ttgcaatagt gaggcagact ttcaataagg | 1440 |
| agatcaaaac catgaagaaa ttcgaatctc ccaacatcct gcgtatattt gggatttgca | 1500 |
| ttgatgaaac aggctacacc attcagaagc acctgaactc cacggaaaaa tcagaagctc | 1560 |
| aaacttcctg gtaactcaag gctaccaagt gaagatttgg gtacctggct gagtttgggg | 1620 |
| ctggcagcct tcagcacacc aatggtgtca atggcaggtg tgcatgggac aagaacatat | 1680 |
| gc | 1682 |

<210> SEQ ID NO 4
<211> LENGTH: 1295
<212> TYPE: RNA
<213> ORGANISM: Artificial Sequence
<220> FEATURE:
<223> OTHER INFORMATION: ZBP1 (DAI) RNA

<400> SEQUENCE: 4

| | |
|---|---|
| agagcugcaa gaagcaccag gcucggccac uucagaagcc ccagccucga ccuagcccac | 60 |
| ccucucaggg ccacagugca gaagccugca caccugccaa gucucuccga cuccuugcag | 120 |
| cugcugucag cauggcccag gcuccugcug cccgggcaga gaaggccacc uugaacaaag | 180 |
| aauccugcag gugcugacag aggcuggcuc cccggugaaa cuugcccagu ggugaaggaa | 240 |
| ugccaagcac ccaagaggga gcucaaccaa gucccucuacc gaaugaaaaa ggaguugaaa | 300 |
| gucucccuca caucccugc caccuggugc uugggcggga cugauccuga aggcgagggu | 360 |
| ccugcagagc uggccuuguc cagcccugcc gagaggcccc agcaacaugc agcuacaauu | 420 |
| ccagagaccc cuggcccuca guucagccaa caacgggagg aagacaucua caggutuucuc | 480 |
| aaagacaaug ucccccagag ggcccuggue aucgcccaag cacuggaau gaggacagca | 540 |

```
aaagauguga accgagacuu guacaggaug aagagcaggc accuucugga cauggaugag    600
caguccaaag cauggacgau uuaccgccca gaagauucug gaagaagagc aaagucagcc    660
ucaauuauuu accagcacaa uccaaucaac augaucugcc agaauggacc caacagcugg    720
auuuccauug caaacuccga agccauccag auuggacacg ggaacaucau acaagacag     780 acagucucca gggaggacgg uuccgccggu ccacgccacc ucccuucaau ggcaccaggu    840
gauuccucaa cuuggggggac ccuaguugau cccuggggc cccaggacau ccacauggag    900
caguccauac ugagacgggu gcagcuggga cacagcaaug agaugaggcu ccacggcguc    960
ccguccgagg gcccugccca caucccccccu ggcagccccc cagucuuccca gugcaguggg    1020 aagcaggcag cagaggagag aggagcugaa ucccagagga agacacugac guccagauca    1080
gccgggcggg aucaguggg cagacccacu gcgggaucag uggagcagaa agacgcuucc     1140
cagacagcac aacagcacga gcggagucuc ugccacugcu gccggcccag aagcuucguu    1200
ugaagcaaga auucccaguc caggaacuca cccugagggg gaagccgccc agagaaucca    1260
caugaaaucg ugcuuucucg aggacgccac caucg                              1295

<210> SEQ ID NO 5
<211> LENGTH: 1557
<212> TYPE: RNA
<213> ORGANISM: Artificial Sequence
<220> FEATURE:
<223> OTHER INFORMATION: RIPK3 RNA

<400> SEQUENCE: 5
augucgugcg ucaaguuaug gcccagcggu gcccccgccc ccuuggugguc caucgaggaa    60 cuggagaacc aggagcucgu cggcaaaggc ggguucggca caguuuccg ggcgcaacau      120 aggaaguggg gcuacgaugu ggcggucaag aucguaaacu caaaggcgau uccaggggag    180
gucaaggcca uggcaagucu ggauaacgaa uucgugcugc gccuagaagg gguuaucgag    240
aaggugaacu gggaccaaga ucccaagccg gcucuggugga cuaaauucau ggagaacggc    300
uccuugucgg ggcugcugca gucccagugc cucggcccu ggccgcuccu uugccgccug      360
cugaaagaag uggugcuugg gauguuuuac cugcacgacc agaacccggu gccucugcac    420
cgggaccuca agccauccaa cguccugcug gacccagagc ugcacgucaa gcuggcagau    480
uuuggccugu ccacauuuca gggaggcuca cagucaggga caggguccgg ggagccaggg    540
ggcacccugg gcuacuuggc cccagaacug uuuguuaacg uaaaccggaa ggccuccaca    600
gccagugacg ucuacagcuu cgggauccua augggugcag ugcuugcugg aagagaaguu    660
gaguugccaa ccgaaccauc acucguguac gaagcagugu gcaacaggca gaaccggccu    720 ucauggcug agcugcccca agccgggccu gagacucccg gcuuagaagg acugaaggag    780
cuaaugcagc ucugcuggag cagugagccc aaggacagac ccuccuuccca ggaaugccua    840 ccaaaaacug augaagucuu ccagauggug gagaacaaua ugaaugcgcgc ugucuccacg    900 guaaaggauu uccuguccua gcucaggagc agcaauagga gauuucuau cccagaguca     960 ggccaaggag ggacagaaau ggauggcuuu aggagaacca uagaaaacca gcacucucgu    1020
aaugauguca ugguuucuga guggcuaaac aaacugaauc uagaggagcc ucccagcucu    1080
guuccuaaaa aaugcccgag ccuuaccaag aggagcaggg cacaagagga gcagguucca    1140
caagccugga cagcaggcac aucuucagau ucgauggccc aaccuccccca gacuccagag    1200 accucaacuu ucagaaaacca gaugcccagc ccuaccucaa cuggaacacc aagcccugga    1260
```

| | | |
|---|---|---|
| ccccgaggga aucaggggc ugagagacaa ggcaugaacu gguccugcag gaccccggag | 1320 | |
| ccaaauccag uaacagggcg accgcucguu aacauauaca acugcucugg ggugcaaguu | 1380 | |
| ggagacaaca acuacuugac uaugcaacag acaacugccu ugcccacaug gggcuuggca | 1440 | |
| ccuucgggca aggggagggg cuugcagcac ccccaccag uagguucgca agaaggcccu | 1500 | |
| aaagauccug aagccuggag caggccacag gguuggauaua aucauagcgg gaaauaa | 1557 | |

<210> SEQ ID NO 6
<211> LENGTH: 1682
<212> TYPE: RNA
<213> ORGANISM: Artificial Sequence
<220> FEATURE:
<223> OTHER INFORMATION: MLKL RNA

<400> SEQUENCE: 6

| | |
|---|---|
| auccagcaca gagaagcaaa caccagaagc uucucuccaa cuuucaguuu uucucuaaac | 60 |
| uuccaguccu ucucauacug uguccugguu auaauaguug cuggaccuu auucuauucu | 120 |
| gaaucccag ccccuaaaga aggcuuggua cugacguguaa cagcguaguu acccagugac | 180 |
| uuuggggaag gcaggaagag uguggaaagg acaggaggaa ggaagggagg ggccguggcu | 240 |
| ccgagcugcc uagaaagcgg cuccaggag ccagggcacc gugagccugg gguugggcag | 300 |
| cuggagccac gucggagggg gaagucgc agcauucucu gcaggcauca cagaccugag | 360 |
| gcaguggccu ccggagggca cuggacagaa acagccaucc aaguggcuga guggagggac | 420 |
| ccugcucaag ugcagcugca guggccgggg uuccccucag uagggaucg gggcgccuug | 480 |
| ucgccgccca ccacgugugg cguccggac agucagcaga gugcagggug cgggcaccag | 540 |
| gaaaggggc gcaggggaac ucccgcgggc cucgcguuug caaacuucuc gccugggcag | 600 |
| gaggcggucg ugggaaagaa ggugggaagag cgagcuuuuu ggaacugugc acggacagaa | 660 |
| uuggacgcac accccucggg aggcgcgaag gcauggaaaa uuugaagcau auuaucaccc | 720 |
| uuggccaggu cauccacaaa cggugugaag agaugaaaua cugcaagaaa cagugccggc | 780 |
| gccugggcca ccgcguccuc ggccugauca agccucugga gaugcuccag gaccaaggaa | 840 |
| agaggagcgu gcccucugag aaguuaacca cagccaugaa ccgcuucaag gcugcccugg | 900 |
| aggaggcuaa uggggagaua gaaaaguuca gcaauagauc caauaucugc agguuucuaa | 960 |
| cagcaagcca ggacaaaaua cucuucaagg acguaacag gaagcugagu gaugucugga | 1020 |
| aggagcucuc gcuguuacuu cagguugagc aacgcaugcc uguuucaccc auaagccaag | 1080 |
| gagcguccug ggcacaggaa gaucagcagg augcagacga agacaggcga gcuuccaga | 1140 |
| ugcuaagaag agauaaugaa aaauagaag cuucacugag acgauuagaa aucaacauga | 1200 |
| aagaaaucaa ggaaacuuug aggcaguauu uaccaccaaa augcaugcag gagauccgc | 1260 |
| aagagcaaau caaggagauc aagaaggagc agcuuucagg auccccgugg auucugcuaa | 1320 |
| gggaaaauga agucagcaca cuuuauaaag gagaauacca cagagcucca guggccauaa | 1380 |
| aaguauucaa aaaacuccag gcuggcagca uugcaauagu gaggcagacu uucaauaagg | 1440 |
| agaucaaaac caugaagaaa uucgaaucuc ccaacauccu gcguauauuu gggauuugca | 1500 |
| uugaugaaac aggcuacacc auucagaagc accugaacuc cacggaaaaa ucagaagcuc | 1560 |
| aaacuuccug guaacucaag gcuaccaagu gaagauuugg guaccggcu gaguuugggg | 1620 |
| cuggcagccu ucagcacacc aauggugucu auggcagguug ugcaugggac aagaacauau | 1680 |
| gc | 1682 |

<210> SEQ ID NO 7
<211> LENGTH: 1297
<212> TYPE: DNA
<213> ORGANISM: Artificial Sequence
<220> FEATURE:
<223> OTHER INFORMATION: ZBP1 cDNA complement (DAI)

<400> SEQUENCE: 7

| | | | | | |
|---|---|---|---|---|---|
| tctcgacgtt | cttcgtggtc | cgagccggtg | aagtcttcgg | ggtcggagct | ggatcgggtg | 60 |
| ggagagtccc | ggtgtcacgt | cttcggacgt | gtggacggtt | cagagaggct | gaggaacgtc | 120 |
| gacgacagtc | gtaccgggtc | cgaggacgac | tgggcccgtc | tcttccggtg | gaacttgttt | 180 |
| cttaggacgt | ccacgactgt | ctccgaccga | ggggccactt | gaacgggtc | gaccacttcc | 240 |
| ttacggttcg | tgggttctcc | ctcgagttgg | ttcaggagat | ggcttacttt | ttcctcaact | 300 |
| ttcagaggga | gtgtagggga | cggtggacca | cgaacccgcc | ctgactagga | cttccgctcc | 360 |
| caggacgtct | cgaccggaac | aggtcgggac | ggctctccgg | ggtcgttgta | cgtcgatgtt | 420 |
| aaggtctctg | ggaccggga | gtcaagtcgg | ttgttgccct | ccttctgtag | atgtccaaag | 480 |
| agtttctgtt | accaggggtc | tcccgggacc | agtagcgggt | tcgtgaccct | tactcctgtc | 540 |
| gttttctaca | cttggctctg | aacatgtcct | acttctcgtc | cgtggaagac | ctgtacctac | 600 |
| tcgtcaggtt | tcgtacctgc | taaatggcgg | gtcttctaag | accttcttct | cgtttcagtc | 660 |
| ggagttaata | aatggtcgtg | ttaggttagt | tgtactagac | ggtcttacct | gggttgtcga | 720 |
| cctaaaggta | acgtttgagg | cttcggtagg | tctaacctgt | gcccttgtag | taatgttctg | 780 |
| tctgtcagag | gtccctcctg | ccaaggcggc | caggtgcggt | ggaggaagt | taccgtggtc | 840 |
| cactaaggag | ttgaaccccc | tgggatcaac | tagggacccc | cggggtcctg | taggtgtacc | 900 |
| tcgtcaggta | tgactctgcc | cacgtcgacc | ctgtgtcgtt | actctactcc | gaggtgccgc | 960 |
| agggcaggct | cccgggacgg | gtgtagggg | gaccgtcggg | gggtcacaag | gtcacgtcac | 1020 |
| ccttcgtccg | tcgtctcctc | tctcctcgac | ttagggtctc | cttctgtgac | tgcaggtcta | 1080 |
| gtcggcccgc | cctagtcacc | ccgtctgggt | gacgccctag | tcacctcgtc | tttctgcgaa | 1140 |
| gggtctgtcg | tgttgtcgtg | ctcgcctcag | agacggtgac | gacggccggg | tcttcgaagc | 1200 |
| aaacttcgtt | cttaagggtc | aggtccttga | gtgggactcc | cccttcggcg | ggtctcttag | 1260 |
| gtgtacttta | gcacgaaaga | gctcctgcgg | tggtagc | | | 1297 |

<210> SEQ ID NO 8
<211> LENGTH: 1557
<212> TYPE: DNA
<213> ORGANISM: Artificial Sequence
<220> FEATURE:
<223> OTHER INFORMATION: RIPK3 cDNA complement

<400> SEQUENCE: 8

| | | | | | |
|---|---|---|---|---|---|
| tacagcacgc | agttcaatac | cgggtcgcca | cgggggcggg | ggaaccacag | gtagctcctt | 60 |
| gacctcttgg | tcctcgagca | gccgtttccg | cccaagccgt | gtcacaaggc | ccgcgttgta | 120 |
| tccttcaccc | cgatgctaca | ccgccagttc | tagcatttga | gtttccgcta | taggtccctc | 180 |
| cagttccggt | accgttcaga | cctattgctt | aagcacgacg | cggatcttcc | ccaatagctc | 240 |
| ttccacttga | ccctggttct | agggttcggc | cgagaccact | gatttaagta | cctcttgccg | 300 |
| aggaacagcc | ccgacgacgt | cagggtcacg | ggagccggga | ccggcgagga | acggcggac | 360 |
| gactttcttc | accacgaacc | ctacaaaatg | gacgtgctgg | tcttgggcca | cgaggacgtg | 420 |
| gccctggagt | tcggtaggtt | gcaggacgac | ctgggtctcg | acgtgcagtt | cgaccgtcta | 480 |

```
aaaccggaca ggtgtaaagt ccctccgagt gtcagtccct gtcccaggcc cctcggtccc     540
ccgtgggacc cgatgaaccg gggtcttgac aaacaattgc atttggcctt ccggaggtgt     600
cggtcactgc agatgtcgaa gccctaggat tacacccgtc acgaacgacc ttctcttcaa     660
ctcaacggtt ggcttggtag tgagcacatg cttcgtcaca cgttgtccgt cttggccgga     720
agtaaccgac tcgacggggt tcggcccgga ctctgagggc cgaatcttcc tgacttcctc     780
gattacgtcg agacgacctc gtcactcggg ttcctgtctg ggaggaaggt ccttacggat     840 ggttttgac tacttcagaa ggtctaccac ctcttgttat acttacgacg acagaggtgc      900
catttcctaa aggacagagt cgagtcctcg tcgttatcct ctaaaagata gggtctcagt     960
ccggttcctc cctgtcttta cctaccgaaa tcctcttggt atcttttggt cgtgagagca    1020
ttactacagt accaaagact caccgatttg tttgacttag atctcctcgg agggtcgaga    1080
caaggatttt ttacgggctc ggaatggttc tcctcgtccc gtgttctcct cgtccaaggt    1140
gttcggacct gtcgtccgtg tagaagtcta agctaccggg ttggagggt ctgaggtctc     1200 tggagttgaa agtctttggt ctacgggtcg ggatggagtt gaccttgtgg ttcaggacct    1260
ggggctccct tagtccccg actctctgtt ccgtacttga ccaggacgtc ctggggcctc     1320
ggtttaggtc attgtcccgc tggcgagcaa ttgtatatgt tgacgagacc ccacgttcaa    1380
cctctgttgt tgatgaactg atacgttgtc tgttgacgga acgggtgtac cccgaaccgt    1440
ggaagcccgt tcccctcccc gaacgtcgtg ggggtggtc atccaagcgt tcttccggga     1500
tttctaggac ttcggacctc gtccggtgtc ccaaccatat tagtatcgcc ctttatt       1557

<210> SEQ ID NO 9
<211> LENGTH: 1682
<212> TYPE: DNA
<213> ORGANISM: Artificial Sequence
<220> FEATURE:
<223> OTHER INFORMATION: MLKL cDNA complement

<400> SEQUENCE: 9
taggtcgtgt ctcttcgttt gtggtcttcg aagagaggtt gaaagtcaaa aagagatttg      60
aaggtcagga agagtatgac acaggaccaa tattatcaac gaccctggaa taagataaga    120
cttaggggtc gggatttct tccgaaccat gactgcacat gtcgcatcaa tgggtcactg     180 aaacccttc cgtccttctc acacctttcc tgtcctcctt ccttccctcc ccggcaccga     240
ggctcgacgg atctttcgcc gaggtccctc ggtcccgtgg cactcggacc accaaccgtc    300
gacctcggtg cagcctcccc cttcacagcg tcgtaagaga cgtccgtagt gtctggactc    360
cgtcaccgga ggcctcccgt gacctgtctt tgtcggtagg ttcaccgact cacctccctg    420
ggacgagttc acgtcgacgt caccggcccc aaagggagtc catccctagc cccgcggaac    480
agcggcggtc ggtgcacacc gcaggccatg tcagtcgtct cacgtccac gcccgtggtc     540 ctttcccccg cgtcccttg agggcgcccg gagcgcaaac gtttgaagag cggaccccgtc   600 ctccgccagc acccttctt ccaccttctc gctcgaaaaa ccttgacacg tgccctgtct     660
aacctgcgtg tggggagccc tccgcgcttc cgtaccttt aaacttcgta taatagtggg    720
aaccggtcca gtaggtgttt gccacacttc tctactttat gacgttcttt gtcacggccg    780
cggacccggt ggcgcaggag ccggactagt tcggagacct acgaggtc ctggttcctt     840 tctcctcgca cgggagactc ttcaattggt gtcggtactt ggcgaagttc cgacgggacc    900
tcctccgatt acccctctat cttttcaagt cgttatctag gttatagcg tccaaagatt    960 gtcgttcggt cctgttttat gagaagttcc tgcacttgtc cttcgactca ctacagacct   1020
```

```
tcctcgagag cgacaatgaa gtccaactcg ttgcgtacgg acaaagtggg tattcggttc    1080
ctcgcaggac ccgtgtcctt ctagtcgtcc tacgtctgct tctgtccgct cgaaaggtct    1140
acgattcttc tctattactt ttttatcttc gaagtgactc tgctaatctt tagttgtact    1200
ttctttagtt cctttgaaac tccgtcataa atggtggttt tacgtacgtc ctctagggcg    1260
ttctcgttta gttcctctag ttcttcctcg tcgaaagtcc taggggcacc taagacgatt    1320 ccctttact tcagtcgtgt gaaatatttc ctcttatggt gtctcgaggt caccggtatt    1380
ttcataagtt ttttgaggtc cgaccgtcgt aacgttatca ctccgtctga aagttattcc    1440
tctagttttg gtacttcttt aagcttagag ggttgtagga cgcatataaa ccctaaacgt    1500
aactactttg tccgatgtgg taagtcttcg tggacttgag gtgccttttt agtcttcgag    1560
tttgaaggac cattgagttc cgatggttca cttctaaacc catggaccga ctcaaacccc    1620
gaccgtcgga agtcgtgtgg ttaccacagt taccgtccac acgtaccctg ttcttgtata    1680
cg                                                                   1682

<210> SEQ ID NO 10
<211> LENGTH: 1297
<212> TYPE: RNA
<213> ORGANISM: Artificial Sequence
<220> FEATURE:
<223> OTHER INFORMATION: ZBP1 (DAI) RNA complement

<400> SEQUENCE: 10
ucucgacguu cuucgugguc cgagccggug aagucuucgg ggucggagcu ggaucgggug      60 ggagagucccc ggugucacgu cuucggacgu guggacgguu cagagaggcu gaggaacguc    120
gacgacaguc guaccgdguc cgaggacgac ugggcccguc ucuuccggug gaacuuguuu    180
cuuaggacgu ccacgacugu cuccgaccga ggggccacuu ugaacggguc gaccacuucc    240
uuacgguucg uggguucucc cucgaguugg uucaggagau ggcuuacuuu uccucaacu      300 uucagaggga guguagggga cgguggacca cgaacccgcc cugacuagga cuuccgcucc    360
caggacgucu cgaccggaac aggucgggac ggcucuccgg ggucguugua cgucgauguu    420
aaggucucug gggaccggga gucaagucgg uuguugcccu ccuucguag auguccaaag      480 aguuucuguu accagggguc ucccgggacc aguagcgggu ucgugacccu uacuccuguc    540 guuucuaca cuuggcucug aacaugaaaa acuucucuuauc cguggaagac cuguaccuac   600
ucgucagguu ucguaccugc uaaauggcgg gucuucuaag accuucuucu cguuucaguc    660
ggaguuaaua aauggucgug uuagguuagu uguacuagac ggucuaccu gggugucga      720 ccuaaaggua acguuugagg cuucgguagg ucuaaccugu gcccuuguag uauguucug      780 ucugucagag gucccuccug ccaaggcggc caggugcggu ggagggaagu uaccguggguc   840 cacuaaggag uugaaccccc ugggaucaac uagggacccc cggggguccug uagguguac     900 ucgucaggua ugacucugcc cacgucgacc cuguguucguu acucuaccuc gaggugccgc   960
agggcaggcu cccgggacgg guguagggg gaccgucggg gggucacaag gucacgucac    1020
ccuucguccg ucgucuccuc ucuccucugac uuagggucuc cuucguugac ugcaggcuaa  1080
gucggcccgc ccuagucacc ccgucggugu gaaaacgcccuag ucaccucguc uuucugcgaa  1140
gggucugucg uguugucgug cucgccucag agacggugac gacggccggg ucuucgaagc   1200
aaacuucguu cuuaagggguc aggucccuuga gugggacucc ccuucggcgg ggucucuuag  1260
guguacuuua gcacgaaaga gcuccugcgg uggugagc                            1297
```

<210> SEQ ID NO 11
<211> LENGTH: 1557
<212> TYPE: RNA
<213> ORGANISM: Artificial Sequence
<220> FEATURE:
<223> OTHER INFORMATION: RIPK3 RNA complement

<400> SEQUENCE: 11

| | | | | | |
|---|---|---|---|---|---|
| uacagcacgc | aguucaauac | cgggucgcca | cggggggcggg | ggaaccacag | guagcuccuu | 60 |
| gaccucuugg | uccucgagca | gccguuuccg | cccaagccgu | gucacaaggc | ccgcguugua | 120 |
| uccuucaccc | cgaugcuaca | ccgccaguuc | uagcauuuga | guuccgcuua | uaggucccuc | 180 |
| caguccggu | accguucaga | ccuauugcuu | aagcacgacg | cggaucuucc | ccaauagcuc | 240 |
| uuccacuuga | cccugguucu | agggguucggc | cgagaccacu | gauuuaagua | ccucuugccg | 300 |
| aggaacagcc | ccgacgacgu | cagggucacg | ggagccggga | ccggcgagga | aacggcggac | 360 |
| gacuuucuuc | accacgaacc | cuacaaaaug | gacgugcugg | ucuugggcca | cgaggacgug | 420 |
| gcccuggagu | ucgguagguu | gcaggacgac | cugggucucg | acgugcaguu | cgaccgucua | 480 |
| aaaccggaca | ggguguaaagu | cccuccgagu | gucagucccu | gucccaggcc | ccucggsuccc | 540 |
| ccgugggacc | cgaugaaccg | gggucuugac | aaacaauugc | auuuggccuu | ccggaggugu | 600 |
| cggucacugc | agaugucgaa | gcccuaggau | uacacccguc | acgaacgacc | uucucuucaa | 660 |
| cucaacgguu | ggcuugguag | ugagcacaug | cuucgcucaca | cguugccgu | cuggccggga | 720 |
| aguaaccgac | ucgacggggu | ucggcccgga | cucugagggc | cgaaucuucc | ugacuuccuc | 780 |
| gauuacgucg | agacgaccuc | gucacucggg | uuccugucug | ggaggaaggu | ccuuacggau | 840 |
| gguuuuugac | uacuucagaa | ggucuaccac | cucuguuau | acuuacgacg | acagaggugc | 900 |
| cauuccuaa | aggacagagu | cgaguccucg | ucguuauccu | cuaaaagaua | gggucucagu | 960 |
| ccgguuccuc | ccugucuuua | ccuaccgaaa | uccucuuggu | aucuuuuggu | cgugagagca | 1020 |
| uuacuacagu | accaaagacu | caccgauuug | uuugacuuag | aucuccucgg | aggucgaga | 1080 |
| caaggauuuu | uuacgggcuc | ggaaugguuc | uccucguccc | guguucuccu | cguccaaggu | 1140 |
| guucggaccu | gucguccgug | uagaagucua | agcuaccggg | uuggagggu | cugaggcucu | 1200 |
| uggaguugaa | agucuuuggu | cuacgggucg | ggauggaguu | gaccuugugg | uucaggaccu | 1260 |
| gggcucccu | uagucccccg | acucucuguu | ccguacuuga | ccaggacguc | cuggggccuc | 1320 |
| gguuuaggcu | auugucccgc | uggcgagcaa | uuguauaugu | ugacgagacc | ccacguucaa | 1380 |
| ccucuguugu | ugaugaacug | auacguugu | uguugacgga | acggguguac | cccgaaccgu | 1440 |
| ggaagcccgu | uccccucccc | gaacgucgug | gggguggguc | auccaagcgu | ucuuccggga | 1500 |
| uuucuaggac | uucggaccuc | guccgguguc | ccaaccauau | aguaucgcc | cuuuauu | 1557 |

<210> SEQ ID NO 12
<211> LENGTH: 1682
<212> TYPE: RNA
<213> ORGANISM: Artificial Sequence
<220> FEATURE:
<223> OTHER INFORMATION: MLKL RNA complement

<400> SEQUENCE: 12

| | | | | | |
|---|---|---|---|---|---|
| uaggucgugu | cucuucguuu | guggucuucg | aagagagguu | gaaagucaaa | aagagauuug | 60 |
| aaggucagga | agaguaugac | acaggaccaa | uauuaucaac | gacccuggaa | uaagauaaga | 120 |
| cuuaggggguc | ggggauuucu | uccgaaccau | gacugcacau | gucgcaucaa | ugggucacug | 180 |
| aaaccccuuc | cguccuucuc | acaccuuucc | ugucuccuu | ccuucccucc | ccggcaccga | 240 |

```
ggcucgacgg aucuuucgcc gagguccocuc ggucccgugg cacucggacc accaaccguc   300
gaccucggug cagccucccc cuucacagcg ucguaagaga cguccguagu ucuggacuc    360 cgucaccgga ggccucccgu gaccugucuu ugucgguagg uucaccgacu caccucccug    420
ggacgaguuc acgucgacgu caccggcccc aaagggaguc cauccocuagc ccocgcggaac   480 agcggcgguc ggugcacacc gcaggccaug ucagucgucu cacgucccac gcccgugguc    540 cuuuccocccg cgucccocuug agggcgcccc gagcgcaaac guuugaagag cggaccocguc   600 cuccgccagc acccuuucuu ccaccuucuc gcucgaaaaa ccuugacacg ugcccugucu    660
aaccugcgug uggggagccc uccgcgcuuc cguaccuuuu aaacuucgua aauaguggg     720 aaccggucca gagguguuu gccacacuuc ucacuuuau gacguucuuu gucacggccg    780
cggacccggu ggcgcaggag ccggacuagu ucggagaccu cuacgagguc cugguuccuu    840
ucuccucgca cgggagacuc uucaauuggu gucgguacuu ggcgaaguuc cgacgggacc    900
uccuccgauu accccucuau cuuuucaagu cguuaucuag guuauagacg uccaaagauu    960
gucguucggu ccuguuuuau gagaaguucc ugcacuuguc cuucgacuca cuacagaccu   1020
uccucgagag cgacaaugaa guccaacucg uugcguacgg acaaagugggg uauucgguuc   1080 cucgcaggac ccgugucocuu cuagucgucc uacgucugcu ucuguccgcu cgaaaggucu   1140
acgauucuuc ucuauuacuu uuuuaucuuc gaagugacuc ugcuaaucuu uaguuguacu   1200
uucuuuaguu ccuugaaac ucccgucauaa auggugguu uacgacguc cucuagggcg    1260 uucucguuua guccucuag uucuuccocug ucgaaaguucc uagggcacc uaagacgauu    1320 cccuuuuacu ucagucgugu gaaauauuuc cucuuaugguu gucucgaggu caccgguauu   1380
uucauaaguu uuuugagguc cgaccgucgu aacguuauca cuccgucuga agguuauuc    1440 ucuaguuuug guacuucuuu aagcuuagag gguuguuggga cgcauauaaa cccuaaacgu    1500
aacuacuuug uccgaugugg uaagucuucg uggacuugag gugccuuuu aguucuucgag   1560 uuugaaggac cauugaguuc cgaugguuca cuucuaaacc cauggaccga cucaaacccc    1620
gaccgucgga agucgugugg uuaccacagu uaccguccac acguacccug uucuuguaua   1680
cg                                                                    1682
```

<210> SEQ ID NO 13
<211> LENGTH: 429
<212> TYPE: PRT
<213> ORGANISM: Artificial Sequence
<220> FEATURE:
<223> OTHER INFORMATION: ZBP1 (DAI) Protein

<400> SEQUENCE: 13

```
Met Ala Gln Ala Pro Ala Asp Pro Gly Arg Glu Gly His Leu Glu Gln
  1               5                  10                  15

Arg Ile Leu Gln Val Leu Thr Glu Ala Gly Ser Pro Val Lys Leu Ala
                 20                  25                  30

Gln Leu Val Lys Glu Cys Gln Ala Pro Lys Arg Glu Leu Asn Gln Val
             35                  40                  45

Leu Tyr Arg Met Lys Lys Glu Leu Lys Val Ser Leu Thr Ser Pro Ala
         50                  55                  60

Thr Trp Cys Leu Gly Gly Thr Asp Pro Glu Gly Gly Pro Ala Glu
 65                  70                  75                  80

Leu Ala Leu Ser Ser Pro Ala Lys Arg Pro Gln Gln His Ala Ala Thr
                 85                  90                  95
```

```
Ile Pro Glu Thr Pro Gly Pro Gln Phe Ser Gln Gln Arg Glu Glu Asp
            100                 105                 110
Ile Tyr Arg Phe Leu Lys Asp Asn Gly Pro Gln Arg Ala Leu Val Ile
        115                 120                 125
Ala Gln Ala Leu Gly Met Arg Thr Ala Lys Asp Val Asn Arg Asp Leu
    130                 135                 140
Tyr Arg Met Lys Ser Arg His Leu Leu Asp Met Asp Glu Gln Ser Lys
145                 150                 155                 160
Ala Trp Thr Ile Tyr Arg Pro Glu Asp Ser Gly Arg Arg Ala Lys Ser
                165                 170                 175
Ala Ser Ile Ile Tyr Gln His Asn Pro Ile Asn Met Ile Cys Gln Asn
            180                 185                 190
Gly Pro Asn Ser Trp Ile Ser Ile Ala Asn Ser Glu Ala Ile Gln Ile
        195                 200                 205
Gly His Gly Asn Ile Ile Thr Arg Gln Thr Val Ser Arg Glu Asp Gly
    210                 215                 220
Ser Ala Gly Pro Arg His Leu Pro Ser Met Ala Pro Gly Asp Ser Ser
225                 230                 235                 240
Thr Trp Gly Thr Leu Val Asp Pro Trp Gly Pro Gln Asp Ile His Met
                245                 250                 255
Glu Arg Ser Ile Leu Arg Arg Val Gln Leu Gly His Ser Asn Glu Met
            260                 265                 270
Arg Leu His Gly Val Pro Ser Glu Gly Pro Ala His Ile Pro Pro Gly
        275                 280                 285
Ser Pro Pro Val Ser Ala Thr Ala Ala Gly Pro Glu Ala Ser Phe Glu
    290                 295                 300
Ala Arg Ile Pro Ser Pro Gly Thr His Pro Glu Gly Glu Ala Ala Gln
305                 310                 315                 320
Arg Ile His Met Lys Ser Cys Phe Leu Glu Asp Ala Thr Ile Gly Asn
                325                 330                 335
Ser Asn Lys Met Ser Ile Ser Pro Gly Val Ala Gly Pro Gly Gly Val
            340                 345                 350
Ala Gly Ser Gly Glu Gly Glu Pro Gly Glu Asp Ala Gly Arg Arg Pro
        355                 360                 365
Ala Asp Thr Gln Ser Arg Ser His Phe Pro Arg Asp Ile Gly Gln Pro
    370                 375                 380
Ile Thr Pro Ser His Ser Lys Leu Thr Pro Lys Leu Glu Thr Met Thr
385                 390                 395                 400
Leu Gly Asn Arg Ser His Lys Ala Ala Glu Gly Ser His Tyr Val Asp
                405                 410                 415
Glu Ala Ser His Glu Gly Ser Trp Trp Gly Gly Ile
            420                 425

<210> SEQ ID NO 14
<211> LENGTH: 518
<212> TYPE: PRT
<213> ORGANISM: Artificial Sequence
<220> FEATURE:
<223> OTHER INFORMATION: RIPK3 Protein

<400> SEQUENCE: 14

Met Ser Cys Val Lys Leu Trp Pro Ser Gly Ala Pro Ala Pro Leu Val
1               5                   10                  15
Ser Ile Glu Glu Leu Glu Asn Gln Glu Leu Val Gly Lys Gly Gly Phe
            20                  25                  30
```

```
Gly Thr Val Phe Arg Ala Gln His Arg Lys Trp Gly Tyr Asp Val Ala
            35                  40                  45

Val Lys Ile Val Asn Ser Lys Ala Ile Ser Arg Glu Val Lys Ala Met
 50                  55                  60

Ala Ser Leu Asp Asn Glu Phe Val Leu Arg Leu Glu Gly Val Ile Glu
 65                  70                  75                  80

Lys Val Asn Trp Asp Gln Asp Pro Lys Pro Ala Leu Val Thr Lys Phe
                 85                  90                  95

Met Glu Asn Gly Ser Leu Ser Gly Leu Leu Gln Ser Gln Cys Pro Arg
            100                 105                 110

Pro Trp Pro Leu Leu Cys Arg Leu Leu Lys Glu Val Val Leu Gly Met
        115                 120                 125

Phe Tyr Leu His Asp Gln Asn Pro Val Leu Leu His Arg Asp Leu Lys
    130                 135                 140

Pro Ser Asn Val Leu Leu Asp Pro Glu Leu His Val Lys Leu Ala Asp
145                 150                 155                 160

Phe Gly Leu Ser Thr Phe Gln Gly Gly Ser Gln Ser Gly Thr Gly Ser
                165                 170                 175

Gly Glu Pro Gly Gly Thr Leu Gly Tyr Leu Ala Pro Glu Leu Phe Val
            180                 185                 190

Asn Val Asn Arg Lys Ala Ser Thr Ala Ser Asp Val Tyr Ser Phe Gly
        195                 200                 205

Ile Leu Met Trp Ala Val Leu Ala Gly Arg Glu Val Glu Leu Pro Thr
    210                 215                 220

Glu Pro Ser Leu Val Tyr Glu Ala Val Cys Asn Arg Gln Asn Arg Pro
225                 230                 235                 240

Ser Leu Ala Glu Leu Pro Gln Ala Gly Pro Glu Thr Pro Gly Leu Glu
                245                 250                 255

Gly Leu Lys Glu Leu Met Gln Leu Cys Trp Ser Ser Glu Pro Lys Asp
            260                 265                 270

Arg Pro Ser Phe Gln Glu Cys Leu Pro Lys Thr Asp Glu Val Phe Gln
        275                 280                 285

Met Val Glu Asn Asn Met Asn Ala Ala Val Ser Thr Val Lys Asp Phe
    290                 295                 300

Leu Ser Gln Leu Arg Ser Ser Asn Arg Arg Phe Ser Ile Pro Glu Ser
305                 310                 315                 320

Gly Gln Gly Gly Thr Glu Met Asp Gly Phe Arg Arg Thr Ile Glu Asn
                325                 330                 335

Gln His Ser Arg Asn Asp Val Met Val Ser Glu Trp Leu Asn Lys Leu
            340                 345                 350

Asn Leu Glu Glu Pro Pro Ser Ser Val Pro Lys Lys Cys Pro Ser Leu
        355                 360                 365

Thr Lys Arg Ser Arg Ala Gln Glu Glu Gln Val Pro Gln Ala Trp Thr
    370                 375                 380

Ala Gly Thr Ser Ser Asp Ser Met Ala Gln Pro Pro Gln Thr Pro Glu
385                 390                 395                 400

Thr Ser Thr Phe Arg Asn Gln Met Pro Ser Pro Thr Ser Thr Gly Thr
                405                 410                 415

Pro Ser Pro Gly Pro Arg Gly Asn Gln Gly Ala Glu Arg Gln Gly Met
            420                 425                 430

Asn Trp Ser Cys Arg Thr Pro Glu Pro Asn Pro Val Thr Gly Arg Pro
        435                 440                 445

Leu Val Asn Ile Tyr Asn Cys Ser Gly Val Gln Val Gly Asp Asn Asn
```

```
                450                 455                 460
Tyr Leu Thr Met Gln Gln Thr Thr Ala Leu Pro Thr Trp Gly Leu Ala
465                 470                 475                 480

Pro Ser Gly Lys Gly Arg Gly Leu Gln His Pro Pro Val Gly Ser
                485                 490                 495

Gln Glu Gly Pro Lys Asp Pro Glu Ala Trp Ser Arg Pro Gln Gly Trp
                500                 505                 510

Tyr Asn His Ser Gly Lys
            515

<210> SEQ ID NO 15
<211> LENGTH: 471
<212> TYPE: PRT
<213> ORGANISM: Artificial Sequence
<220> FEATURE:
<223> OTHER INFORMATION: MLKL Protein

<400> SEQUENCE: 15

Met Glu Asn Leu Lys His Ile Ile Thr Leu Gly Gln Val Ile His Lys
1               5                   10                  15

Arg Cys Glu Glu Met Lys Tyr Cys Lys Lys Gln Cys Arg Arg Leu Gly
                20                  25                  30

His Arg Val Leu Gly Leu Ile Lys Pro Leu Glu Met Leu Gln Asp Gln
            35                  40                  45

Gly Lys Arg Ser Val Pro Ser Glu Lys Leu Thr Thr Ala Met Asn Arg
        50                  55                  60

Phe Lys Ala Ala Leu Glu Glu Ala Asn Gly Glu Ile Glu Lys Phe Ser
65                  70                  75                  80

Asn Arg Ser Asn Ile Cys Arg Phe Leu Thr Ala Ser Gln Asp Lys Ile
                85                  90                  95

Leu Phe Lys Asp Val Asn Arg Lys Leu Ser Asp Val Trp Lys Glu Leu
                100                 105                 110

Ser Leu Leu Leu Gln Val Glu Gln Arg Met Pro Val Ser Pro Ile Ser
            115                 120                 125

Gln Gly Ala Ser Trp Ala Gln Glu Asp Gln Gln Asp Ala Asp Glu Asp
        130                 135                 140

Arg Arg Ala Phe Gln Met Leu Arg Arg Asp Asn Glu Lys Ile Glu Ala
145                 150                 155                 160

Ser Leu Arg Arg Leu Glu Ile Asn Met Lys Glu Ile Lys Glu Thr Leu
                165                 170                 175

Arg Gln Tyr Leu Pro Pro Lys Cys Met Gln Glu Ile Pro Gln Glu Gln
            180                 185                 190

Ile Lys Glu Ile Lys Lys Glu Gln Leu Ser Gly Ser Pro Trp Ile Leu
        195                 200                 205

Leu Arg Glu Asn Glu Val Ser Thr Leu Tyr Lys Gly Glu Tyr His Arg
210                 215                 220

Ala Pro Val Ala Ile Lys Val Phe Lys Lys Leu Gln Ala Gly Ser Ile
225                 230                 235                 240

Ala Ile Val Arg Gln Thr Phe Asn Lys Glu Ile Lys Thr Met Lys Lys
                245                 250                 255

Phe Glu Ser Pro Asn Ile Leu Arg Ile Phe Gly Ile Cys Ile Asp Glu
            260                 265                 270

Thr Val Thr Pro Pro Gln Phe Ser Ile Val Met Glu Tyr Cys Glu Leu
        275                 280                 285

Gly Thr Leu Arg Glu Leu Leu Asp Arg Glu Lys Asp Leu Thr Leu Gly
```

290                 295                 300

Lys Arg Met Val Leu Val Leu Gly Ala Ala Arg Gly Leu Tyr Arg Leu
305                 310                 315                 320

His His Ser Glu Ala Pro Glu Leu His Gly Lys Ile Arg Ser Ser Asn
                325                 330                 335

Phe Leu Val Thr Gln Gly Tyr Gln Val Lys Leu Ala Gly Phe Glu Leu
                340                 345                 350

Arg Lys Thr Gln Thr Ser Met Ser Leu Gly Thr Thr Arg Glu Lys Thr
                355                 360                 365

Asp Arg Val Lys Ser Thr Ala Tyr Leu Ser Pro Gln Glu Leu Glu Asp
                370                 375                 380

Val Phe Tyr Gln Tyr Asp Val Lys Ser Glu Ile Tyr Ser Phe Gly Ile
385                 390                 395                 400

Val Leu Trp Glu Ile Ala Thr Gly Asp Ile Pro Phe Gln Gly Cys Asn
                405                 410                 415

Ser Glu Lys Ile Arg Lys Leu Val Ala Val Lys Arg Gln Gln Glu Pro
                420                 425                 430

Leu Gly Glu Asp Cys Pro Ser Glu Leu Arg Glu Ile Ile Asp Glu Cys
                435                 440                 445

Arg Ala His Asp Pro Ser Val Arg Pro Ser Val Asp Glu Ile Leu Lys
                450                 455                 460

Lys Leu Ser Thr Phe Ser Lys
465                 470

<210> SEQ ID NO 16
<211> LENGTH: 24
<212> TYPE: DNA
<213> ORGANISM: Artificial Sequence
<220> FEATURE:
<223> OTHER INFORMATION: CRISPR 1

<400> SEQUENCE: 16
tctggagtca cacaagagtc ccct                                              24

<210> SEQ ID NO 17
<211> LENGTH: 30
<212> TYPE: DNA
<213> ORGANISM: Artificial Sequence
<220> FEATURE:
<223> OTHER INFORMATION: CRISPR 2

<400> SEQUENCE: 17
gctcagtaca tctacatgga caagtccttg                                        30

<210> SEQ ID NO 18
<211> LENGTH: 12
<212> TYPE: RNA
<213> ORGANISM: Artificial Sequence
<220> FEATURE:
<223> OTHER INFORMATION: Universal genomic viral RNA (vRNA) primer

<400> SEQUENCE: 18
agcaaaagca gg                                                           12

<210> SEQ ID NO 19
<211> LENGTH: 23
<212> TYPE: DNA
<213> ORGANISM: Artificial Sequence
<220> FEATURE:
<223> OTHER INFORMATION: Primer 1

```
<400> SEQUENCE: 19
atggaaagaa taaaagaact aag                                          23

<210> SEQ ID NO 20
<211> LENGTH: 23
<212> TYPE: DNA
<213> ORGANISM: Artificial Sequence
<220> FEATURE:
<223> OTHER INFORMATION: Primer 2

<400> SEQUENCE: 20
ctaattgatg gccatccgaa ttc                                          23

<210> SEQ ID NO 21
<211> LENGTH: 20
<212> TYPE: DNA
<213> ORGANISM: Artificial Sequence
<220> FEATURE:
<223> OTHER INFORMATION: Targeted sequence

<400> SEQUENCE: 21
tgagaacgtt ctgctcctgc                                              20
```

RNA VIRUS VECTORS CARRYING DAI AND RIPK3

STATEMENT OF GOVERNMENT SUPPORT

This invention was made with government support under Grant Nos. CA168621 and AI113469 awarded by the National Institutes of Health. The government has certain rights in the invention.

FIELD

The present disclosure relates generally to the field of virotherapy. More particularly, the present disclosure relates to RNA viruses as vectors for delivery of at least one of DNA-dependent activator of interferon-regulatory factors (DAI) and receptor-interacting serine/threonine-protein kinase 3 (RIPK3) to infected cells or tumor cells to facilitate death of such cells as well as to enhance an immune response against the underlying infection or tumor.

BACKGROUND

Various publications, including patents, published applications, accession numbers, technical articles and scholarly articles are cited throughout the specification. Each of these cited publications is incorporated by reference, in its entirety and for all purposes, in this document.

Influenza A virus (IAV), a member of the family Orthomyxoviridae and primary causative agent of influenza in birds and mammals, is an enveloped virus with a negative-sense, single-stranded, segmented RNA genome. Acute IAV infection is accompanied by lysis of infected primary epithelial cells and fibroblasts in culture, and by destruction of airway epithelia in vivo, indicative of an integral role for cell death in the virus life cycle, the immune response to this virus, or both. It is believed that cell death may represent a host defense mechanism that limits both virus spread and host immunopathology early in an infection.

In murine fibroblasts and airway epithelial cells, IAV lysis is driven by receptor-interacting serine/threonine-protein kinase 3 (RIPK3). Upon IAV infection, RIPK3 nucleates a necrosome complex, that minimally also includes receptor-interacting serine/threonine-protein kinase 1 (RIPK1) and mixed lineage kinase domain-like (MLKL), which then activates both apoptosis, via a RIPK1+Fas-Associated protein with Death Domain (FADD)+Caspase 8 axis, and necroptosis, mediated by MLKL. Formation of the RIPK3 necrosome and consequent activation of cell death both require active IAV replication. DNA-dependent activator of interferon-regulatory factors (DAI) senses IAV genomic RNA and links replicating IAV to RIPK3 activation. It is believed that DAI recognizes IAV RNA by a mechanism requiring the second of its Zα domains, and nucleates a RHIM-dependent RIPK3-containing necrosome. DAI also mediates IAV-induced RIPK3-independent apoptosis. Consequently, cells lacking DAI are remarkably resistant to IAV-triggered lysis, and DAI-deficient mice are hyper-susceptible to lethal infection by this virus.

SUMMARY

The present disclosure provides RNA virus vectors. These RNA virus vectors may be used for treating tumors, and also for treating virus infections, particularly for human patients. These RNA virus vectors may be used in the manufacture of a medicament, including a medicament for treating tumors as well as a medicament for treating viral infections.

In general, an RNA virus vector comprises an RNA virus that comprises at least a gene encoding the human DNA-dependent activator of interferon-regulatory factors (DAI) protein. The RNA virus may further comprise a gene encoding the human receptor-interacting serine/threonine-protein kinase 3 (RIPK3) protein. In some embodiments, the RNA virus is a positive sense RNA virus, non-limiting examples of which include an attenuated Kunjin virus, Polio virus, Semliki Forest virus, Venezuelan Equine Encephalitis virus, or Sinbis virus. In some embodiments, the RNA virus is a negative sense RNA virus, non-limiting examples of which include an attenuated Rabies virus, Influenza virus, Vesicular Stomatitis virus, Respiratory Syncytial virus, Sendai virus, Measles virus, New Castle Disease virus, or Simian Virus 5 (SV5) virus. In some embodiments, the RNA virus is Influenza virus. In some embodiments, the RNA virus is a retrovirus, such as an attenuated Lentivirus.

The gene encoding the human DAI protein may comprise a nucleic acid sequence encoding the amino acid sequence of SEQ ID NO:13. The gene may comprise DNA or RNA, and RNA may comprise a negative sense RNA. The gene encoding the human DAI protein may comprise the nucleic acid sequence of SEQ ID NO:1 or SEQ ID NO:4, or comprise the complement thereof.

The gene encoding the human RIPK3 protein may comprise a nucleic acid sequence encoding the amino acid sequence of SEQ ID NO:14. The gene may comprise DNA or RNA, and RNA may comprise a negative sense RNA. The gene encoding the human RIPK3 protein may comprise the nucleic acid sequence of SEQ ID NO:2 or SEQ ID NO:5, or comprise the complement thereof.

In some embodiments, the RNA virus further comprises a gene encoding the human mixed lineage kinase domain-like (MLKL) protein. The gene encoding the human MLKL protein may comprise a nucleic acid sequence encoding the amino acid sequence of SEQ ID NO:15. The gene may comprise DNA or RNA, and RNA may comprise a negative sense RNA. The gene encoding the human MLKL protein may comprise the nucleic acid sequence of SEQ ID NO:3 or SEQ ID NO:6, or comprise the complement thereof.

The RNA virus vectors may be used in a method for treating a tumor in a subject in need thereof. In general, such methods comprise infecting cells of the tumor with the RNA virus vector that comprises a gene encoding the human DAI protein and, optionally, a gene encoding the human RIPK3 protein and, optionally, a gene encoding the human MLKL protein. Such genes may comprise DNA or RNA, and RNA may comprise a negative sense RNA. The gene encoding the human DAI protein may comprise a nucleic acid sequence encoding the amino acid sequence of SEQ ID NO:13, for example, the nucleic acid sequence of SEQ ID NO:1 or SEQ ID NO:4. The gene encoding the human RIPK3 protein may comprise a nucleic acid sequence encoding the amino acid sequence of SEQ ID NO:14, for example, the nucleic acid sequence of SEQ ID NO:2 or SEQ ID NO:5. The gene encoding the human MLKL protein may comprise a nucleic acid sequence encoding the amino acid sequence of SEQ ID NO:15, for example, the nucleic acid sequence of SEQ ID NO:3 or SEQ ID NO:6. The methods may be used to treat any tumor. In some embodiments, the tumor is a tumor of the head and neck, esophagus, lung, breast, pancreas, kidney, liver, stomach, colon, ovary, uterus, prostate gland, bladder, or blood.

As part of the tumor-treating method, the step of infecting cells of the tumor may comprise administering the RNA virus vector to the subject. The RNA virus vector may be actively targeted to the tumor, or may travel via the blood or other biologic fluid to the tumor location.

The RNA virus vectors may be used in methods for treating a viral infection in a subject in need thereof. In general, such methods comprise comprising infecting cells infected with the viral infection with the RNA virus vector that comprises a gene encoding the human DAI protein and, optionally, a gene encoding the human RIPK3 protein and, optionally, a gene encoding the human MLKL protein. Such genes may comprise DNA or RNA, and RNA may comprise a negative sense RNA. The gene encoding the human DAI protein may comprise a nucleic acid sequence encoding the amino acid sequence of SEQ ID NO:13, for example, the nucleic acid sequence of SEQ ID NO:1 or SEQ ID NO:4. The gene encoding the human RIPK3 protein may comprise a nucleic acid sequence encoding the amino acid sequence of SEQ ID NO:14, for example, the nucleic acid sequence of SEQ ID NO:2 or SEQ ID NO:5. The gene encoding the human MLKL protein may comprise a nucleic acid sequence encoding the amino acid sequence of SEQ ID NO:15, for example, the nucleic acid sequence of SEQ ID NO:3 or SEQ ID NO:6. The methods may be used to treat any viral infection, including a negative sense viral infection. The methods may be used to treat an influenza virus infection, including influenza Type A, Type B, and Type C infections.

As part of the infection-treating methods, the step of infecting cells infected with a virus infection may comprise administering the RNA virus vector to the subject. The RNA virus vector may be actively targeted to infected cells, or may travel via the blood or other biologic fluid to the site of the infection.

An RNA virus vector may be used for the treatment of a tumor. The RNA virus vector may be used for the treatment of a tumor of the head and neck. The RNA virus vector may be used for the treatment of a tumor of the esophagus. The RNA virus vector may be used for the treatment of a tumor of the lung. The RNA virus vector may be used for the treatment of a tumor of the breast. The RNA virus vector may be used for the treatment of a tumor of the pancreas. The RNA virus vector may be used for the treatment of a tumor of the kidney. The RNA virus vector may be used for the treatment of a tumor of the liver. The RNA virus vector may be used for the treatment of a tumor of the stomach. The RNA virus vector may be used for the treatment of a tumor of the colon. The RNA virus vector may be used for the treatment of a tumor of the ovary. The RNA virus vector may be used for the treatment of a tumor of the uterus. The RNA virus vector may be used for the treatment of a tumor of the prostate gland. The RNA virus vector may be used for the treatment of a tumor of the bladder. The RNA virus vector may be used for the treatment of a tumor of the blood.

An RNA virus vector may be used for the treatment of a viral infection. The RNA virus vector may be used for the treatment of a negative sense RNA virus infection. The RNA virus vector may be used for the treatment of an influenza Type A infection. The RNA virus vector may be used for the treatment of an influenza Type B infection. The RNA virus vector may be used for the treatment of an influenza Type C infection.

BRIEF DESCRIPTION OF THE DRAWINGS

FIGS. 1A through 1G show RIPK3 is required for IAV-induced lysis of MEFs and alveolar epithelial cells. FIG. 1A shows Ripk3+/+ and ripk3−/− MEFs were infected with the indicated strains of influenza virus at m.o.i.=2 or treated with TNF-α (50 ng/ml) in the presence of cycloheximide (250 ng/ml) and zVAD (50 µM) and cell viability was determined at 24 h.p.i. FIG. 1B shows photomicrographs of ripk3+/+ and ripk3−/− MEFs infected with PR8 or treated with TCZ for 24 hours. FIG. 1C shows FACS analysis of ripk3+/+ and ripk3−/− MEFs infected with PR8-GFP (m.o.i.=2). The y-axis shows side scatter. FIG. 1D shows Ripk3+/+ and ripk3−/− MEFs infected with PR8 were examined for virus replication by immunoblotting with antiserum raised against PR8 or a monoclonal antibody to NS1. A non-specific band detected in uninfected lysates by the anti-PR8 antiserum is indicated with an asterisk (*). Molecular weights (in kDa) are shown to the left. FIG. 1E shows kinetics of cell death after PR8 infection of ripk3+/+ and ripk3−/− MEFs at the indicated m.o.i.s. FIG. 1F shows Ripk3−/−(in the presence or absence of 50 µM zVAD), ripk3−/−casp8−/−, or ripk3−/−fadd−/− MEFs were infected with PR8 and cell viability was determined 36 h.p.i. FIG. 1G shows parental LET1 lung epithelial cells, or LET1 cells in which RIPK3 expression was ablated by CRISPR/Cas9 targeting of the sequence 5'-TGAGAACGTTCTGCTCCTGC-3' (SEQ ID NO:21) in the murine ripk3 gene, were infected with PR8 and viability (left) or progeny virion output (right) was determined 12 h.p.i. Inset. Immunoblot showing RIPK3 levels in these cells, with β-actin included as a loading control. Error bars represent mean+/−S.D. *p<0.05; **p<0.005.

FIG. 2A shows reconstitution of ripk3$^{-/-}$ MEFs with full-length murine RIPK3 restores susceptibility to IAV-induces cell death. Immortalized ripk3$^{-/-}$ MEFs were retrovirally reconstituted with full-length wild-type murine RIPK3, or with a control vector (Vec), infected with PR8 (m.o.i.=5) and examined for viability by Sytox Green positive (dead) cells were expressed as object counts per well. FIG. 2B shows DNA microarray analysis profiles expression patterns of TNF superfamily members in IAV-infected ripk3$^{-/-}$ MEFs. For this study, we used the PR8-ΔNS1 mutant, to avoid NS1-mediated suppression of RLR responses and allow full expression of the IAV-activated transcriptome in MEFs. From this analysis, only genes encoding deposited into GEO were identified; Series Number GSE80740. FIG. 2C shows Ripk3$^{-/-}$ MEFs were infected with PR8 (m.o.i.=2) in the presence or absence of neutralizing antibodies to murine TNF-α (5 µg/ml) or TRAIL-R2 (10 µg/ml), and viability was determined 36 h.p.i Equivalent amount of rabbit (rIgG) and goat (gIgG) immunoglobulins were used as controls. At these doses, anti-TNF-α and anti-TRAIL-R2 antibodies were able to robustly protect against apoptosis activated by the combinations of TNF-α (0.5 ng/mL) and SMAC mimetic (5 µM), or TRAIL (2 µg/ml) and cycloxehimide (CHX, 250 ng/ml), respectively. Error bars represent mean+/−S.D. NS=not significant; *p<0.005.

FIG. 4A shows wild type MEFs were infected with PR8 (m.o.i.=2) in the presence or absence of zVAD (25 µM), or treated with TCZ (right). Cells were lysed at the indicated time points, and anti-RIPK3 immunoprecipitates were examined for necrosome formation. IAV- or TCZ-activated RIPK3-RIPK1 necrosomes additionally contain FADD and MLKL. Whole-cell extract (5% input) was examined in parallel for RIPK1, RIPK3, FADD, MLKL, and IAV NS1 proteins. FIG. 4B shows time course of RIPK1/RIPK3 necrosome formation demonstrates that necrosome assembly succeeds virus replication. FIG. 4C shows RIPK3 immunoprecipitations performed on extracts from PR8-infected MEFs that were pre-treated with the indicated doses of Actinomycin D (ActD), cycloxehimide (CHX) or Nucleozin (Nuc), before infection indicates that the IAV-induced necrosome formation requires ongoing transcription, translation, and viral replication. FIG. 4D shows RIPK3 immunoprecipitations were performed on extracts from MEFs infected with PR8 or treated with TCZ in the presence or absence of the indicated doses of the RIPK3 kinase inhibitors GSK'872 or GSK'843 (left) or the RIPK1 kinase inhibitors GSK'963 or GSK'481 (right). FIG. 4E shows primary early passage wild-type (WT) and the indicated knock-out MEFs were infected with PR8 in the presence of zVAD (50 µM) with or without the RIPK3 inhibitor GSK'843 (5 µM). As controls, ripk3−/− MEFs retrovirally reconstituted with full-length murine RIPK3, or with an empty vector, were used. Viability was determined 24 h.p.i. Error bars represent mean+/−S.D. **p<0.005.

FIGS. 5A through 5E show RIPK3 activates parallel pathways of necroptosis and apoptosis upon IAV infection. FIG. 5A shows Ripk3+/+ MEFs were infected with PR8 (m.o.i.=2) in the presence or absence of zVAD (50 µM), RIPK1 kinase inhibitors (GSK'963 (5 µM), GSK'481 (5 µM), and Nec-1 (50 µM)), or RIPK3 kinase inhibitors (GSK'872 (5 µM), and GSK'843 (5 µM)) and cell viability was determined 24 h.p.i. TCZ-treated wild-type MEFs exposed to the same doses of RIPK1 or RIPK3 inhibitors were used as controls. FIG. 5B shows LET1 lung epithelial cells were infected with PR8 in the presence or absence of zVAD (50 µM) or GSK'843 (5 µM), and viability was determined 12 h.p.i. LET1 cells treated with TCZ were included as controls. FIG. 5C shows human HT-29 cells were infected with PR8 (m.o.i.=5) in the presence or absence zVAD (50 µM) or GSK'840 (3 µM) and viability was determined 14 h.p.i. HT-29 cells treated with human TNF-α (0.5 ng/mL), SMAC mimetic LCL161 (5 µM), and zVAD (50 µM) were included as controls (TSZ). FIG. 5D shows kinetics of cell death after wild-type or UV-inactivated (PR8 UV) PR8 infection in ripk3+/+ MEFs in the presence or absence of caspase inhibitor QvD (40 µM) or GSK'872 (5 µM) was analyzed for up to 36 h.p.i. Cell death was determined Sytox Green uptake, and quantified as number of Sytox Green positive cells over time. FIG. 5E shows wild-type MEFs infected with PR8 in the presence of GSK'843 (5 µM), zVAD (50 µM) or both inhibitors together were examined for phosphorylated MLKL or cleaved caspase 8 by immunoblot analysis at the indicated times p.i. Error bars represent mean+/−S.D. *p<0.05; **p<0.005.

FIG. 7A shows wild-type MEFs were infected with PR8-GFP (m.o.i.=2) for 18 hours and sorted by GFP-positive and GFP-negative populations, representing cells harboring actively-replicating virus and cells without detectable virus replication, respectively. FIG. 7B shows GFP-positive and GFP-negative cells were examined for phosphorylation of MLKL and cleavage of caspase 8 by immunoblot analysis.

FIG. 8A shows wild type, fadd−/−, mlkl−/−, and mlkl−/−fadd−/− double knock-out MEFs were infected with PR8 in the presence or absence of pan-caspase inhibitor zVAD (50 µM), the caspase 8 inhibitor zIETD (50 µM) and/or 5 µM of RIPK3 kinase inhibitors (GSK'872 and GSK'843). Cell viability was determined 24 h.p.i. FIG. 8B shows wild type, fadd−/−, mlkl−/−, mlkl−/−fadd−/−, and ripk3−/− MEFs were infected with PR8 for 16 hours, and examined for phosphorylated MLKL or cleaved caspase 8 by immunoblot analysis. Error bars represent mean+/−S.D. *p<0.05; **p<0.005.

FIG. 9A shows zIETD is a weaker inhibitor of IAV-activated apoptosis than zVAD. Mlkl$^{-/-}$ MEFs were infected with PR8 in the presence or absence of zVAD (50 µM), zIETD (50 µM) added once, or zIETD added once and supplemented at 12 h.p.i (two last bars), and cell viability was determined 24 h.p.i. FIG. 9B shows kinetics of cell death after PR8 (m.o.i.=5) infection of ripk3$^{+/+}$, ripk3$^{-/-}$, and mlkl$^{-/-}$ fadd$^{-/-}$ double knock-out MEFs. FIG. 9C shows wild types (ripk3$^{+/+}$) and mlkl$^{-/-}$ fadd$^{-/-}$ double-knockout MEFs infected with PR8 (m.o.i.=5) for the indicated times and examined for virus replication by immunoblotting with antiserum to PR8 or antibodies to NS1. A non-specific band detected in uninfected lysates by the anti-PR8 antiserum is indicated with an asterisk (*). Molecular weights (in kDa) are shown to the left. FIG. 9D shows Mlkl$^{-/-}$, ripk3$^{-/-}$, and ripk3$^{-/-}$ mlkl$^{-/-}$ MEFS were infected with PR* (m.o.i.=5) in the presence or absence of zVAD (50 µM) and cell viability was determined at 24 and 36 h.p.i., to evaluate PIPK3-dependent early apoptosis and RIPK3-independent late apoptosis, respectively. Both early and late apoptosis proceed normally in cells with MLKL-deficiency. Error bars represent mean+/−S.D. NS=not significant; *p<0.05; p<0.005; *p<0.0005.

FIG. 10A shows Ripk1−/−, ripk1k45/a/k45a, and ripk1d138n/d138n MEFs were infected with PR8 (m.o.i.=2) in the presence or absence of zVAD (50 µM) or 5 µM of the RIPK3 inhibitors GSK'872 or GSK'843, and viability was determined 24 h.p.i. FIG. 10B shows Ripk1−/−, ripk1k45/a/k45a, and ripk1d138n/d138n MEFs were treated with TCZ and viability was determined 24 h.p.i. FIG. 10C shows Ripk1−/−, ripk1d138n/d138n (referred to as ripk1kd/kd), and ripk3−/− MEFs were infected with PR8 and examined for phosphorylated MLKL or cleaved caspase 8 by immunoblot analysis at the indicated times p.i. FIG. 10D shows Ripk1+/+ and ripk1−/− MEFs were infected with PR8 in the presence of zVAD (25 µM). Cells were lysed at the indicated time points, and RIPK3-immunoprecipitated lysates were examined for presence of FADD. Error bars represent mean+/−S.D. *p<0.05; p<0.005; *p<0.0005.

FIG. 11A shows survival analysis of age- and sex-matched ripk3+/+ and ripk3−/− mice infected with PR8 (4000 EID50/mouse by i.n.). FIG. 11B shows survival analysis of age- and sex-matched mlkl+/+, mlkl−/−, and mlkl−/− fadd−/− double knock-out mice with PR8 (4000 EID50/mouse by i.n.). Data are pooled from two independent experiments. FIG. 11C shows virus titers were determined on infected lungs 3 or 9 d.p.i. by plaque assay (n=3-5). FIG. 11D shows paraffin embedded sections of ripk3+/+ and ripk3−/− mouse lungs 6 d.p.i. were stained with anti-IAV antibodies, and slides were scanned and virus spread was quantified using Aperio ImageScope. Representative images of anti-IAV stained 11 ripk3+/+ (top) and 10 ripk3−/− (bottom) lungs are shown to the left, and quantification of virus spread from lungs of individual mice are shown to the right. FIG. 11E shows representative images of H&E-stained 11 ripk3+/+ and 10 ripk3−/− lungs 6 d.p.i at two magnifications reveal severe edema and alveolar damage in ripk3−/− pulmonary tissue (left). Quantification of alveolar fibrin deposition from lungs of individual mice is shown to the right. The extent and severity of pulmonary damage was determined from blinded sections examined by a pathologist and scored for the distribution of alveolar fibrin deposition on a severity scale of 1-5. These scores were converted to a semi-quantitative scale). FIG. 11F shows representative images of CD3+ staining in 11 ripk3+/+ and 10 ripk3−/− lungs 6 d.p.i. Quantification of CD3+ staining from lungs of individual mice are shown to the right. FIG. 11G shows quantification of frequencies of IAV-specific (DbPA224) CD8+ T cells and percentage of IAV PA224 peptide-stimulated poly-functional IFN-γ+TNF-α+CD8+ T cells in BAL fluid from ripk3+/+ and ripk3−/− animals (n=3-5) at 9 d.p.i. The low pathogenic HKx31 reassortant of PR8 was used in these experiments to avoid 9 d.p.i. lethality effects seen with PR8. Error bars represent mean+/−S.D. *p<0.05; ***p<0.0005.

FIG. 12A shows wild type (WT) or zbp1$^{-/-}$ MEFs from two separately-maintained colonies (MEF 1 and MEF 2) were infected with PR8 (MOI=2 and 5), or treated with the combination of TNF-α (50 ng/ml)+cycloheximide (250 ng/ml)+zVAD (50 μM) (TCZ) and cell viability was determined 24 h.p.i. FIG. 12B shows photomicrographs of WT and zbp1$^{-/-}$ MEFs infected with PR8 (MOI=2) or treated with TCZ for 24 hours. FIG. 12C shows FACS analysis of WT and zbp1$^{-/-}$ MEFs infected with PR8-GFP (MOI=2) for 18 hours. The y-axis shows side scatter. FIG. 12D shows lysates from WT and zbp1$^{-/-}$ MEFs infected with PR8 (MOI=2) for the indicated times were examined for expression of NS1 and DAI. β-actin was used as a loading control. FIG. 12E shows immortalized zbp1$^{-/-}$ MEFs reconstituted with empty vector (EV), wild-type full-length murine DAI (DAI), or murine DAI with mutant RHIM domain (amino acids 192-195 IQIG to AAAA) (DAI mutRHIM) were infected with PR8 (MOI=2) and cell viability was determined 24 h.p.i. Expression of WT or mutant DAI in these cells is shown to the right. FIG. 12F shows WT MEFs in which DAI expression was ablated by CRISPR/Cas9 targeting of the sequences 5'-TCTGGAGTCACACAAGAGTCCCCT-3' (CRISPR 1) (SEQ ID NO:16) or 5'-GCTCAGTACATCTACATGGACAAGTCCTTG-3' (CRISPR 2) (SEQ ID NO:17) in the murine zbp1 gene were infected with PR8 (MOI=2) and cell viability was determined 24 h.p.i. Ablation of DAI expression was confirmed by immunoblotting (right). FIG. 13G shows LET1 cells in which DAI expression was ablated by CRISPR/Cas9 targeting of murine zbp1 gene using sequences shown in 12E, were infected with PR8 (MOI=2) and cell viability was determined 12 h.p.i. In parallel, progeny virion output from these cells was determined 30 h.p.i. (right). Ablation of DAI expression was confirmed by immunoblotting.

FIG. 13A shows wild-type MEFs were infected with PR8 (MOI=2) and anti-RIPK3 immunoprecipitates were examined for DAI, RIPK1 and MLKL at the indicated times p.i. FIG. 13B shows wild-type (WT), zbp1$^{-/-}$, and ripk3$^{-/-}$ MEFs infected with PR8 (MOI=2) (MOI=2) and examined for phosphorylated (p) MLKL and cleaved caspase-8 (CC8 p18). In parallel, wild-type (WT), zbp1$^{-/-}$, and ripk3$^{-/-}$ MEFs were treated with TCZ hours and phosphorylated MLKL. FIG. 13C shows Zbp1$^{-/-}$ MEFs reconstituted with empty vector (Vec), full-length murine DAI (DAI), or DAI with a mutated RHIM domain (DAI mutRHIM) were infected with PR8 (MOI=2) for 14 or 18 hours and examined for phosphorylated MLKL and cleaved caspase-8. In parallel, reconstituted cells were treated with TCZ and examined for expression of phosphorylated p MLKL. FIG. 13D shows anti-RIPK3 immunoprecitates were examined from zbp1$^{-/-}$ MEFs reconstituted with full-length murine DAI (DAI) or DAI with a mutated RHIM domain (DAI mutRHIM) infected with PR8 (MOI=2) for DAI and RIPK3. Whole-cell extract (5% input) was examined in parallel for RIPK3, DAI and IAV NS1 proteins. FIG. 13E shows kinetics of cell death after PR8 infection (MOI=2) of WT, zbp1$^{-/-}$, ripk3$^{-/-}$, ripk1$^{-/-}$ ripk3$^{-/-}$ double knockout and mlkl$^{-/-}$ fadd$^{-/-}$ double knockout MEFs. FIG. 13F shows whole cell extracts from WT, zbp1$^{-/-}$, ripk3$^{-/-}$ and ripk1$^{-/-}$ ripk3$^{-/-}$ double knockout MEFs infected with PR8 at MOI=2 or MOI=5 were examined for expression of cleaved caspase-8 (CC8).

FIG. 14A shows a schematic of mutants used in studies (see, FIG. 14B) Zbp1$^{-/-}$ MEFs reconstituted with WT DAI or with the indicated mutants were infected with PR8 (MOI=2) and cell viability was measured 24 h.p.i. FIG. 14C shows Zbp1$^{-/-}$ MEFs reconstituted with WT DAI or with the indicated mutants were infected with PR8 (MOI=2, top) or TCZ (bottom) and examined for phosphorylated MLKL. FIG. 14D shows similarity of Zα1 and Zα2 domains bound to either Z-DNA and Z-RNA substrates. The known structures of human DAI-Zα2 bound to Z-DNA (PDB code 3EYI, first panel) and ADAR1 Zα1 bound to Z-RNA (PDB code 2GXB, second panel). Homology model of murine DAI Zα2 bound to Z-RNA is shown in the third panel, with the location of N122 and Y126 depicted. A superposition of the mDAIZα2 bound to zRNA compared to the known structure of hDAIZα2 bound to zDNA. The conserved N and Y residues of the mDAIZα2:Z-RNA complex are shown as ball-and-stick representation, while the corresponding residues in hDAI-Zα2:zDNA complex are shown as sticks. FIG. 14E shows Integrated Genome Viewer representation of captured sequencing reads of negative polarity from FLAG-immunoprecipitations of PR8-infected 293T cells expressing either FLAG-DAI (top) or FLAG-RIG-I (bottom). Horizontal bars represent a single 150 nt read and the position where it aligned relative to each IAV gene segment, depicted at the top of each sample. The histogram is a synopsis of total coverage in any given position.

FIGS. 15A and 15B show survival and weight loss, respectively, analysis of age- and sex-matched WT and zbp1$^{-/-}$ mice infected with PR8 (1000 EID$_{50}$/mouse i.n.). Dead mice are represented by black circles. FIG. 15C shows virus titers from WT and zbp1$^{-/-}$ mice infected with PR8 (750 EID$_{50}$/mouse i.n.) were determined by plaque assay (n=3-5 mice/condition). FIG. 15D shows representative images of lungs from WT and zbp1$^{-/-}$ mice stained with anti-IAV antibodies 9 d.p.i. FIG. 15E shows model of DAI-induced cell death following IAV infection. DAI dimers sense IAV vRNA in a manner requiring the Zα2 domain, leading to RHIM-based interaction with, and activation of, RIPK3. Downstream of RIPK3, parallel pathways of MLKL-driven necroptosis and RIPK1/

FADD/caspase-8-mediated apoptosis co-operate to eliminate the infected cell. DAI also activates apoptosis independently of RIPK3, via a putative RIPK1/FADD-caspase-8 axis.

Figure 16A:
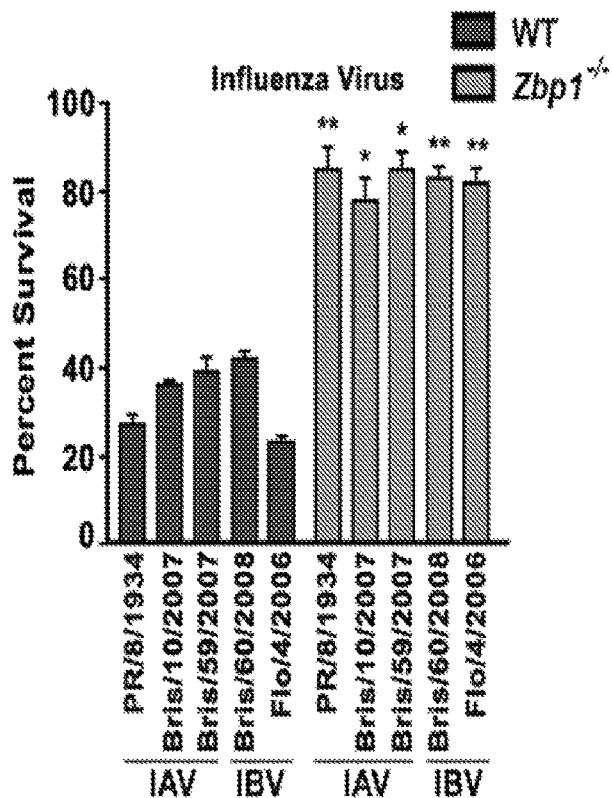
Figure 16B:
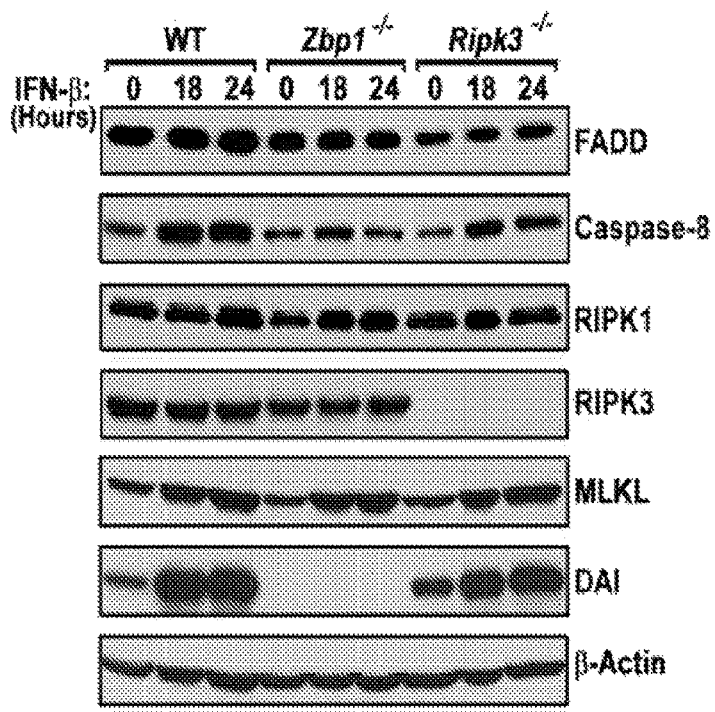
Figure 16C:
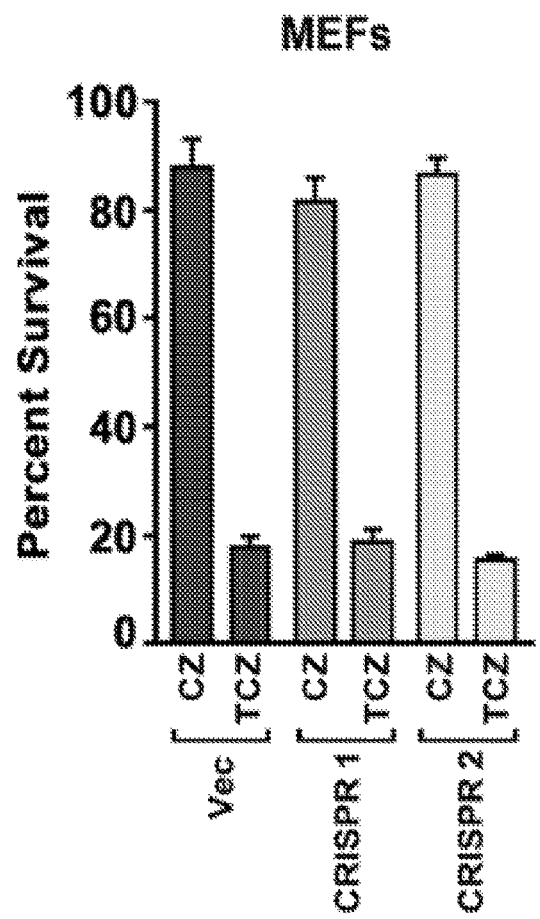
Figure 16D:
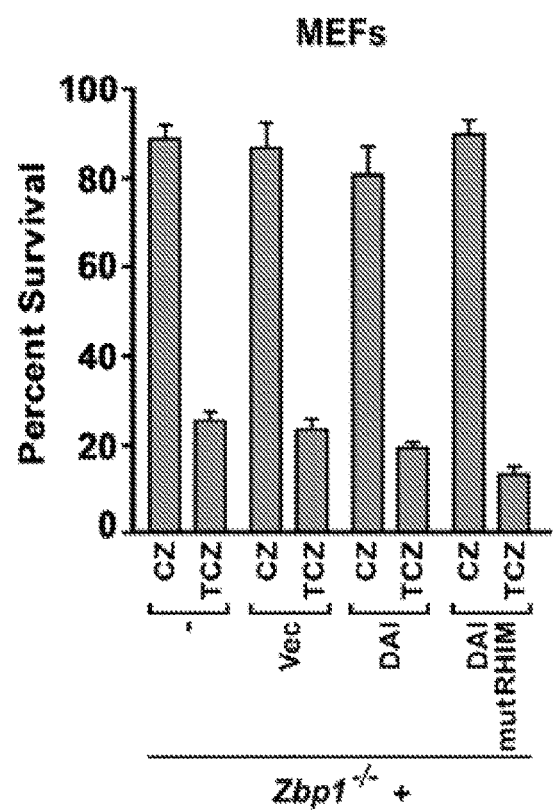
Figure 16E:
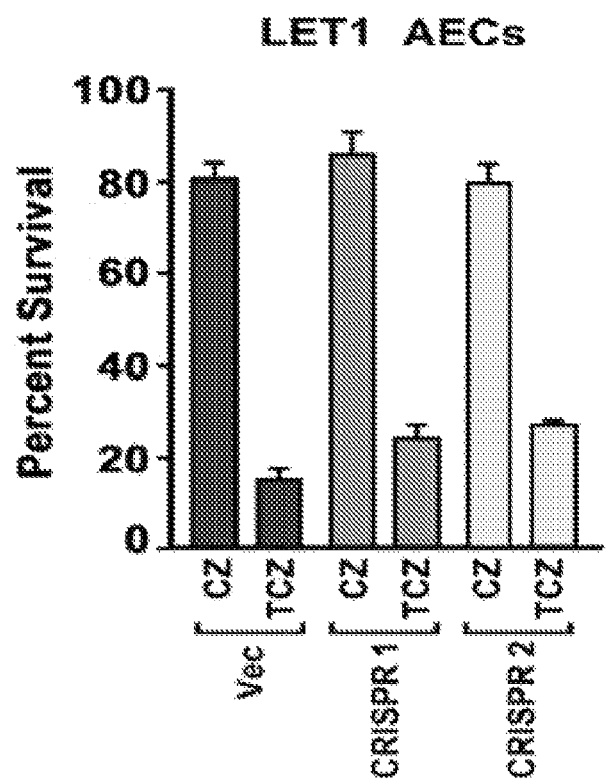

FIGS. 16A through 16E show DAI is selectively required for IAV- and IBV induced cell death in MEFs and airway epithelial cells. FIG. 16A shows wild-type (WT) or zbp1$^{-/-}$ MEFs were infected with IAV strains PR8, Brisbane/10/2007, Brisbane/59/2007, and IBV strains Brisbane/60/2008 and Florida/4/2006 (MOI=2) and cell viability was measured 24 h.p.i. FIG. 16B shows whole cell extracts from WT, zbp1$^{-/-}$ and ripk3$^{-/-}$ MEFs treated with IFN-b for 18 or 24 hours were examined for FADD, Caspase-8, RIPK1, RIPK3, MLKL and DAI. Beta-actin was used as a loading control. FIG. 16C shows WT MEFs or WT MEFs in which DAI expression was ablated by CRISPR/Cas9 targeting of the sequences CRISPR 1 CRISPR 2 in the murine zbp1 gene were treated with CZ or TCZ and cell viability was measured 24 h.p.i. FIG. 16D shows Zbp1$^{-/-}$ MEFs reconstituted with empty vector (Vec), full length murine DAI (DAI) and full-length DAI with a mutated RHIM domain (DAI mutRHIM) were treated with CZ or TCZ and cell viability was measured 24 h.p.i. FIG. 16E shows LET1 cells in which DAI expression was ablated by CRISPR/Cas9 targeting of murine zbp1 gene using sequences described in C were treated with CZ or TCZ and cell viability was measured 24 h.p.i.

Figure 17:
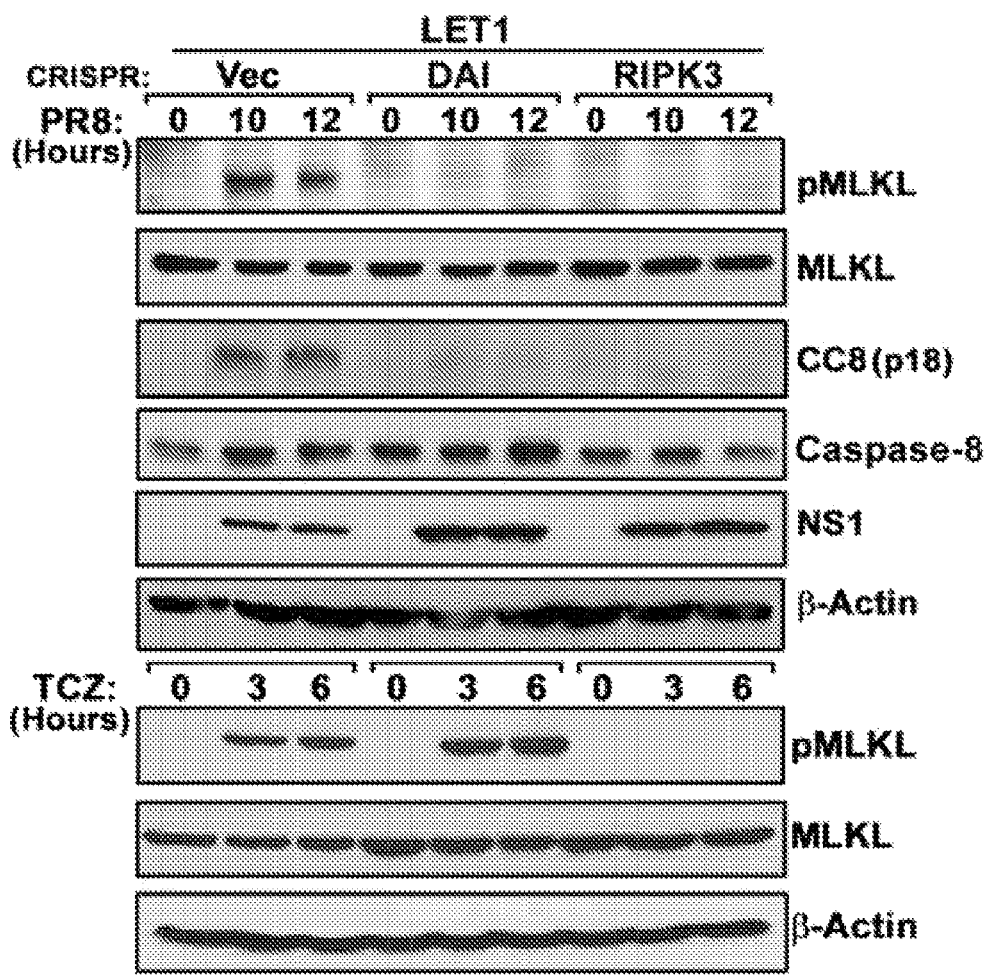

FIG. 17 shows DAI is required for activation of RIPK3 in LET1 AECs. Whole cell extracts of LET1 cells expressing empty vector (Vec), or LET1 cells in which with a zbp1 or ripk3 were deleted by CRISPR/Cas9 targeting were infected with PR8 (MOI=2, top) or TCZ (bottom) were examined for phosphorylated MLKL and cleaved caspase-8.

Figure 18A:
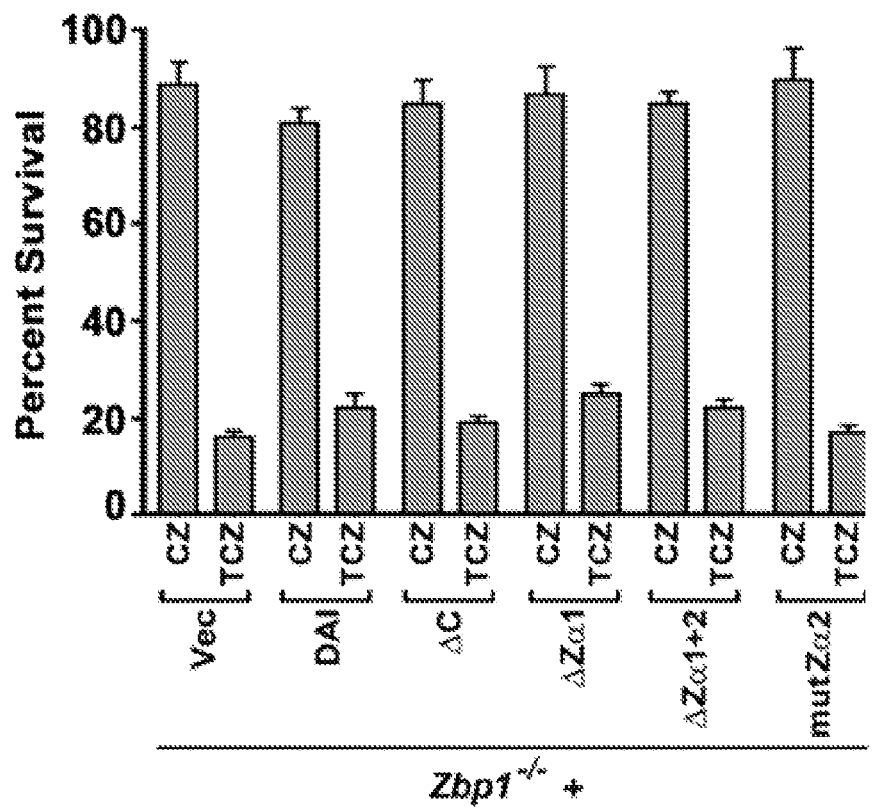
Figure 18B:
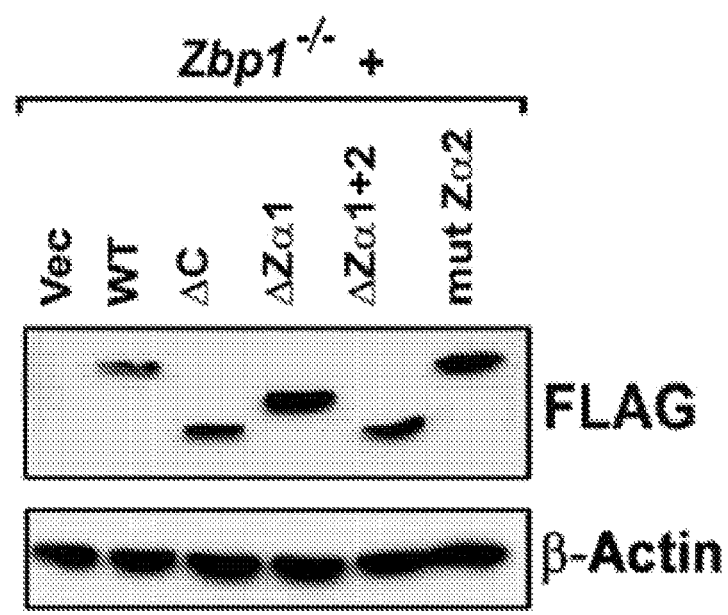
Figure 18C:
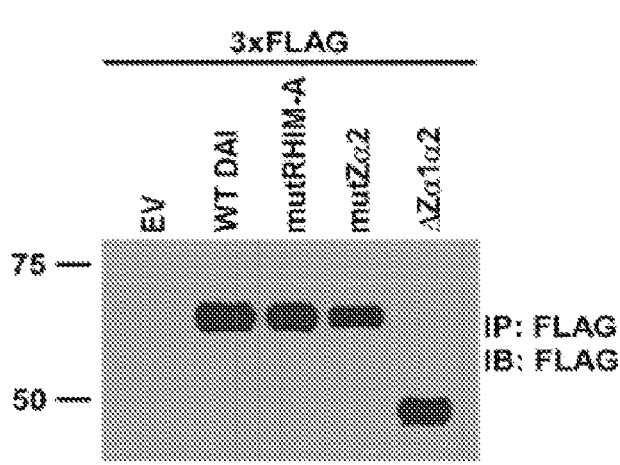
Figure 18D:
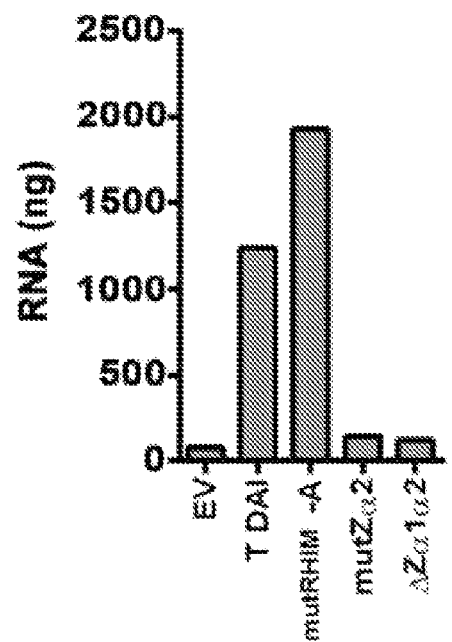
Figure 18E:
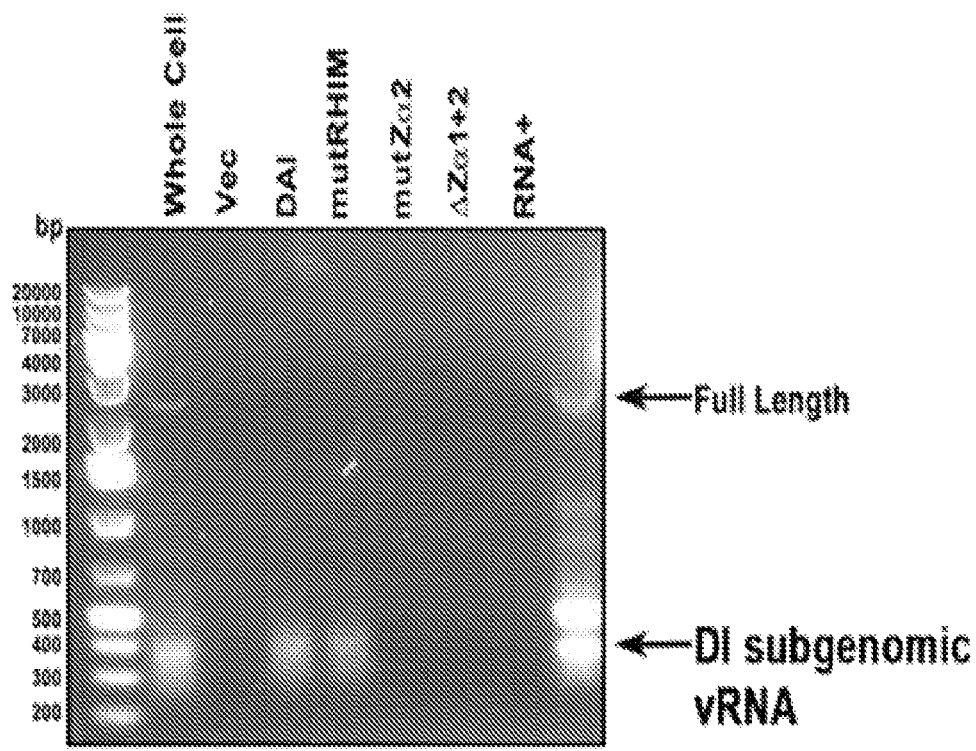

FIGS. 18A through 18E show DAI senses IAV RNA in a manner requiring its Za2 domain. FIG. 18A shows kinetics of cell death in PR8-infected immortalized zbp1$^{-/-}$ MEFs reconstituted with WT DAI or its mutants. FIG. 18B shows expression levels of FLAG-tagged constructs in immortalized zbp1$^{-/-}$ MEFs reconstituted with WT DAI or its mutants. FIG. 18C shows expression of FLAG-tagged DAI constructs in FLAG immunoprecipitates from IAV-infected 293T cells 12 h.p.i. FIG. 18D shows quantification of RNA eluted from anti-FLAG immunoprecipitate of the indicated FLAG-DAI constructs from PR8-infected 293T cells 12 h.p.i. FIG. 18E shows PCR detection of PB2 vRNA in eluted RNA from FLAG-DAI immunoprecipitates, using primers specific for the vRNA ends of the PB2 segment. RNA+: A549 cells infected (MOI=3) with PR8.

DESCRIPTION OF EMBODIMENTS

Various terms relating to embodiments of the present disclosure are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

A molecule such as a polynucleotide has been "isolated" if it has been removed from its natural environment and/or altered by the hand of a human being.

Nucleic acid molecules include any chain of at least two nucleotides, which may be unmodified or modified RNA or DNA, hybrids of RNA and DNA, and may be single, double, or triple stranded.

Inhibiting includes, but is not limited to, interfering with, reducing, decreasing, blocking, preventing, delaying, inactivating, desensitizing, stopping, knocking down (e.g., knockdown), and/or downregulating the biologic activity or expression of a protein or biochemical pathway.

The terms "subject" and "patient" are used interchangeably. A subject may be any animal, such as a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). In some embodiments, the mammal is a human, such as a MIBC patient.

It has been observed in accordance with the present disclosure that the protein DAI (also known as ZBP1/DLM-1) was required for RIPK3 activation and cell death in IAV-infected murine cells. It was observed that DAI senses IAV RNA via its Zα2 domain and, in turn, participates in activation of RIPK3. DAI also mediates RIPK3-independent apoptosis, by activating a RIPK1-FADD-caspase 8 pathway. These findings identify DAI as a mediator of IAV-driven cell death, and implicate this protein as a new sensor of RNA viruses. Thus, while DAI is clearly important in host defense against DNA viruses, it also participates in the immune response to RNA viruses.

Influenza virus is a negative sense RNA virus. The virus encodes an RNA polymerase (RNA-dependent RNA polymerase) that constructs a positive sense template of viral RNA, which effectively serves as an mRNA for translation of viral proteins during an infection. Without intending to be limited to any particular theory or mechanism of action, it is believed that during construction of the plus sense RNA template by the virus RNA polymerase, at least a transient double stranded RNA (dsRNA) molecule is produced (including the original negative sense strand and the newly synthesized positive sense strand). Without intending to be limited to any particular theory or mechanism of action, it is further believed that this dsRNA molecule interacts with the DAI protein (e.g., at the Zα2 domain that senses double stranded DNA), thereby activating DAI, which in turn activates RIPK3 to induce either or both of RIPK3-dependent apoptosis and RIPK3-independent necroptosis via the necrosome complex. Nevertheless, it is possible that single stranded RNA can interact with and activate DAI. Accordingly, the present disclosure features compositions and methods that take advantage of the therapeutic capacity of DAI to recognize RNA, and facilitate cell death by way of apoptosis and/or necroptosis, with necroptosis further facilitating an immune response, including an inflammatory response.

In some embodiments, the present disclosure provides virus vectors, comprising a gene encoding the DNA-dependent activator of interferon-regulatory factors (DAI) protein. In some embodiments, the present disclosure provides a virus vector, comprising a gene encoding the DAI protein and a gene encoding the receptor-interacting serine/threonine-protein kinase 3 (RIPK3) protein. In some embodiments, the present disclosure comprises a virus vector comprising a gene encoding the RIPK3 protein, but not a gene encoding the DAI protein. The virus vector may be a DNA virus or an RNA virus. An RNA virus vector may be a retrovirus vector, a positive sense RNA virus, or a negative sense RNA virus, and the RNA may comprise single stranded RNA. Negative sense RNA comprises a nucleic acid sequence that is complementary to the mRNA that it encodes, and which is produced by RNA-dependent RNA polymerase. Positive sense RNA is similar to mRNA and may be translated accordingly.

Retroviruses suitable for use as a vector include, but are not limited to a Lentivirus. Positive sense RNA viruses suitable for use as a vector include, but are not limited to, the Kunjin virus, Polio virus, Semliki Forest virus, Venezuelan Equine Encephalitis virus, and Sinbis virus. Negative sense RNA viruses suitable use as a vector include, but are not limited to, the Rabies virus, Influenza virus, Vesicular Stomatitis virus, Respiratory Syncytial virus, Sendai virus, Measles virus, New Castle Disease virus, or Simian Virus 5 (SV5) virus. Negative sense RNA viruses are suitable insofar as their production of dsRNA induces DAI to sense the presence of dsRNA and facilitate RIPK3 and necrosome-mediated cell death. In any case, it may be desired that the virus vector is in a live, but attenuated form, such that the virus vector does not substantially induce untoward effects in the host during use as a therapeutic agent, for example, the virus's normal virulence factors are removed or altered/lessened such that the virus itself does not substantially cause illness in the host during use.

In some embodiments, the DAI protein encoded by the gene is the human DAI protein. The gene may be in DNA or RNA form, and may comprise the sense sequence or antisense sequence form of the gene. In some embodiments, the gene encodes a DAI protein having the amino acid sequence of SEQ ID NO:13. In some embodiments, the gene may comprise the nucleic acid sequence of SEQ ID NO:1 (DNA) or SEQ ID NO:4 (RNA), or may comprise the complementary nucleic acid sequence thereof (e.g., SEQ ID NO:7 (DNA) or SEQ ID NO:10 (RNA)).

In some embodiments, the RIPK3 protein encoded by the gene is the human RIPK3 protein. The gene may be in DNA or RNA form, and may comprise the sense sequence or antisense sequence form of the gene. In some embodiments, the gene encodes a RIPK3 protein having the amino acid sequence of SEQ ID NO:14. In some embodiments, the gene may comprise the nucleic acid sequence of SEQ ID NO:2 (DNA) or SEQ ID NO:5 (RNA), or may comprise the complementary nucleic acid sequence thereof (e.g., SEQ ID NO:8 (DNA) or SEQ ID NO:11 (RNA)).

In some embodiments, the virus vector further comprises a gene encoding the human mixed lineage kinase domain-like (MLKL) protein. The gene may be in DNA or RNA form, and may comprise the sense sequence or antisense sequence form of the gene. In some embodiments, the gene encodes a MLKL protein having the amino acid sequence of SEQ ID NO:15. In some embodiments, the gene may comprise the nucleic acid sequence of SEQ ID NO:3 (DNA) or SEQ ID NO:6 (RNA), or may comprise the complementary nucleic acid sequence thereof (e.g., SEQ ID NO:9 (DNA) or SEQ ID NO:12 (RNA)).

In some embodiments, the virus vector further comprises a gene encoding a caspase inhibitor protein. The caspase inhibitor protein may be a viral caspase inhibitor protein. In some embodiments, the caspase inhibitor protein inhibits caspase 8. Non-limiting examples of viral caspase inhibitors that may be encoded by such a gene include the viral inhibitor of caspase 8-induced apoptosis (vICA) protein, cytokine response modifier A (CrmA), and Vaccinia virus serpin SPI-2/B13R. The gene may be in DNA or RNA form, and may comprise the sense sequence or antisense sequence form of the gene. In some embodiments, for example, where the virus vector comprises an influenza virus (e.g., Type A), the virus may activate DAI-RIPK3 cell death without a need for concurrent caspase inhibition.

In some embodiments, the virus vector further comprises a surface (e.g., envelope) protein or glycoprotein that facilitates tropism between the virus vector and the target cells or tissue. In some embodiments, the virus vector has broad tropism such that the virus vector is capable of infecting a wide variety of host cells. In some embodiments, the virus may be engineered to express particular proteins or glycoproteins to extend the natural tropism of the virus vector to additional cell types, or to otherwise facilitate viral interaction with host cell receptors toward enhancing infection efficiency. Thus, the virus vector may be targeted to particular tissues in order to achieve tissue tropism, for example, to a tumor. Targeting may comprise pseudotyping, for example, where cell surface glycoproteins on the virus are added, modified, or replaced to alter specificity for the virus vector's receptor(s) and, hence, permit the virus to different cell types and tissues than it otherwise would in an unaltered state.

In some embodiments, the virus vector is capable of targeting, binding to, and infecting tissue or cells that are infected with another, pathogenic virus, or tissue or cells that are cancerous. In some embodiments, the virus vector is capable of targeting, binding to, and infecting tissue or cells that are infected with a pathogenic strain of an influenza virus (e.g., Type A, Type B, or Type C influenza virus). The pathogenic influenza virus may comprise a seasonal or pandemic strain of the influenza virus. In some embodiments, the virus vector is capable of targeting, binding to, and infecting cancerous or precancerous tissue or cells. The cancerous or precancerous tissue or cells may comprise any tissue or cells capable of expressing the DAI and RIPK3 proteins encoded by the virus vector, as well as capable of expressing the MLKL protein and/or caspase inhibitor protein if such are encoded by the virus vector. The cancerous or precancerous tissue may be deficient in endogenous DAI protein.

Thus, the virus vectors may be used therapeutically to treat viral infections or to treat tumors. In some embodiments, methods for treating a tumor comprise infecting cells of the tumor with any of the virus vectors described or exemplified herein. The cells may be infected by administering the virus vector to the tumor, e.g., by directly contacting the tumor cells with the virus vector, or by administering the virus vector to the tumor patient, e.g., to the blood, followed by delivery of the vector to the tumor by the body. Delivery to the tumor may be targeted, and/or may be facilitated.

The tumor may be any tumor that includes the biochemical machinery capable of causing RIPK3-mediated cell death. The tumor may be a tumor of the head and neck, esophagus, lung, breast, pancreas, kidney, liver, stomach, colon, ovary, uterus, prostate gland, bladder, or blood. The tumor may have reduced expression or no expression of endogenous RIPK3.

In some embodiments, methods for treating a viral infection comprise infecting cells infected with a virus with any of the virus vectors described or exemplified herein. The virally-infected cells may be further infected with the virus vector by administering the virus vector to the cells, e.g., by directly contacting the virally-infected cells with the virus vector, or by administering the virus vector to the virally-infected patient, e.g., to the blood, followed by delivery of the vector to the site of the infection by the body. Delivery to the site of the virus infection may be targeted, and/or may be facilitated. In some embodiments, the virus infection to be treated is a pathogenic virus infection, for example, an influenza virus infection. Thus, for example, in some embodiments, virus vectors based on the influenza virus may be used to treat cells that are infected with a strain of influenza virus, including influenza type A, type B, or type C.

Any virus vector described or exemplified herein may be used in the manufacture of a medicament, for example, in the manufacture of a medicament for the treatment of a virus infection such as an influenza virus infection (e.g., influenza type A infection, influenza type B infection, or influenza type C infection). The virus vectors may also be used in the manufacture of a medicament for the treatment of a tumor such as a tumor of the head and neck, esophagus, lung, breast, pancreas, kidney, liver, stomach, colon, ovary, uterus, prostate gland, bladder, or blood. Thus, a virus vector may be used in the treatment of a viral infection, or may be used in the treatment of a tumor.

The combination of DAI and RIPK3 may be used therapeutically to kill tumor cells or virally-infected cells. Nevertheless, the cell death induced by DAI and RIPK3 may be undesired in some contexts. For example, without intending to be limited to any particular theory or mechanism of action, it is believed that the activity of DAI and/or RIPK3 may, in some cases such as pandemic strains of the influenza virus may contributes to the virulence of the virus. Thus, it is believed that inhibiting DAI or RIPK3-induced cell death may benefit patients infected with a pandemic or virulent strain of the influenza virus. In such cases, it is believed that keeping host-infected cells alive longer will reduce the virulence of the virus. Accordingly, a patient infected with a pandemic or virulent strain of virus such as a pandemic strain of the influenza virus (type A, type B, or type C) may be treated by inhibiting one or more of DAI or RIPK3 in virally-infected cells. Thus, a subject infected with a pandemic strain of the influenza virus may be treated by administering to the subject an effective amount of a DAI or a RIPK3 inhibitor. The inhibitor may be potaninib or may be debrafenib, or any derivative thereof that inhibits DAI or RIPK3. Accordingly, potaninib or debrafenib, or derivative thereof, may be used in the treatment of influenza virus infection, particularly for a pandemic or virulent strain of influenza virus, where inhibition of necrosis may be desired.

The following representative embodiments are presented:

Embodiment 1 An RNA virus vector, comprising an RNA virus comprising a gene encoding the human DNA-dependent activator of interferon-regulatory factors (DAI) protein and a gene encoding the human receptor-interacting serine/threonine-protein kinase 3 (RIPK3) protein.

Embodiment 2 The RNA virus vector according to embodiment 1, wherein the RNA virus is a positive sense RNA virus.

Embodiment 3 The RNA virus vector according to embodiment 1 or embodiment 2, wherein the positive sense RNA virus is an attenuated Kunjin virus, Polio virus, Semliki Forest virus, Venezuelan Equine Encephalitis virus, or Sinbis virus.

Embodiment 4 The RNA virus vector according to embodiment 1, wherein the RNA virus is a negative sense RNA virus.

Embodiment 5 The RNA virus vector according to embodiment 1 or embodiment 4, wherein the negative sense RNA virus is an attenuated Rabies virus, Influenza virus, Vesicular Stomatitis virus, Respiratory Syncytial virus, Sendai virus, Measles virus, New Castle Disease virus, or Simian Virus 5 (SV5) virus.

Embodiment 6 The RNA virus vector according to embodiment 1, wherein the RNA virus is a retrovirus.

Embodiment 7 The RNA virus vector according to embodiment 1 or embodiment 6, wherein the retrovirus is an attenuated Lentivirus.

Embodiment 8 The RNA virus vector according to any one of embodiments 1 to 7, wherein the gene encoding the human DAI protein comprises a nucleic acid sequence encoding the amino acid sequence of SEQ ID NO:13.

Embodiment 9 The RNA virus vector according to any one of embodiments 1 to 8, wherein the gene encoding the human DAI protein comprises RNA.

Embodiment 10 The RNA virus vector according to any one of embodiments 1 to 9, wherein the gene encoding the human DAI protein comprises a negative sense RNA.

Embodiment 11 The RNA virus vector according to any one of embodiment 1 to 7, wherein the gene encoding the human DAI protein comprises the nucleic acid sequence of SEQ ID NO:1, SEQ ID NO:4, or the complement of SEQ ID NO:1 or SEQ ID NO:4.

Embodiment 12 The RNA virus vector according to any one of embodiments 1 to 11, wherein the gene encoding the human RIPK3 protein comprises a nucleic acid sequence encoding the amino acid sequence of SEQ ID NO:14.

Embodiment 13 The RNA virus vector according to any one of embodiments 1 to 12, wherein the gene encoding the human RIPK3 protein comprises RNA.

Embodiment 14 The RNA virus vector according to any one of embodiments 1 to 13, wherein the gene encoding the human RIPK3 protein comprises a negative sense RNA.

Embodiment 15 The RNA virus vector according to any one of embodiments 1 to 11, wherein the gene encoding the human RIPK3 protein comprises the nucleic acid sequence of SEQ ID NO:2, SEQ ID NO:5, or the complement of SEQ ID NO:2 or SEQ ID NO:5.

Embodiment 16 The RNA virus vector according to any one of embodiments 1 to 15, wherein the RNA virus further comprises a gene encoding the human mixed lineage kinase domain-like (MLKL) protein.

Embodiment 17 The RNA virus vector according to embodiment 16, wherein the gene encoding the human MLKL protein comprises a nucleic acid sequence encoding the amino acid sequence of SEQ ID NO:15.

Embodiment 18 The RNA virus vector according to embodiment 15 or embodiment 16, wherein the gene encoding the human MLKL protein comprises RNA.

Embodiment 19 The RNA virus vector according to any one of embodiments 15 to 18, wherein the gene encoding the human MLKL protein comprises a negative sense RNA.

Embodiment 20 The RNA virus vector according to embodiment 15, wherein the gene encoding the human MLKL protein comprises the nucleic acid sequence of SEQ ID NO:3, SEQ ID NO:6, or the complement of SEQ ID NO:3 or SEQ ID NO:6.

Embodiment 21 A method for treating a tumor in a subject in need thereof, comprising infecting cells of the tumor with the RNA virus vector according to any one of embodiments 1 to 20.

Embodiment 22 The method according to embodiment 21, wherein the tumor is a tumor of the head and neck, esophagus, lung, breast, pancreas, kidney, liver, stomach, colon, ovary, uterus, prostate gland, bladder, or blood.

Embodiment 23 The method according to embodiment 21 or embodiment 22, wherein infecting cells of the tumor comprises administering to the subject the RNA virus vector.

Embodiment 24 The method according to any one of embodiments 21 to 23, wherein the RNA virus vector is actively targeted to the tumor.

Embodiment 25 The method according to any one of embodiments 21 to 24, wherein the subject is a human being.

Embodiment 26 A method for treating a viral infection in a subject in need thereof, comprising infecting cells infected with the viral infection with the RNA virus vector according to any one of embodiments 1 to 20.

Embodiment 27 The method according to embodiment 26, wherein the viral infection comprises a negative sense RNA virus infection.

Embodiment 28 The method according to embodiment 27, wherein the negative sense RNA virus infection is an influenza virus infection.

Embodiment 29 The method according to embodiment 28, wherein the influenza virus infection is an influenza type A virus infection.

Embodiment 30 The method according to embodiment 27, wherein the influenza virus infection is an influenza type B virus infection.

Embodiment 31 The method according to embodiment 27, wherein the influenza virus infection is an influenza type C virus infection.

Embodiment 32 The method according to any one of embodiments 26 to 31, wherein infecting cells infected with the viral infection comprises administering to the subject the RNA virus vector.

Embodiment 33 The method according to any one of embodiments 26 to 32, wherein the RNA virus vector is actively targeted to the cells infected with the viral infection.

Embodiment 34 The method according to any one of embodiments 26 to 33, wherein the subject is a human being.

Embodiment 35 Use of the RNA virus vector according to any one of embodiments 1 to 20 in the manufacture of a medicament.

Embodiment 36 Use of the RNA virus vector according to any one of embodiments 1 to 20 for the treatment of a tumor.

Embodiment 37 The use according to embodiment 36, wherein the tumor is a tumor of the head and neck, esophagus, lung, breast, pancreas, kidney, liver, stomach, colon, ovary, uterus, prostate gland, bladder, or blood.

Embodiment 38 Use of the RNA virus vector according to any one of embodiments 1 to 20 for the treatment of a viral infection.

Embodiment 39 The use according to embodiment 38, wherein the RNA virus vector is used for the treatment of a negative sense RNA virus infection.

Embodiment 40 The use according to embodiment 38 or 39, wherein the RNA virus vector is used for the treatment of an influenza type A, influenza type B, or influenza type C infection.

Embodiment 41 An RNA virus vector, comprising an RNA virus comprising a gene encoding the human DNA-dependent activator of interferon-regulatory factors (DAI) protein.

Embodiment 42 The RNA virus vector according to embodiment 41, wherein the RNA virus is a positive sense RNA virus.

Embodiment 43 The RNA virus vector according to embodiment 41 or embodiment 42, wherein the positive sense RNA virus is an attenuated Kunjin virus, Polio virus, Semliki Forest virus, Venezuelan Equine Encephalitis virus, or Sinbis virus.

Embodiment 44 The RNA virus vector according to embodiment 41, wherein the RNA virus is a negative sense RNA virus.

Embodiment 45 The RNA virus vector according to embodiment 41 or embodiment 44, wherein the negative sense RNA virus is an attenuated Rabies virus, Influenza virus, Vesicular Stomatitis virus, Respiratory Syncytial virus, Sendai virus, Measles virus, New Castle Disease virus, or Simian Virus 5 (SV5) virus.

Embodiment 46 The RNA virus vector according to embodiment 41, wherein the RNA virus is a retrovirus.

Embodiment 47 The RNA virus vector according to embodiment 41 or embodiment 46, wherein the retrovirus is an attenuated Lentivirus.

Embodiment 48 The RNA virus vector according to any one of embodiments 41 to 47, wherein the gene encoding the human DAI protein comprises a nucleic acid sequence encoding the amino acid sequence of SEQ ID NO:13.

Embodiment 49 The RNA virus vector according to any one of embodiments 41 to 48, wherein the gene encoding the human DAI protein comprises RNA.

Embodiment 50 The RNA virus vector according to any one of embodiments 41 to 49, wherein the gene encoding the human DAI protein comprises a negative sense RNA.

Embodiment 51 The RNA virus vector according to any one of embodiment 41 to 47, wherein the gene encoding the human DAI protein comprises the nucleic acid sequence of SEQ ID NO:1, SEQ ID NO:4, or the complement of SEQ ID NO:1 or SEQ ID NO:4.

Embodiment 52 A method for treating a tumor in a subject in need thereof, comprising infecting cells of the tumor with the RNA virus vector according to any one of embodiment 41 to 51.

Embodiment 53 The method according to embodiment 51, wherein the tumor is a tumor of the head and neck, esophagus, lung, breast, pancreas, kidney, liver, stomach, colon, ovary, uterus, prostate gland, bladder, or blood.

Embodiment 54 The method according to embodiment 52 or embodiment 53, wherein infecting cells of the tumor comprises administering to the subject the RNA virus vector.

Embodiment 55 The method according to any one of embodiments 52 to 54, wherein the RNA virus vector is actively targeted to the tumor.

Embodiment 56 The method according to any one of claims 52 to 55, wherein the subject is a human being.

Embodiment 57 A method for treating a viral infection in a subject in need thereof, comprising infecting cells infected with the viral infection with the RNA virus vector according to any one of embodiments 41 to 51.

Embodiment 58 The method according to embodiment 57, wherein the viral infection comprises a negative sense RNA virus infection.

Embodiment 59 The method according to embodiment 58, wherein the negative sense RNA virus infection is an influenza virus infection.

Embodiment 60 The method according to embodiment 59, wherein the influenza virus infection is an influenza type A virus infection.

Embodiment 61 The method according to embodiment 58, wherein the influenza virus infection is an influenza type B virus infection.

Embodiment 62 The method according to embodiment 58, wherein the influenza virus infection is an influenza type C virus infection.

Embodiment 63 The method according to any one of embodiments 57 to 62, wherein infecting cells infected with the viral infection comprises administering to the subject the RNA virus vector.

Embodiment 64 The method according to any one of embodiments 57 to 63, wherein the RNA virus vector is actively targeted to the cells infected with the viral infection.

Embodiment 65 The method according to any one of embodiments 57 to 64, wherein the subject is a human being.

Embodiment 66 Use of the RNA virus vector according to any one of embodiments 41 to 51 in the manufacture of a medicament.

Embodiment 67 Use of the RNA virus vector according to any one of embodiments 41 to 51 for the treatment of a tumor.

Embodiment 68 The use according to embodiment 67, wherein the tumor is a tumor of the head and neck, esophagus, lung, breast, pancreas, kidney, liver, stomach, colon, ovary, uterus, prostate gland, bladder, or blood.

Embodiment 69 Use of the RNA virus vector according to any one of embodiments 41 to 51 for the treatment of a viral infection.

Embodiment 71 The use according to embodiment 69, wherein the RNA virus vector is used for the treatment of a negative sense RNA virus infection.

Embodiment 72 The use according to embodiment 69 or embodiment 70, wherein the RNA virus vector is used for the treatment of an influenza type A, influenza type B, or influenza type C infection.

The following examples are provided to describe the present disclosure in greater detail. They are intended to illustrate, not to limit, the present disclosure.

EXAMPLES

Example 1: RIPK3-Mediated Apoptosis in Antiviral Immunity: Materials and Methods Mice and Cells. Ripk3−/−, ripk3−/−casp8−/−, fadd−/−, ripk3−/−fadd−/−, mlkl−/−, ripk3−/−mlkl−/−, mlkl−/−fadd−/−, ripk1−/−, ripk1k45/a/k45a, ripk1d138n/d138n, ifnar1−/−, stat1−/−, eif2ak2−/−, mavs−/−, and tnfr1−/− MEFs were generated in-house from E14.5 embryos and used within five passages in experiments. Early passage ddx58−/− and myd88−/−trif−/− MEFs were purchased from Oriental BioService Inc. (Osaka, Japan). HT-29 cells were obtained from the American Type Culture Collection (Manassas, Va.).

Reagents. Biological and chemical reagents were from the following sources: Necrostatin 1(Bio Vision), Nucleozin (Sigma), Q-VD-OPh (Apexbio), zIETD.fmk (Calbiochem), zVAD.fmk (Bachem), mIFN-β (PBL), murine and human TNF-α (R&D systems), mTRAIL (R&D systems), SMAC mimetic LCL161 (Chemietek). Inhibitors of RIPK1 (GSK'481, GSK'963) and RIPK3 (GSK'840, GSK'872, GSK'843) from GlaxoSmithKline. Antibodies for immunoblot analysis of β-actin (Sigma), caspase 8 (Cell Signaling), cleaved caspase 8 (Cell Signaling), FADD (Millipore), IAV NP (BioRad), IAV NS1 (Santa Cruz), MLKL (Abgent or Millipore), p-MLKL (Abcam), RIPK1 (BD Transduction Labs), RIPK3 (ProSci or Santa Cruz), were obtained from the indicated commercial sources. Neutralizing antibodies to mTNF-α (Cell Signaling) and mTRAIL-R2 (R&D systems) were obtained from the indicated sources. Antiserum to PR8 was produced in-house. For detection of IAV and CD3 in paraffin-embedded tissue, anti-IAV antibodies (US Biologicals) and anti-CD3 antibodies (Santa Cruz) were used. For FACS, antibodies to CD8α (clone 53-6.7), anti-CD16/CD32 (clone 2.4G2), anti-TNF-α (clone MP6-XT22), anti-IFN-γ (clone XMG1.2), and anti-CD28 were obtained from BD PharMingen.

Viruses. IAV strains PR8 and A/HKx31 were generated by reverse genetics. All IAV and IBV strains were propagated by allantoic action of embryonated hen's eggs with diluted (1:106) seed virus. Virus titers were determined as 50% egg infectious dose ($EID_{50}$) and by plaque assay on Madin-Darby Canine Kidney (MDCK) cells.

Virus Infection and Titration. Mice were anesthetized with Avertin (2,2,2-tribromoethanol) or isoflurane and infected intranasally with virus inoculum diluted in endotoxin-free phosphate-buffered saline. Mice were either monitored for survival and weight loss over a period of 18 days or sacrificed at defined time points for analysis of histology and virus replication. Mice losing >35% body-weight were considered moribund and euthanized by $CO_2$ asphyxiation. To determine progeny virus production in infected mice, lung homogenates were titered by plaque assay on MDCK cells. For cell culture experiments, near-confluent monolayers of cells were infected with virus in serum-free DMEM for 1 hour, with occasional gentle rocking, in a humidified tissue culture incubator maintained at 37° C. and 5% $CO_2$. Following infection, the inoculum was removed and replaced with growth medium. In conditions involving small-molecule inhibitors, cells were pre-incubated for 1 hour with inhibitors before infection; after removal of inoculum and washing, inhibitors were added back to the medium. Titration of virus from supernatants of infected LET1 cells was determined by a chicken red blood cell-based hemagglutination assay. Cell viability was determined by Trypan Blue exclusion or on an Incucyte Kinetic Live Cell Imaging System (Essen Bioscience).

Example 2: RIPK3-Mediated Apoptosis in Antiviral Immunity: Results

RIPK3 is required for IAV-induced cell death in murine fibroblasts and lung epithelial cells. To examine the role of RIPK3 in IAV induced cell death, early-passage murine embryo fibroblasts (MEFs) from ripk3−/− and littermate-control ripk3+/+mice were infected with IAV strains Puerto Rico/8/1934 (PR8), Brisbane/59/2007, Brisbane/10/2007, and Perth/16/2009 and these cells were observed over a time course of 36 hours. PR8 (H1N1) is a commonly-used natural isolate of IAV, while Brisbane/59/2007 (H1N1), Brisbane/10/2007 (H3N2), and Perth/16/2009 (H3N2) and are seasonal strains of IAV. Two strains of influenza B virus (IBV), Brisbane/60/2008 and Florida/4/2006, were also included.

Figure 1A:
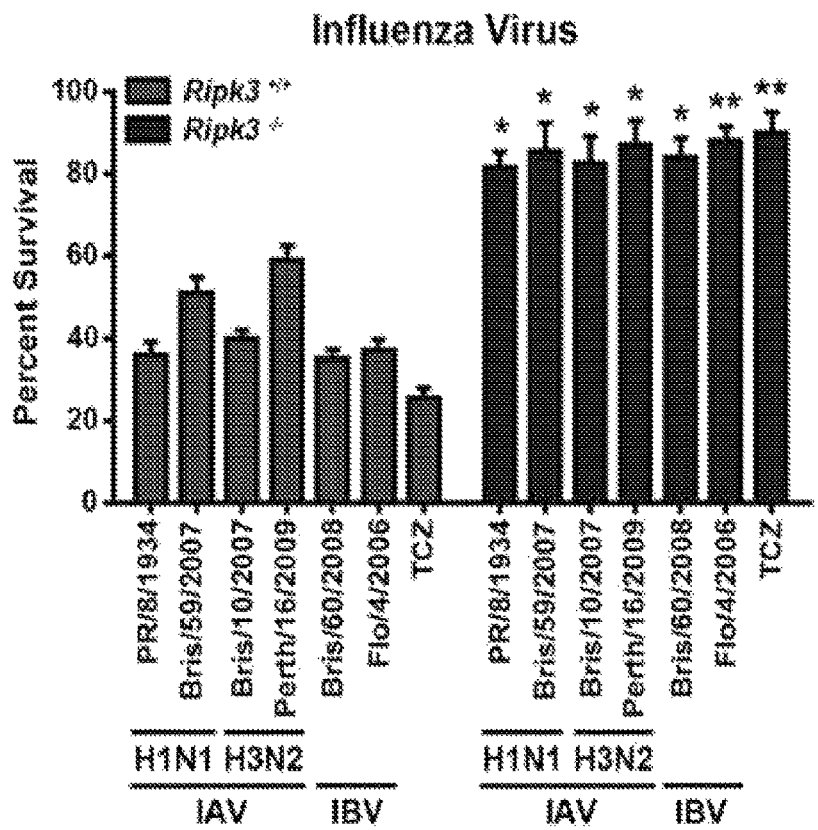
Figure 1B:
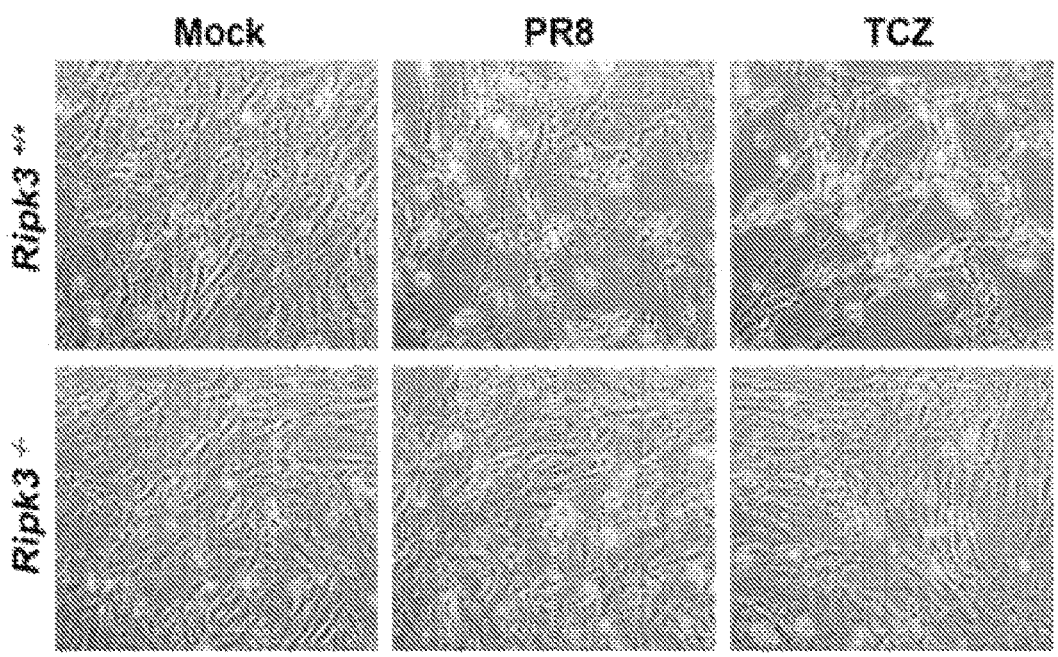
Figure 1C:
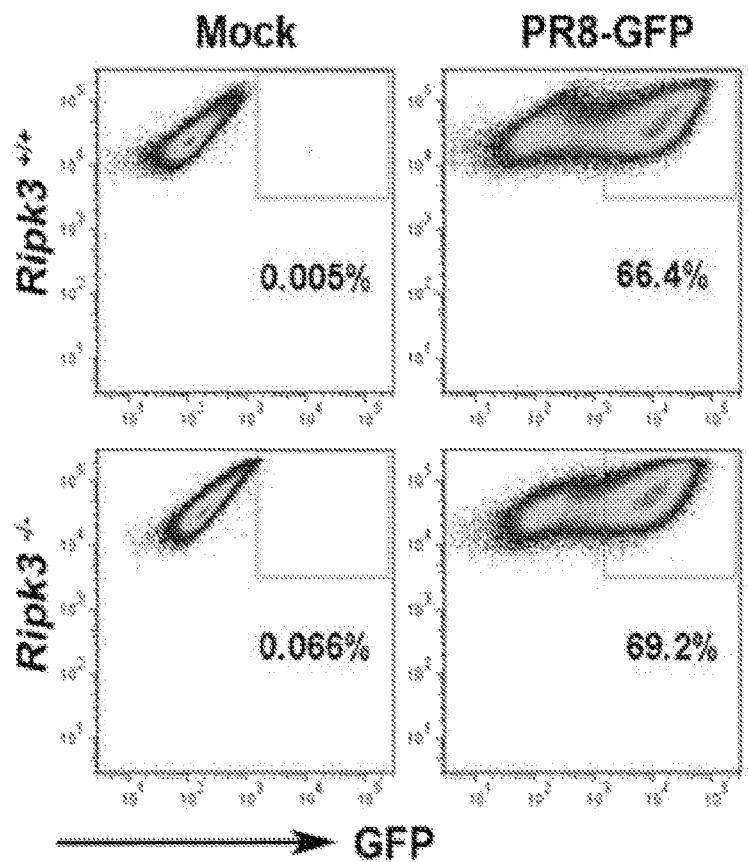
Figure 1D:
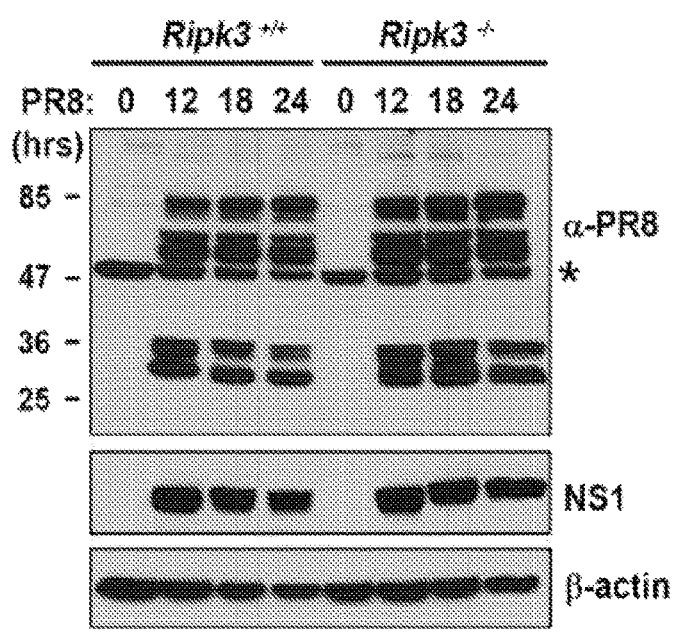
Figure 2A:
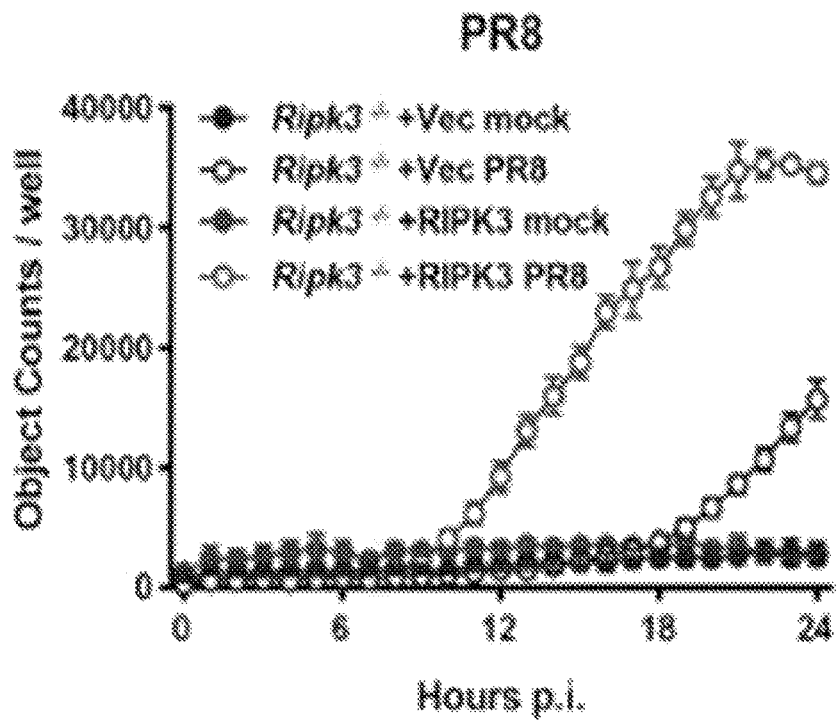
FIGS. 2A through 2C show the role of TNF-α and TRAIL in IAV-activated RIPK3-independent apoptosis.

Each of these strains induced extensive cytopathic effect (CPE) and cell death in infected wild-type MEFs within 24 hours (see, FIGS. 1A and 1B). Similarly-infected ripk3−/− MEFs were almost completely resistant to IAV- and IBV-induced CPE and cell death at this time point (>85% viability, see, FIGS. 1A and 1B), indicating that activating RIPK3-mediated cell death is a common cytopathic feature of influenza viruses. Focusing on IAV for the rest of this study, it was observed that the capacity of ripk3−/− MEFs to withstand IAV-induced lysis paralleled their resistance to cell death induced by the combination of TNF-α, cycloheximide, and the pan-caspase inhibitor zVAD (TCZ), an established trigger of necroptosis in MEFs (see, FIGS. 1A and 1B), and was largely reversed by the re-introduction of RIPK3 expression (see, FIG. 2A). Using recombinant PR8 expressing GFP (PR8-GFP) it was observed that ripk3−/− MEFs were neither defective in viral entry nor any less permissive to IAV than ripk3+/+ MEFs: both genotypes displayed equivalent levels GFP-positivity 24 h.p.i. with PR8-GFP (see, FIG. 1C). In line with these observations, immunoblot analysis of viral protein expression in lysates prepared from ripk3+/+ and ripk3−/− MEFs infected with PR8 over a 24 hour time course revealed no evidence of either decreased infectivity or delayed kinetics of replication in cells lacking RIPK3 (see, FIG. 1D).

Figure 2B:
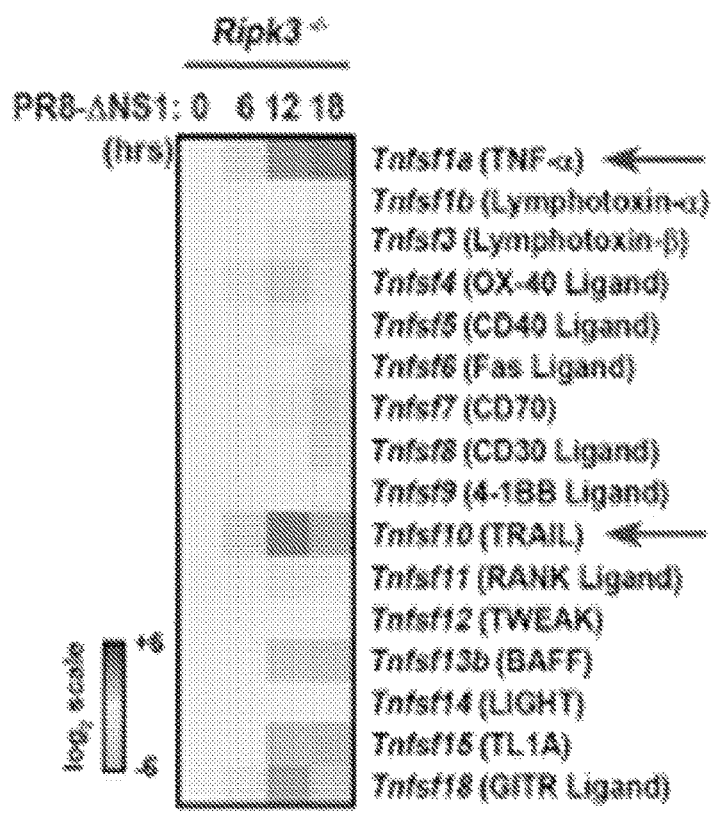
Figure 2C:
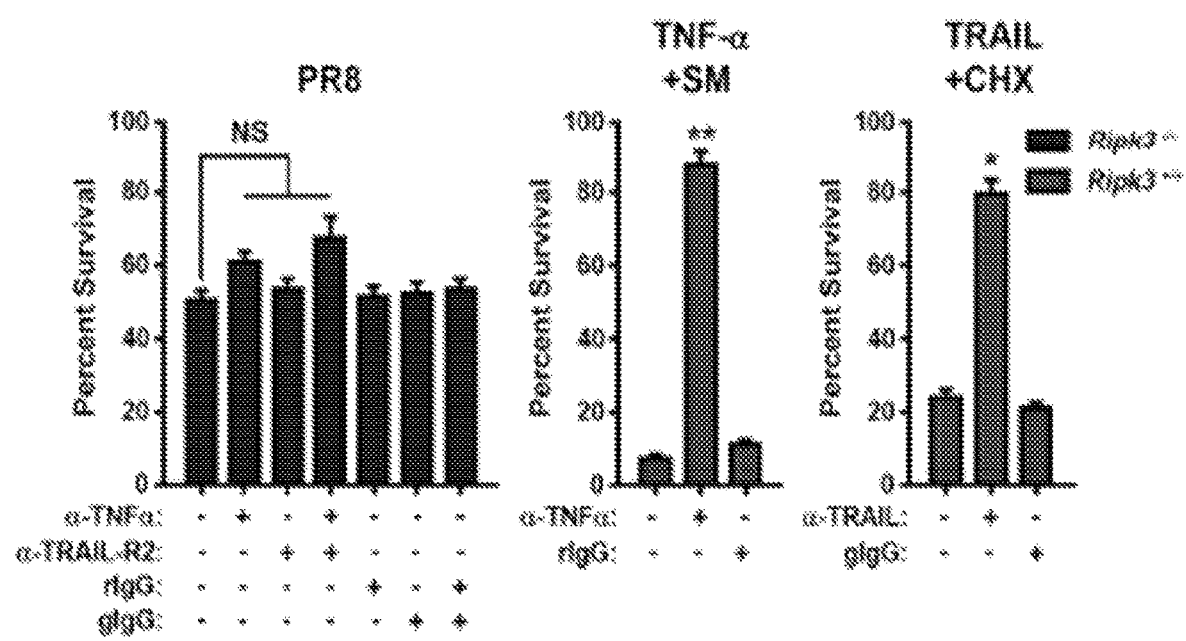

By 36 h.p.i., most (>80%) ripk3+/+ MEFs infected with IAV (hereafter PR8) were dead, while approximately half the population of infected ripk3−/− MEFs remained alive (see, FIG. 1E). Similarly infected ripk3−/− treated with zVAD or additionally lacking the apoptosis effectors caspase 8 or FADD remained mostly alive at this time point, indicating that the delayed death seen in ripk3−/− MEFs was mediated by a residual RIPK3-independent FADD/caspase 8-dependent pathway of apoptosis (see, FIG. 1F). Neither TNF-α or TRAIL-mediated mechanisms, either alone or in combination, appeared to account for this pathway of RIPK3-independent apoptosis in IAV-infected MEFs (see, FIGS. 2B and 2C).

To extend these analyses to a physiologically relevant cell type, it was next assessed if RIPK3-driven cell death is triggered in lung type I alveolar epithelial cells (AECs) following infection with IAV. Employing the immortalized murine type I AEC cell line LET1, it was first confirmed that type I AECs express RIPK3 and its essential cell death regulators, RIPK1, FADD, MLKL and caspase 8, at levels comparable to those found in MEFs (see, FIG. 3). Upon infection with PR8, LET1 cells showed clear evidence of CPE within 3 hours, and succumbed to infection within 12 h.p.i. (see, FIG. 1G, left). CRISPR/Cas9-mediated ablation of RIPK3 expression protected LET1 cells from PR8 (see, FIG. 1G, left), demonstrating that RIPK3-driven cell death mechanisms are conserved between MEFs and lung AECs. Notably, LET cells lacking RIPK3 produced significantly more progeny virions than control LET1 cells containing RIPK3, predictive of a prominent role for RIPK3-driven cell death in clearance of virus from the infected lung (see, FIG. 1G, right).

Figure 4A:
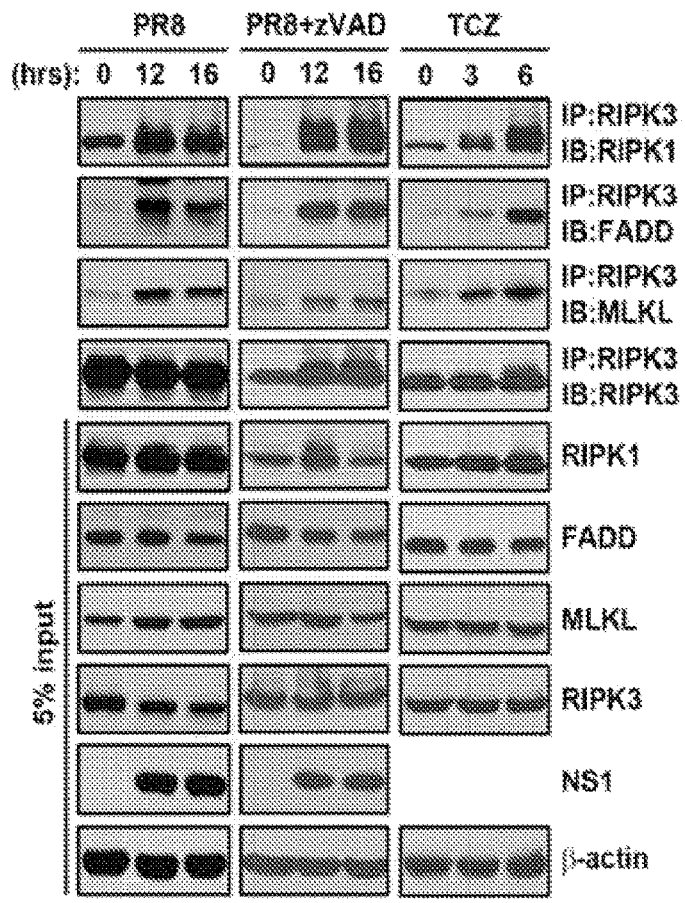
FIGS. 4A through 4E show IAV activates formation of a RIPK3-containing necrosome complex.

IAV replication results in assembly of a RIPK3 complex containing RIPK1, FADD and MLKL. A molecular feature of RIPK3 dependent cell death is the stimulus-driven formation of a molecular complex called the necrosome, comprising as its core phosphorylated forms of RIPK3 and RIPK1, together with FADD and MLKL. From the necrosome, RIPK3 can activate both necroptosis and apoptosis, depending on target availability or RIPK3 activity. To test if IAV induced formation of a necrosome, RIPK3 was immunoprecipitated from lysates of PR8-infected MEFs, and immunoprecipitates were examined for the presence of slower-mobility forms of phosphorylated RIPK1. PR8 activated necrosome formation to a significant extent, as did the combination of PR8+zVAD (see, FIG. 4A, left and middle panels). Like TNF-α (see, FIG. 4A, right panels), IAV infection also drove the recruitment of FADD and MLKL into the RIPK3-RIPK1 necrosome. As zVAD alone at this dose (25 µM) did not induce detectable necrosome formation, and as the combination of PR8+zVAD stabilized the necrosome to allow more reliable detection of IAV-activated RIPK3-containing complexes over PR8 alone, this combination we used for subsequent dissection of the molecular determinants of IAV-triggered RIPK3 complex formation.

Figure 4B:
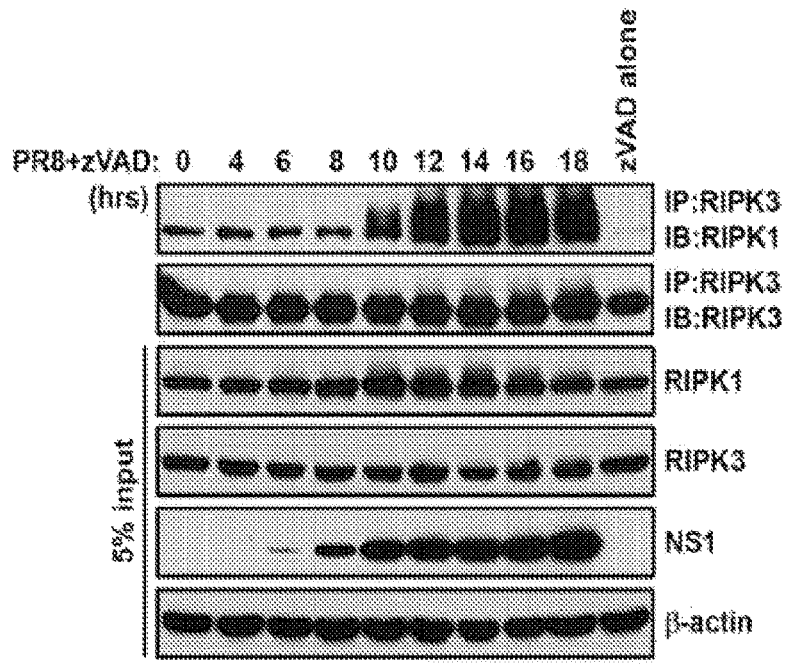
Figure 4C:
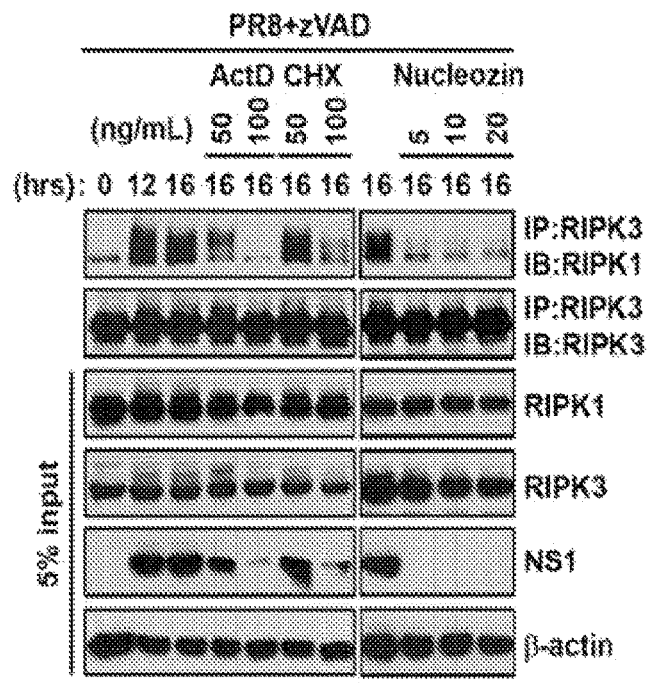

It was observed that PR8 induced a RIPK3-RIPK1 complex in MEFs beginning at ~10 h.p.i., after the start of viral protein NS1 accumulation, which was detectable at ~6-8 h.p.i (see, FIG. 4B). Given that IAV-induced RIPK3 necrosome assembly was preceded by viral protein synthesis, it was next tested if active transcription, translation, or viral genome replication was required for IAV-induced RIPK3 activation. Pre-treatment of MEFs with the RNA polymerase II inhibitor Actinomycin D (ActD, which also blocks IAV replication: host RNA polymerase II is needed for export of IAV mRNAs from the nucleus to the cytoplasm) or with an inhibitor of mRNA translation, cycloheximide (CHX), effectively prevented both viral replication and RIPK3-RIPK1 complex formation (see, FIG. 4C). Neither ActD nor CHX at these doses affected TNF-α-induced necrosome assembly (not shown). The IAV nucleoprotein inhibitor nucleozin also potently blocked RIPK3-RIPK1 association at doses that abrogated viral replication (see, FIG. 4C). Together, these results demonstrate that IAV replication drives activation of RIPK3.

Figure 4D:
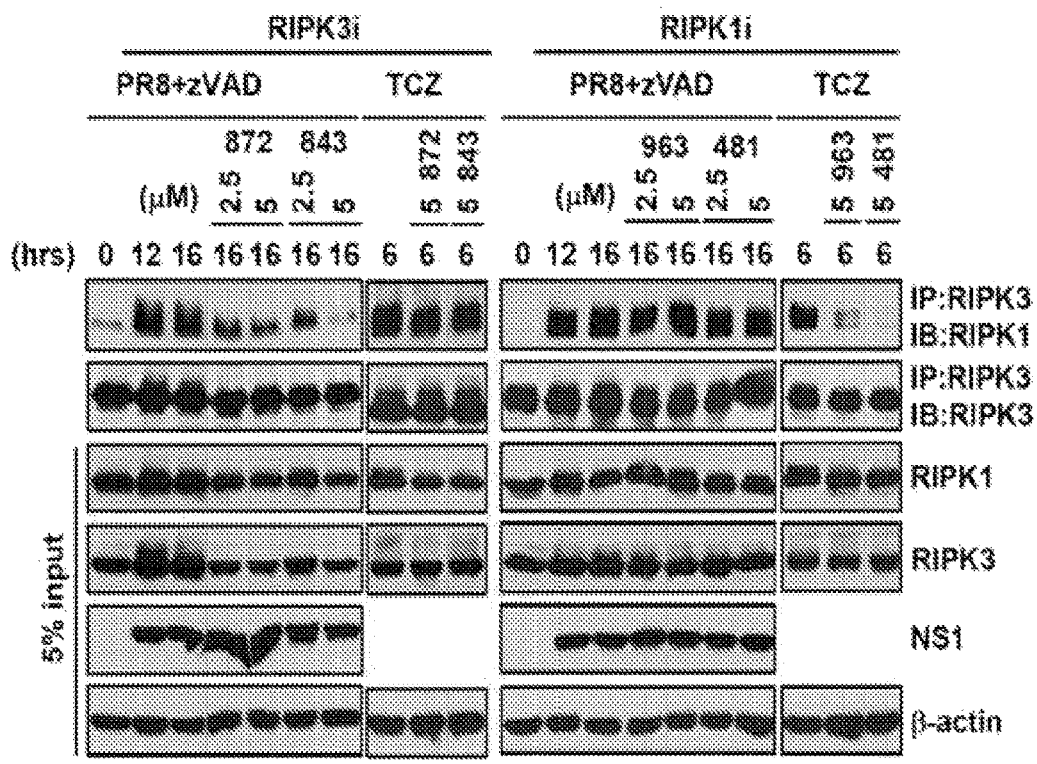

Next, kinase inhibitors specific for either RIPK1 or RIPK3 were employed to identify roles for the kinase activity of each of these proteins in IAV-induced RIPK3-RIPK1 complex assembly. Downstream of TNFR1, the kinase activity of RIPK1, but not RIPK3, was necessary for necrosome formation (see, FIG. 4D, left panels), although both classes of inhibitor were potent blockers of TNF-α-induced cell death (see, FIG. 5A). In contrast to how these kinases function in the TNF-α pathway, it was observed that the kinase activity of RIPK3 was required for IAV-induced necrosome formation, while that of RIPK1 was largely dispensable (see, FIG. 4D, right panels). Thus, while RIPK3 complexes activated by TNF-α and IAV both contain RIPK1, FADD, and MLKL, and are licensed by caspase inhibition, they display contrasting requirements for the kinase activities of RIPK1 versus RIPK3.

Figure 4E:
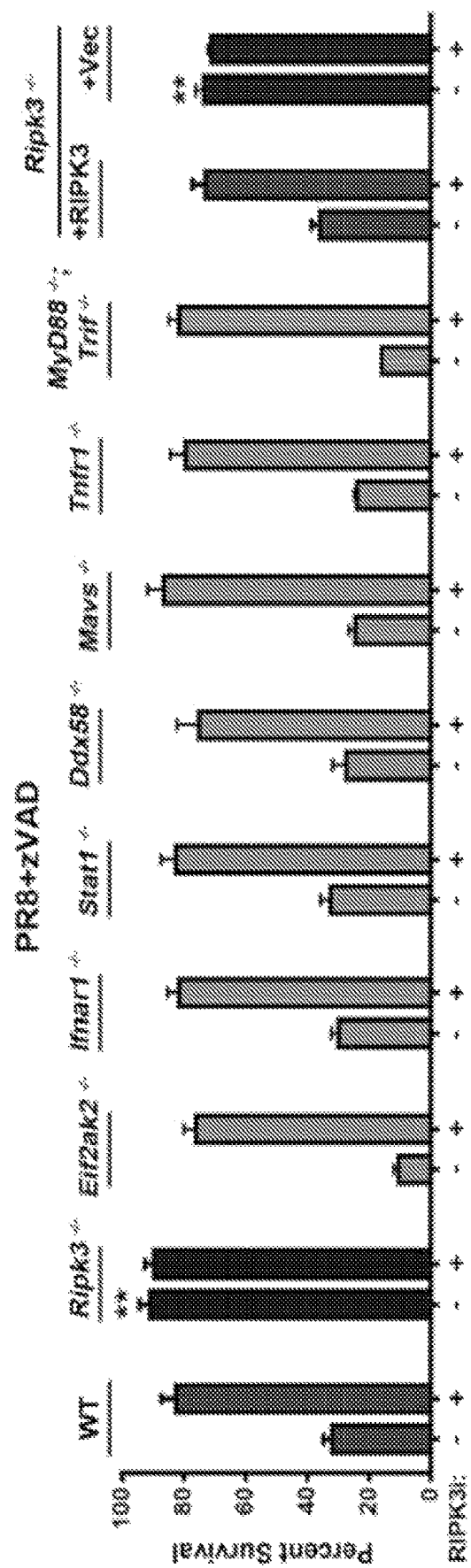
Figure 6:
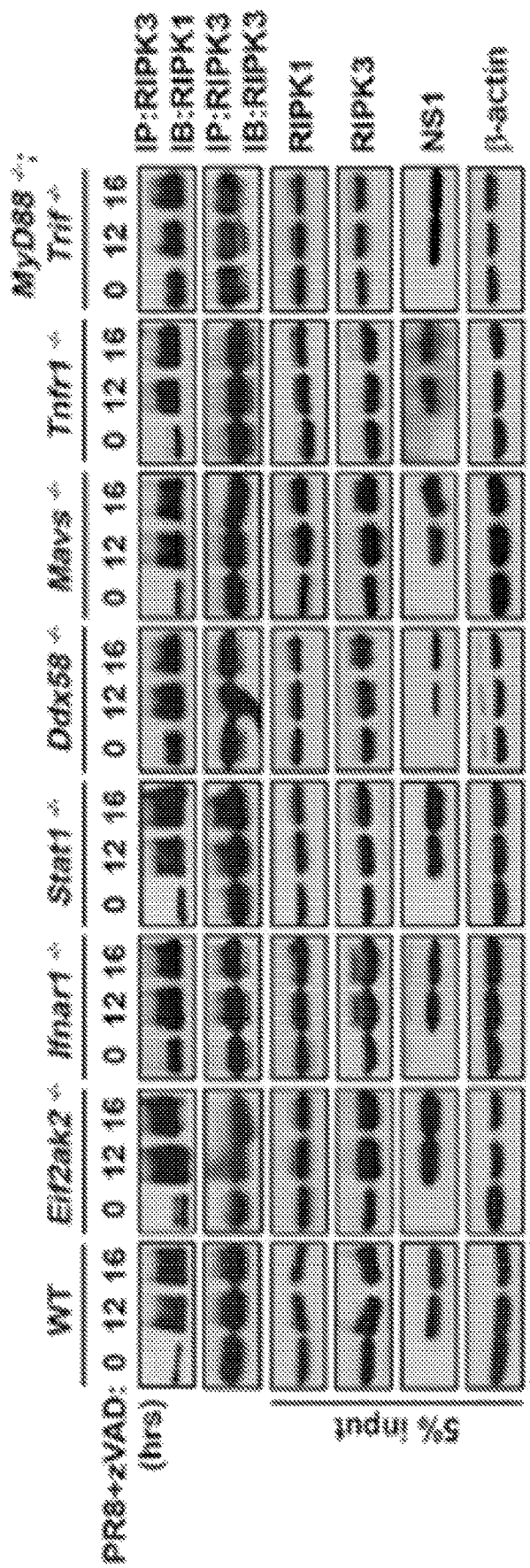
FIG. 6 shows IAV-induces necrosome formation is independent of type 1 IFNs, TNF-α, or known RNA sensing pathways. RIPK3-RIPK1 necrosome formation was evaluated on lysates from the indicated PR8-infected wild-type or knock-out MEFs. PR8 (m.o.i.=2) in the presence of zVAD (25 µM) was used to stimulate necrosome formation.

Several innate-immune pathways are triggered by an acute RNA virus, many of which (e.g., TNF-α, type I IFNs, TLR3) have been shown to activate RIPK3. To test if any of these pathways are responsible for necrosome formation and RIPK3-driven cell death in response to IAV infection, primary MEFs deficient in either PKR, IFNAR1, STAT1, RIG-I, MAVS, TNFR1 or MyD88/TRIF were infected and monitored for necrosome formation and RIPK3-dependent cell death in these cells. IFNAR1, STAT1 and PKR are required for type I IFN-induced necroptosis in MEFs, while ablation of TNFR1, RIG-I/MAVS, or MyD88/TRIF was expected to abolish RIPK3 activation by, respectively, TNF-α, RLRs, and TLRs. In each case, RIPK3-dependent cell death (see, FIG. 4E) and formation of the RIPK3-RIPK1 complex (see, FIG. 6) were largely indistinguishable between wild-type MEFs and MEFs deficient in type I IFN, TNF-α, RLR or TLR signaling. These results indicate that IAV replication either induces RIPK3-mediated cell death by mechanism(s) distinct from known RIPK3-activating pathways, or, alternatively, triggers redundant combinations of these pathways to activate RIPK3.

IAV activates parallel pathways of necroptosis and apoptosis downstream of RIPK3. Recent evidence shows that RIPK3 activates not only MLKL-driven necrotic cell death but, under certain conditions (e.g., when its kinase activity is inhibited or its conformation altered) caspase-dependent apoptosis as well. To distinguish between apoptotic and necrotic cell death mechanisms activated by IAV downstream of RIPK3, the effects of selective RIPK1 and RIPK3 kinase inhibitors, as well as of the pan-caspase blocker zVAD, on viability of wild-type MEFs after infection with PR8 were examined RIPK1 kinase blockade with GSK'963, GSK'481 or Nec-1 did not have any discernible protective effect on viability of MEFs after infection with PR8 (see, FIG. 5A), an observation in line with the inability of these agents to prevent IAV-driven necrosome formation (see, FIG. 4D). Surprisingly, RIPK3 kinase inhibition with GSK'872 or GSK'843 also failed to prevent PR8-induced cell death, although each of these inhibitors blocked PR8-induced necrosome assembly (see, FIG. 4D) and was fully protective against TNF-α-induced necroptosis at the same doses (see, FIG. 3A). Similarly, zVAD by itself did not protect MEFs from PR8-induced cell deaths (see, FIG. 5A)

at a dose that prevented apoptosis induced by the combination of TRAIL and cycloheximide (not shown). But the combination of RIPK3 kinase inhibitors with zVAD conferred almost full protection against PR8-induced cell death in both MEFs (see, FIG. 5A) and LET1 AECs (see, FIG. 5B). In similar studies on the necroptosis-competent human HT-29 cell line, it was observed that IAV-activated cell death was not singly prevented by either caspase or RIPK3 blockade, but was significantly rescued by the combined inhibition of caspases and RIPK3 kinase activity (see, FIG. 5C). Thus, IAV-activated RIPK3-dependent cell-death mechanisms appear conserved between humans and mice.

Figure 5D:
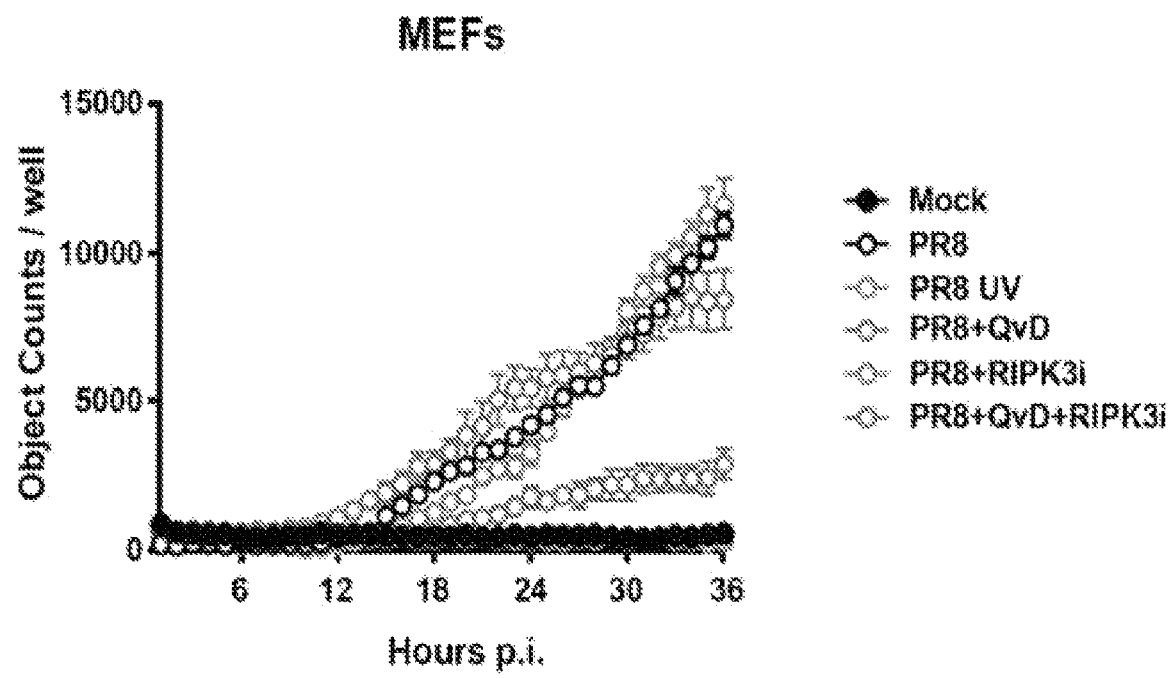

Notably, RIPK1 inhibitors deployed under similar conditions were incapable of protection against PR8 in the presence of zVAD (see, FIG. 5A). Together with the results from the use of these inhibitors in the necrosome assembly experiments shown in FIG. 4, these findings implicate a dominant role for the kinase activity of RIPK3, but not RIPK1, in PR8-driven necrotic death. They also indicate that parallel, redundant pathways of apoptosis and kinase-dependent necroptosis are activated by IAV infection downstream of RIPK3. In agreement with these observations, kinetic analysis of cell death in IAV-infected wild-type MEFs demonstrated that neither a caspase inhibitor nor an inhibitor of RIPK3 kinase function were singly able to protect against cell death, but the combined inhibition of caspases and RIPK3 kinase activity was significantly protective (see, FIG. 5D).

Figure 5E:
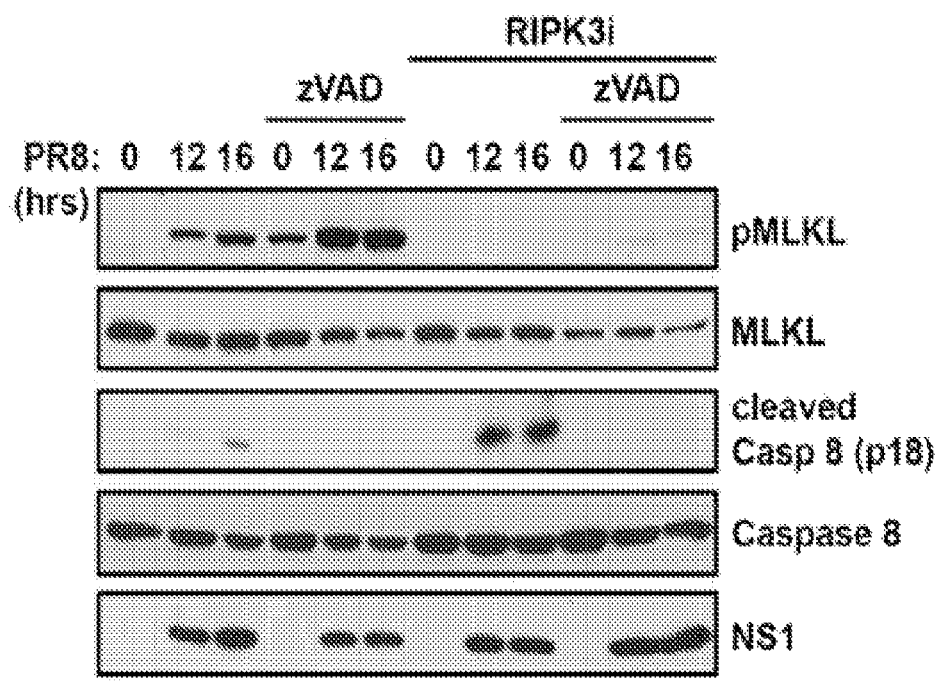
Figure 7A:
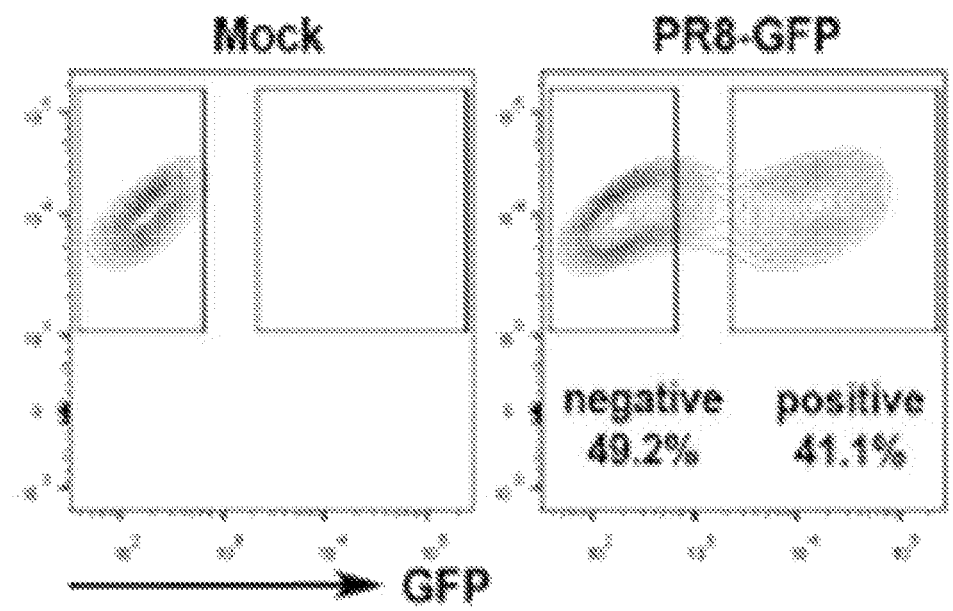
FIGS. 7A and 7B show activation of apoptosis and necroptosis is intrinsic to the IAV-infected cell.
Figure 7B:
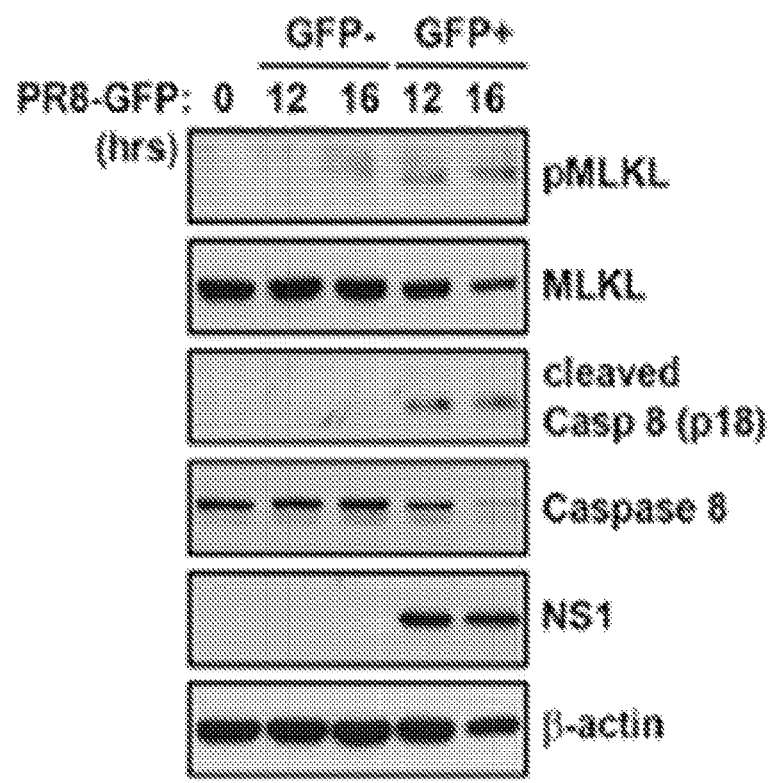

IAV induced both MLKL phosphorylation and cleavage of caspase 8 in MEFs, only the first of which was inhibited by RIPK3 kinase blockade and only the second by zVAD (see, FIG. 5E). Both MLKL phosphorylation and cleavage of caspase 8 were only seen in cells harboring actively-replicating IAV, and not in cells without detectable replicating virus, indicating that both arms of IAV-activated RIPK3-dependent cell death are phenomena restricted to the infected cell, and not the result of bystander activity on surrounding, uninfected cells (see, FIG. 7).

Figure 8A:
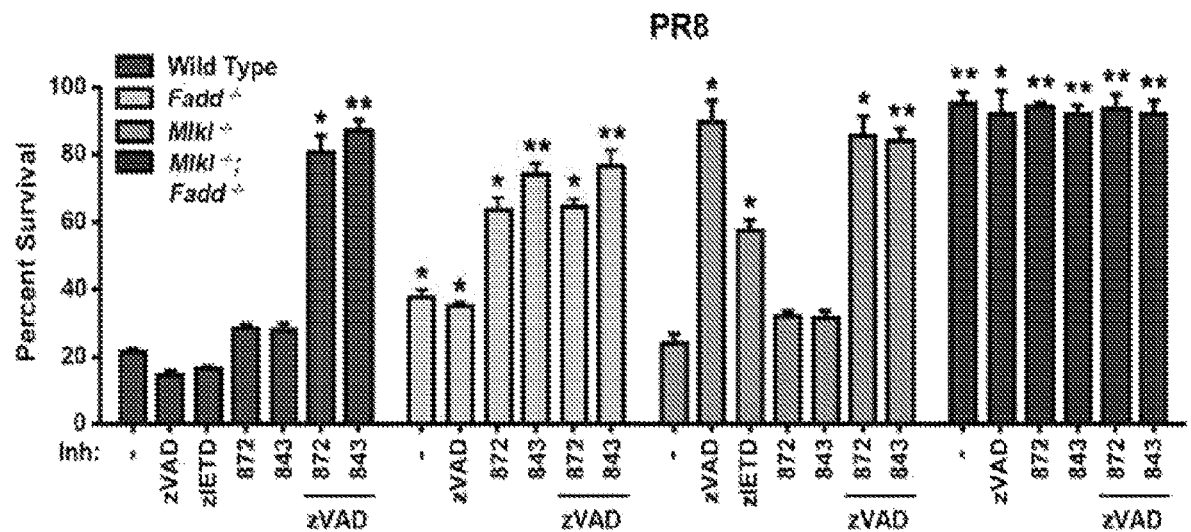
FIGS. 8A and 8B show MLKL drives necroptosis and FADD mediates apoptosis following IAV infection.
Figure 9A:
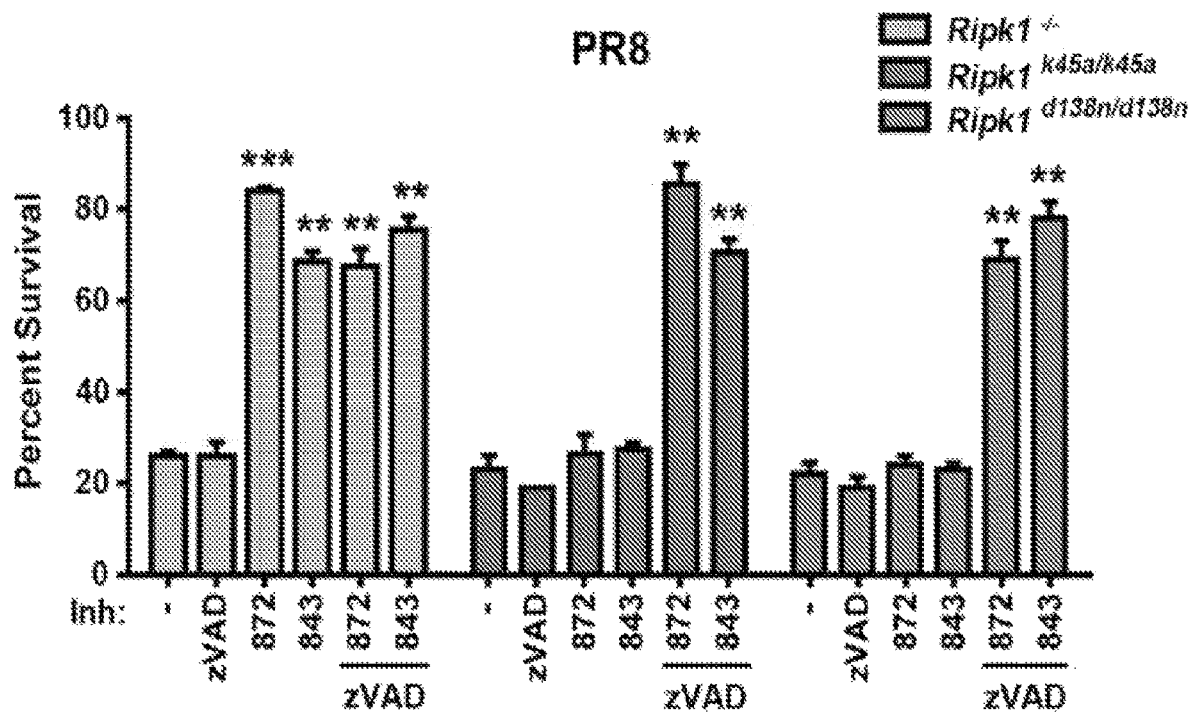
FIGS. 9A through 9D show IAV activates both RIPK3-dependent early apoptosis and RIPK3-independent late apoptosis in MLKL-deficient cells.

MLKL mediates necroptosis while FADD and caspase 8 drive apoptosis upon IAV infection. As MLKL has emerged as the primary effector of RIPK3-activated necroptosis, and as PR8-induced the robust phosphorylation of MLKL, the role of this pseudokinase in IAV-triggered cell death was next evaluated. Upon infection with PR8, primary mlkl–/– MEFs, unlike ripk3–/– MEFs, were not any more resistant to cell death than their wild-type counterparts, and succumbed to this virus with kinetics and magnitude indistinguishable from controls. The mlkl–/– MEFs were fully rescued from PR8-induced cell death by pretreatment with zVAD alone, without need for concurrent inhibition of the kinase activity of RIPK3 (see, FIG. 8A). Pretreatment of mlkl–/– MEFs with the caspase 8-specific inhibitor zIETD also provided significant protection against PR8, while RIPK3 kinase blockade by itself had no effect (see, FIG. 8A). As levels of key effector proteins, including RIPK1 and RIPK3, are comparable between mlkl+/+ and mlkl–/– MEFs (see, FIG. 3), these results provide unambiguous evidence that IAV-activated death signaling bifurcates downstream of RIPK3 into MLKL-driven necroptosis (which requires the kinase activity of RIPK3) and caspase-mediated apoptosis (which does not). They also implicate caspase 8 as a dominant caspase in the RIPK3-regulated cell death axis that results in apoptosis. Of note, zIETD consistently afforded less protection against PR8 than zVAD did, even when replenished at 12 hours, in agreement with findings that zIETD is weaker than zVAD at preventing caspase 8-driven apoptosis (see, FIG. 9A).

Given the observation that the apoptosis adaptor protein FADD is recruited to the IAV-activated necrosome, it was next asked if FADD was involved in the IAV-activated apoptosis arm downstream of RIPK3. Accordingly, fadd–/– MEFs were infected with PR8 and the viability of these cells in the presence or absence of zVAD and/or RIPK3 inhibitors was monitored. Fadd–/– MEFs were somewhat more resistant to IAV-induced cell death than wild-type MEFs. This resistance may be attributable, at least in part, to the reduced basal levels of MLKL seen in fadd–/– MEFs (see, FIG. 6, see also FIG. 8B). As fadd–/– MEFs display heightened basal necrosome activity, diminished MLKL levels may supply a survival advantage to these cells, allowing their continued propagation in culture. Nonetheless, the loss of viability of fadd–/– MEFs following PR8 infection was almost completely rescued by pretreatment of these cells with RIPK3 kinase inhibitors, but not with zVAD (see, FIG. 8A).

Figure 9B:
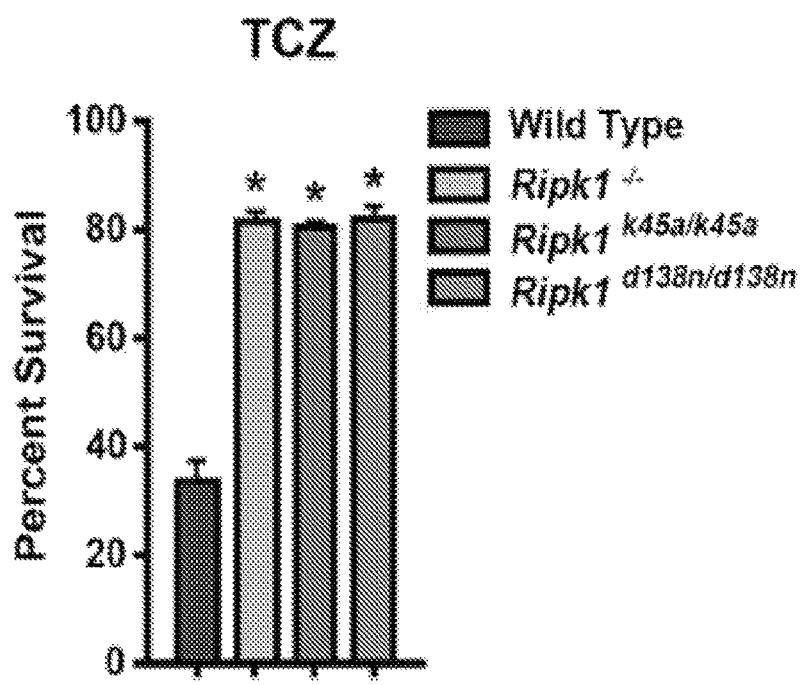
Figure 9C:
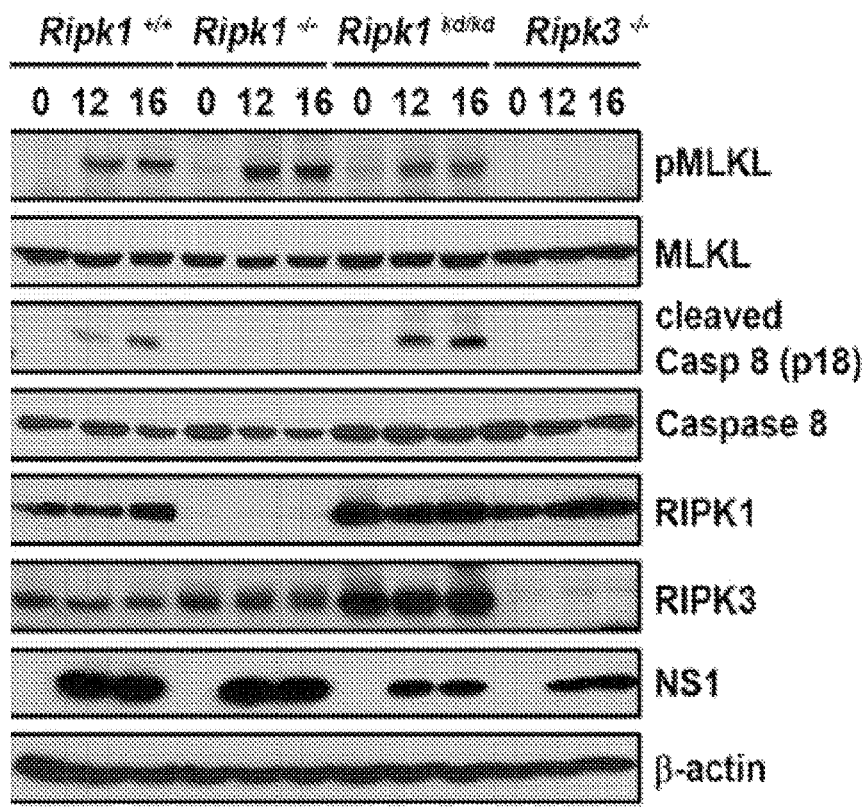

These results indicate that MLKL and FADD each drive parallel, independent pathways of, respectively, necroptosis and apoptosis downstream of RIPK3. They also suggest that combined ablation of both MLKL and FADD will be needed to afford protection from IAV-induced cell death that is comparable to what is observed when RIPK3 is absent. To test this idea, mice homozygously null for both mlkl and fadd we regenerated. Ablating mlkl rescued the embryonic lethality of fadd–/– mice, and mlkl–/–fadd–/– double knock-out mice are born at normal Mendelian frequency, exhibit no overt developmental defects, and survive into adulthood. When primary MEFs from mlkl–/–fadd–/– double knock-out mice were infected with IAV, they were observed to be remarkably (>95%) resistant to virus-induced cell death. Indeed, MEFs from these mice were even more resistant to IAV-triggered cell death than MEFs from ripk3-deficient mice, surviving for over 60 h.p.i. at an m.o.i. of 5 (see, FIG. 9B), without any obvious defects in either IAV infectivity (not shown) or replication (see, FIG. 9C). Thus, MLKL- and FADD-dependent cell death axes together almost completely account for IAV-triggered cell death, both downstream of RIPK3 and, indeed, independent of this kinase (see, FIGS. 1F and 10).

Figure 8B:
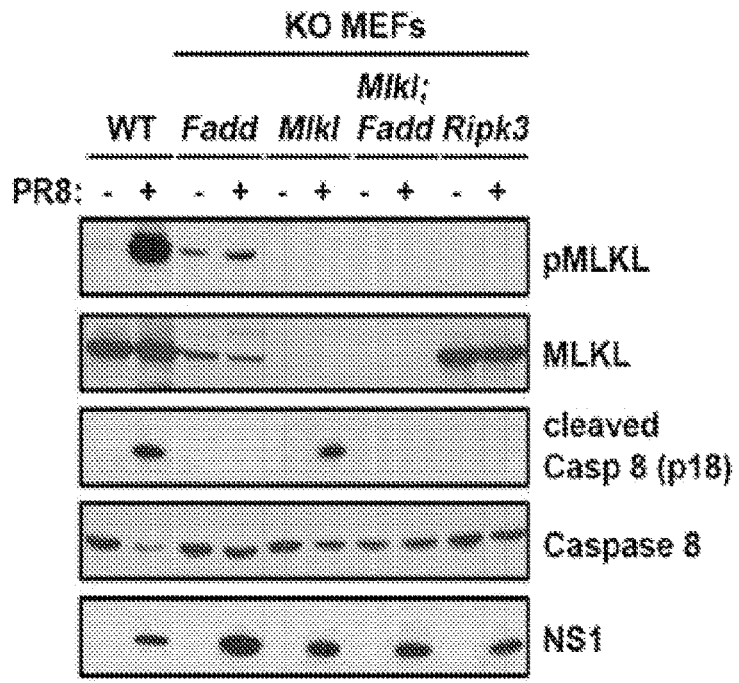
Figure 9D:
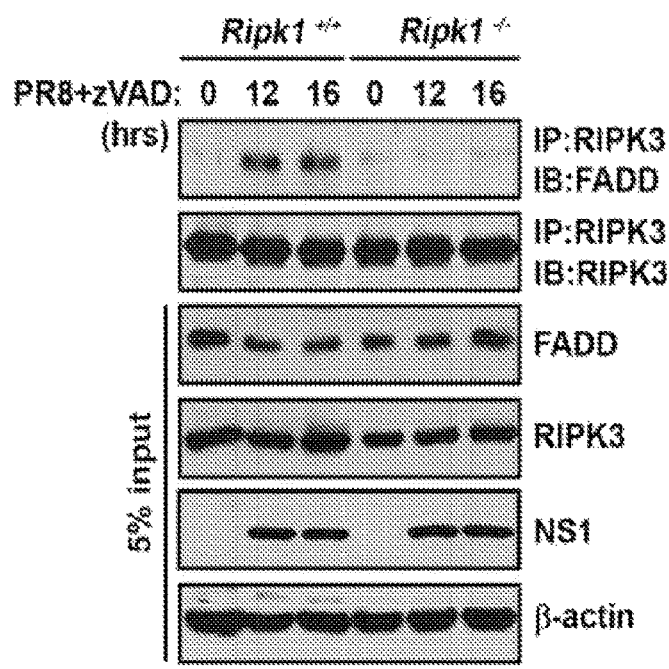

In accord, mlkl–/– MEFs showed no defect in caspase 8 activation upon IAV infection, but displayed no MLKL phosphorylation, while fadd–/– MEFs were completely deficient in their capacity to activate caspase 8 after infection with IAV, but continue to support phosphorylation of MLKL (see, FIG. 8B). Only mlkl–/–fadd–/– double knock-out MEFs, like ripk3–/– MEFs, were deficient in their ability to activate either pathway (see, FIG. 8B). Both RIPK3-dependent early apoptosis and RIPK3-independent late apoptosis proceed normally on a background of MLKL deficiency, demonstrating the parallel nature of apoptosis and necroptosis pathways activated by IAV (see, FIG. 9D).

Figure 3:
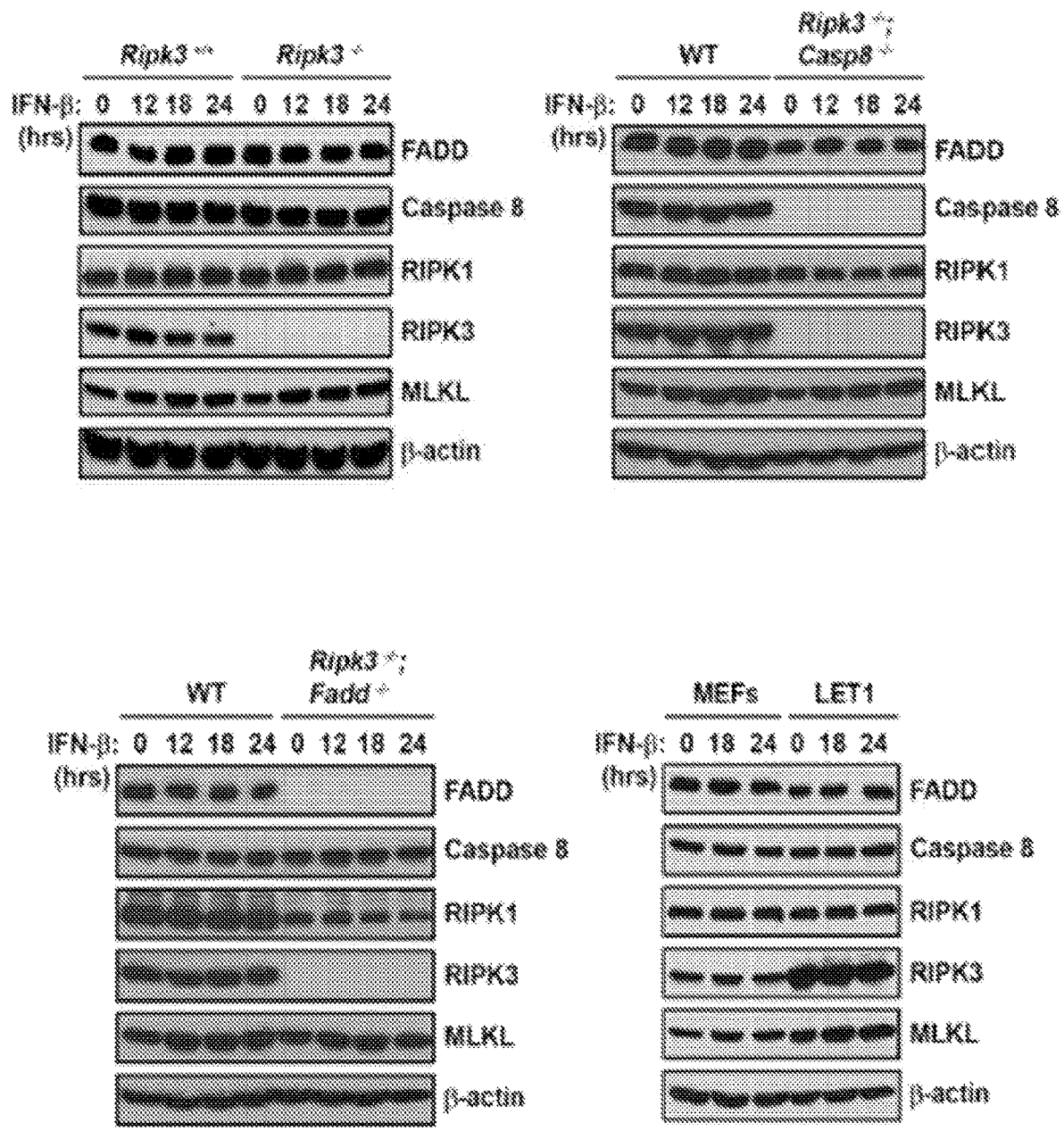
FIG. 3 shows the levels of effector proteins in cells used. Levels of key cell death effector proteins were examined in the indicated murine cell lines by immunoblot analysis following treatment with mIFN-β (1000 U/ml) for up to 24 hours.
Figure 3:
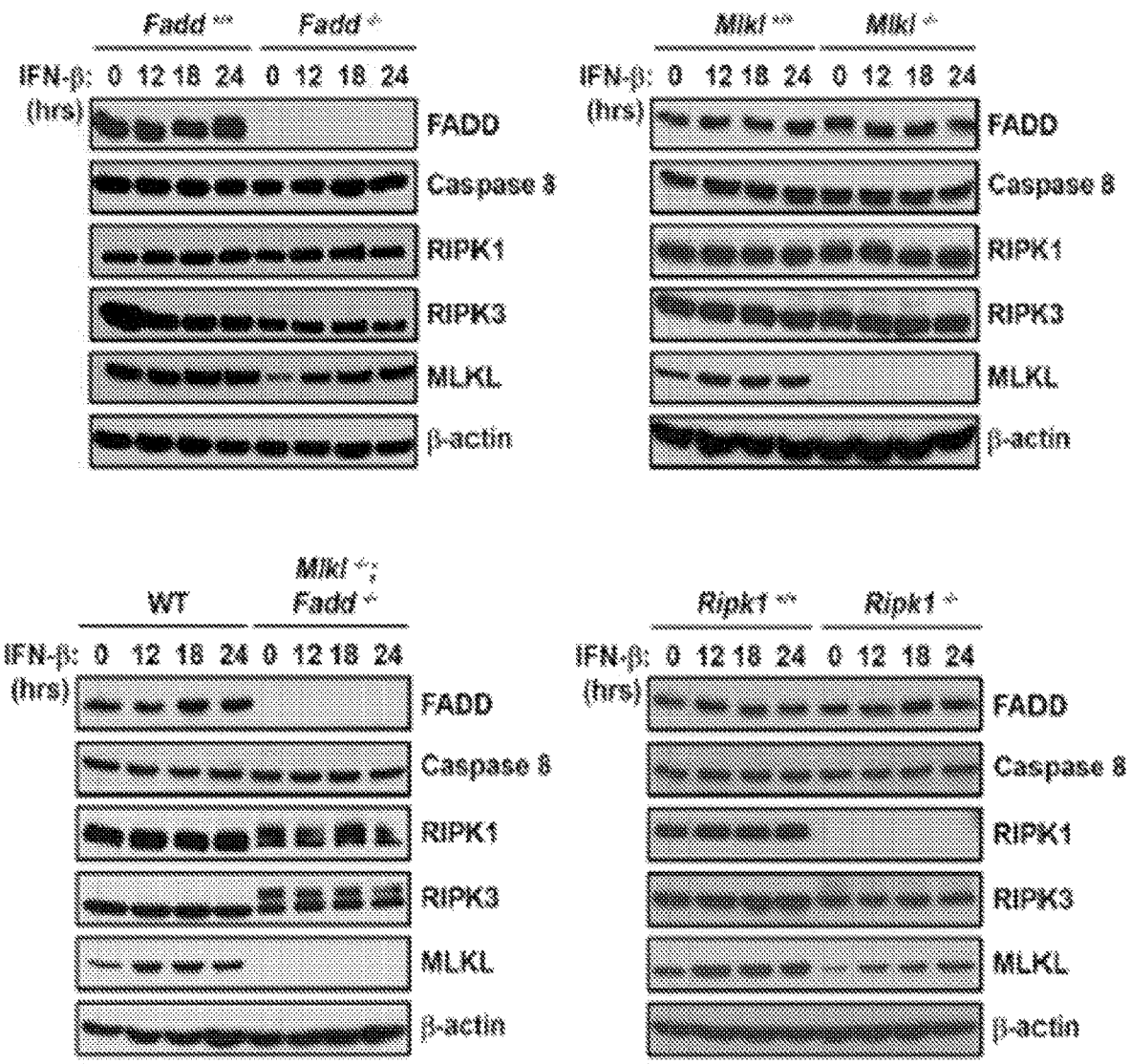

The mlkl–/–fadd–/– double knock-out MEFs displayed altered mobility of RIPK1 and RIPK3 by SDS-PAGE, when compared to wild-type MEFs (see, FIG. 3). Pre-incubation of mlkl–/– fadd–/– double knock-out MEFs with RIPK1 or RIPK3 kinase inhibitors demonstrate that, at least in the case of RIPK3, the slower-migrating band represents an auto-phosphorylated version of this kinase (not shown), suggesting unanticipated roles for FADD and MLKL in homeostatic control of basal RIPK1/3 expression and activity.

Role of RIPK1 in IAV-activated RIPK3-dependent cell death pathways. Although RIPK1 is robustly recruited to, and phosphorylated by, RIPK3 upon IAV infection, its role as a kinase in the execution of necroptosis following IAV infection appears unnecessary (see, FIG. 5A). As RIPK1 can function as an apoptosis adaptor downstream of RIPK3, the roles of this protein in RIPK3-activated cell death upon IAV infection were investigated. To this end, ripk1−/− MEFs were infected with PR8 and the viability of these cells in the presence or absence of zVAD or the RIPK3 inhibitors GSK'843 and GSK'872 was examined Ripk1−/− MEFs, unlike ripk3−/− MEFs, displayed no significant resistance to PR8, and succumbed to this virus with kinetics indistinguishable from wild-type MEFs (see, FIG. 10A). Ripk1−/− MEFs, however, were almost-fully protected from PR8-induced cell death by pre-treatment with RIPK3 kinase inhibitors (but not with zVAD), demonstrating that, like FADD, RIPK1 was essential for the apoptosis axis downstream of RIPK3. MEFs from two distinct RIPK1 kinase-dead knock-in mice ripk1k45a/k45a and ripk1d138n/d138n phenocopied wild-type MEFs in their cell death responses to IAV, demonstrating that the kinase activity of RIPK1 was not required for activating apoptosis after infection (see, FIG. 10A). The ripk1−/− MEFs, as well as MEFs from RIPK1 kinase-dead knock-in mice, were resistant to TNF-α-induced necroptosis, where RIPK1 functions as a kinase to activate RIPK3 and drive necrotic cell (see, FIG. 10B).

Figure 10A:
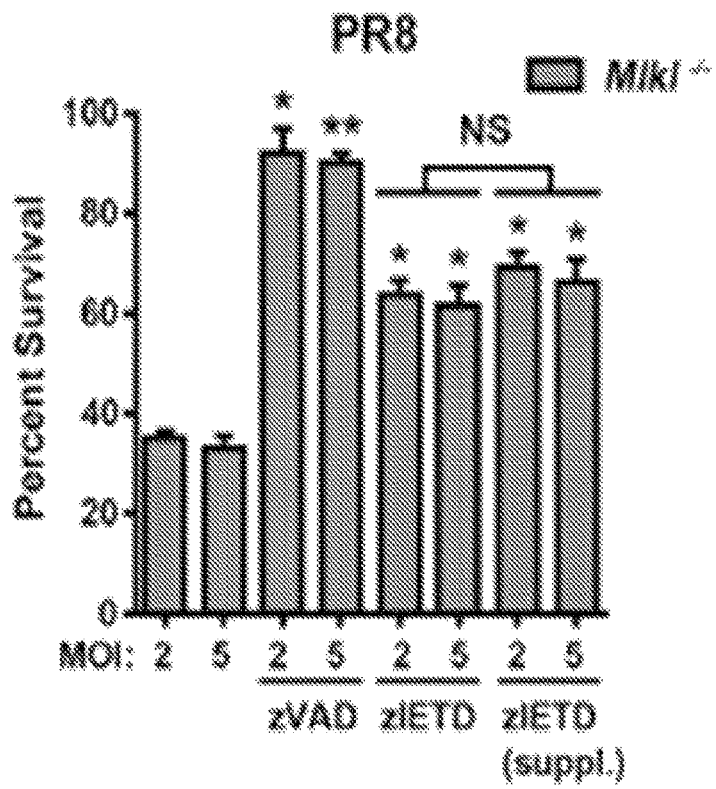
FIGS. 10A through 10D show RIPK1 mediates RIPK3-dependent apoptosis in IAV-infected cells.
Figure 10B:
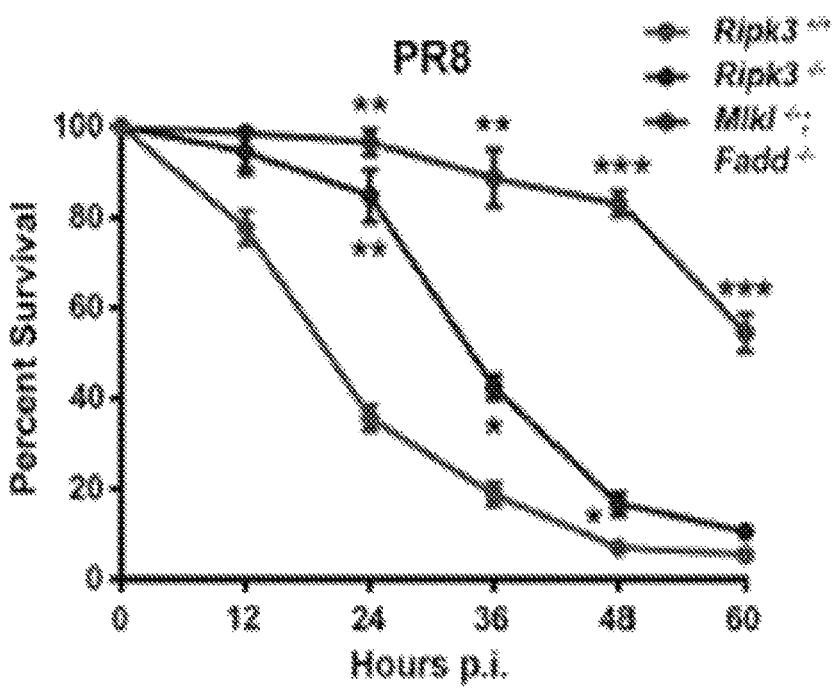
Figure 10C:
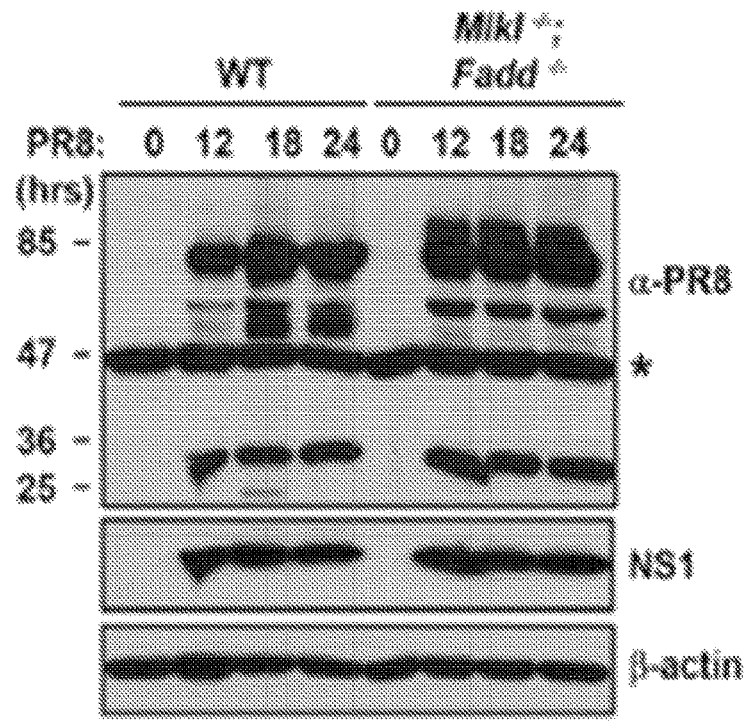
Figure 10D:
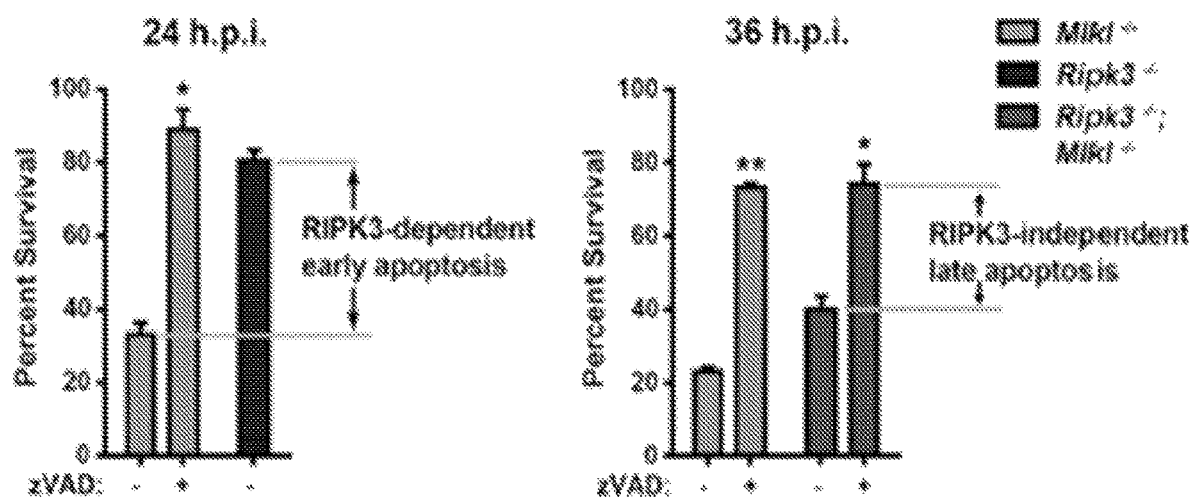

In accordance with these findings, IAV-induced phosphorylation of MLKL was intact in ripk1−/− MEFs and in MEFs from RIPK1 kinase-dead knock-in (ripk1d138n/d138n) mice, while caspase 8 activity was selectively lost in ripk1−/− MEFs, and not in MEFs expressing kinase-dead RIPK1 (see, FIG. 10C). Subsequent immunoprecipitation experiments revealed that PR8-induced association of FADD with RIPK3 was dependent on RIPK1 (see, FIG. 10D), placing RIPK1 upstream of FADD and functionally implicating RIPK1 as a kinase-independent adaptor protein that links RIPK3 to FADD and caspase 8 during IAV-activated apoptosis.

Figure 11A:
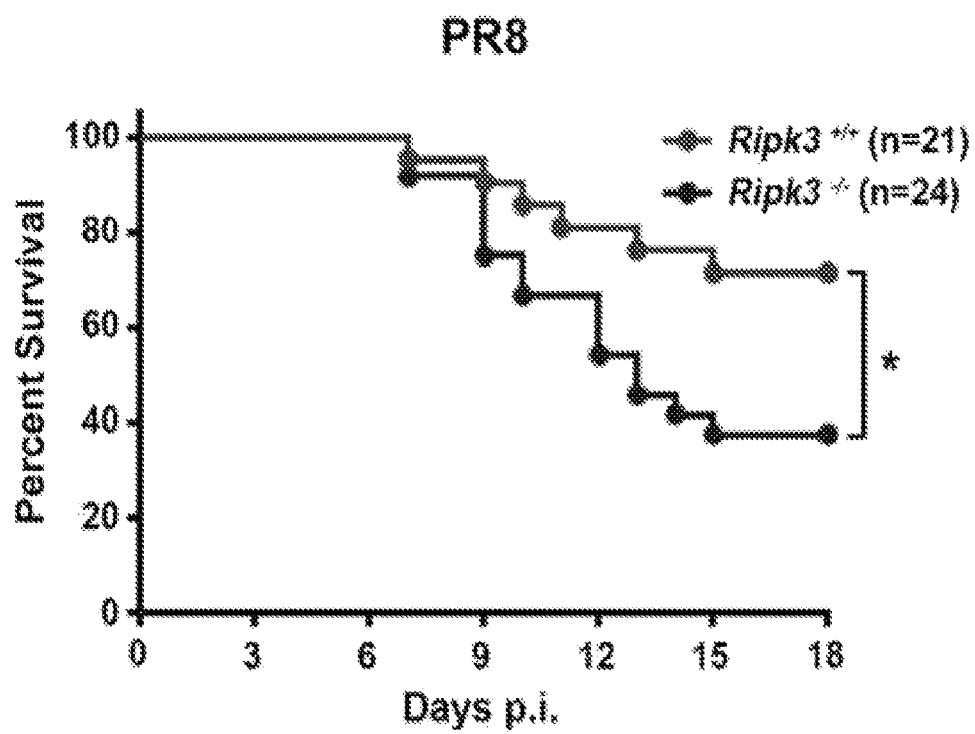
FIGS. 11A through 11G show RIPK3-activated necroptosis and apoptosis pathways are both required for protection against IAV in vivo.
Figure 11B:
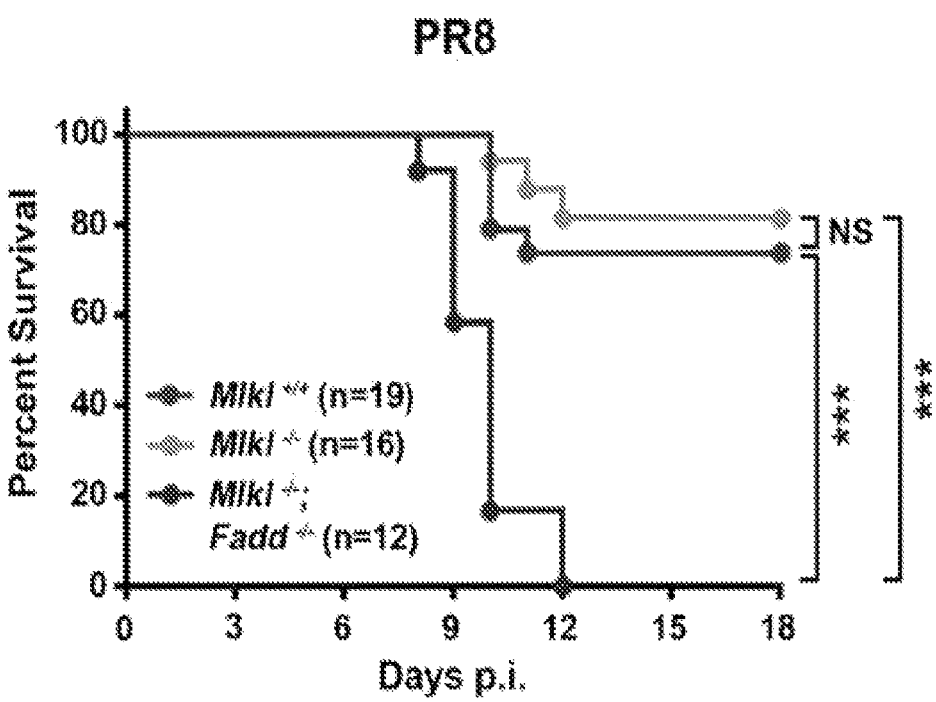
Figure 11C:
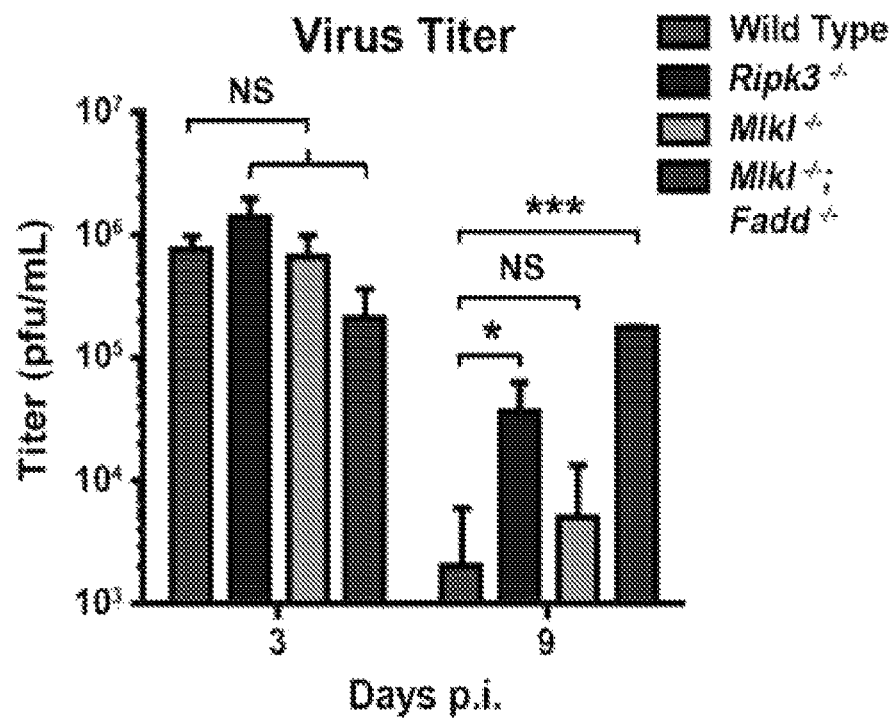

MLKL- and FADD-driven arms of RIPK3-mediated cell death functionally overlap in protecting against lethal IAV infection in vivo. To examine the effect of RIPK3 deficiency on the host response to respiratory infection with IAV, cohorts of ripk3−/− mice, alongside their age- and sex-matched wild-type controls, were inoculated with PR8 and their survival over a time course of 18 days was monitored. It was observed that 25% of wild-type (ripk3+/+) controls succumbed to PR8 by 15 d.p.i.; mice surviving past this time point recovered fully. Loss of ripk3 resulted in significantly increased lethality (p<0.05), with 60% of ripk3−/− mice succumbing to PR8 in the same time frame (see, FIG. 11A). When progeny virion production in infected mice was examined, no notable difference in virus output on day 3 p.i. was found, but ~10-fold more virus in the lungs of ripk3−/− mice than those of control animals on day 9 p.i. was observed (see, FIG. 11C).

To identify the relative contributions of MLKL-mediated necroptosis versus FADD-induced apoptosis downstream of RIPK3 in control of IAV in vivo, wild-type (mlkl+/+), mlkl−/−, and mlkl−/−fadd−/− double knock-out mice were next infected with PR8 and their survival over 18 days was monitored. Fadd−/− mice are known to die in utero and were not tested. The mlkl−/− mice were not any more susceptible to IAV than their wild-type counterparts and the majority (~75%) of these mice survived this dose of PR8 to recover fully from infection (see, FIG. 11B). In agreement with these findings, mlkl−/− mice did not differ significantly from wild-type animals in lung progeny virion output either early (day 3) or late (day 9) post-infection (see, FIG. 11C). Mice doubly-deficient in MLKL and FADD, however, were extremely susceptible to IAV-induced lethality, with none surviving past day 12 p.i (see, FIG. 11B). These mice were also severely compromised in their capacity to limit IAV replication; although virus titers from infected mlkl−/−fadd−/− lungs were similar to those seen in wild-type animals early in infection, these titers did not drop during the resolution phase (day 9) of infection, remaining ~20-100-fold higher than levels observed in controls (see, FIG. 11C).

Figure 11D:
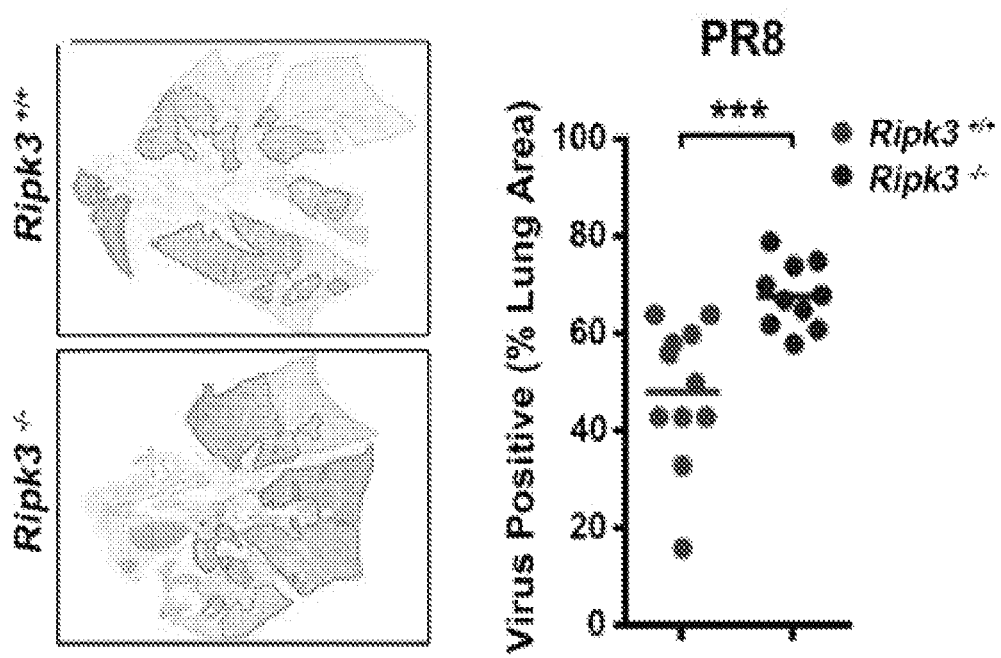
Figure 11E:
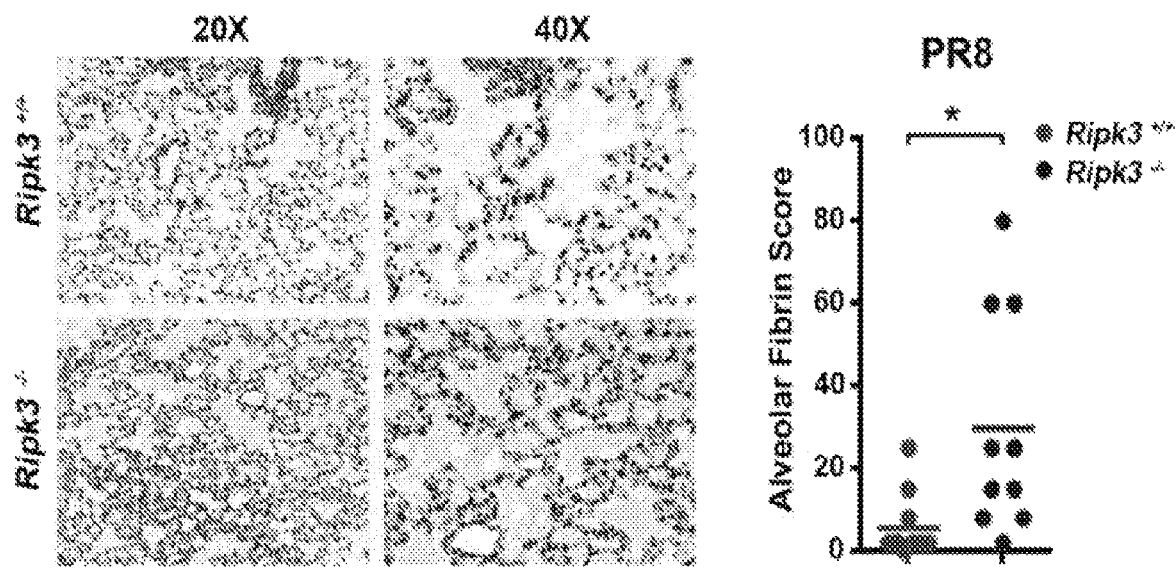

To explore the basis for the elevated mortality of ripk3−/− mice, histological analyses were performed on lungs 6 d.p.i. Lung sections were stained with anti-IAV antibody to determine the extent of infection and with hematoxylin/eosin to assess lesion severity. Compared to ripk3+/+ littermate controls, ripk3−/− lungs exhibited a significant increase in virus spread within the infected lung (see, FIG. 11D), consistent with our observations that ripk3−/− mice fail to effectively control IAV progeny virion production (see, FIG. 6C). Substantial pulmonary edema and an increase in alveolar fibrin deposition in ripk3−/− lungs was noted, indicative of severe damage to the capillaries and alveoli in these animals (see, FIG. 11E). Deposition of fibrin around the alveoli of infected ripk3−/− lungs is likely indicative of a 'cytokine storm'-driven inflammatory response to increased virus spread within lung tissue.

Figure 11F:
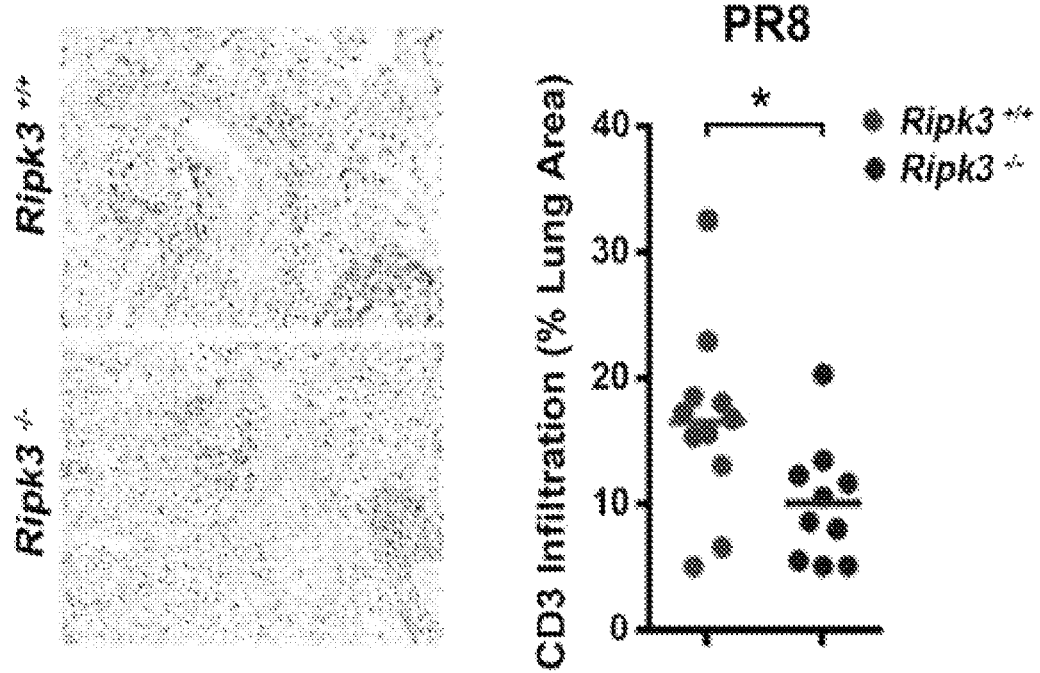
Figure 11G:
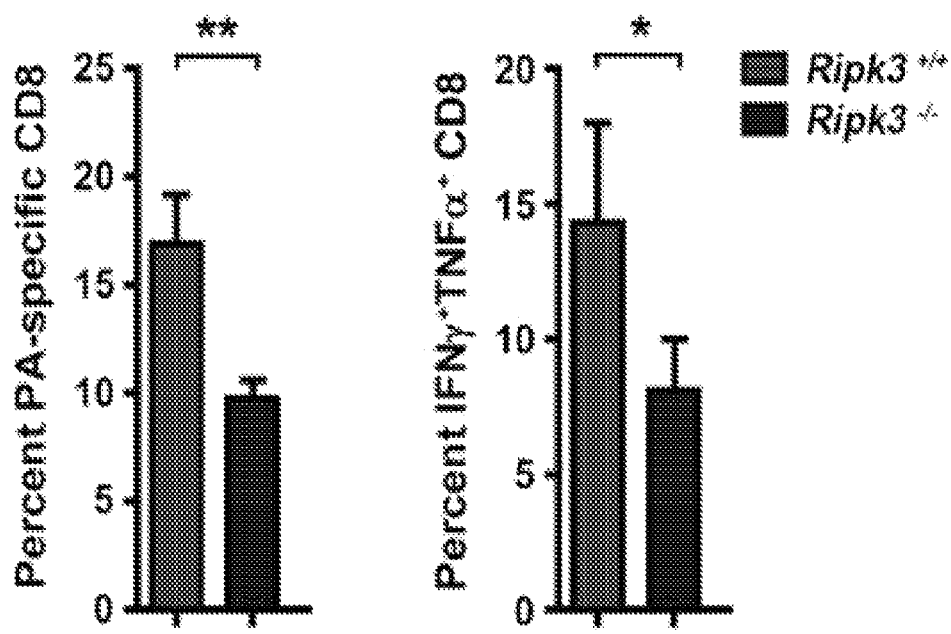

As RIPK3 can also drive immune responses, we examined the effect of RIPK3 loss on the recruitment of T cells to the infected lung. Lungs from ripk3−/− displayed a markedly reduced infiltration of CD3+ cells, compared to ripk3+/+ controls, 6 d.p.i. (see, FIG. 11F). To examine this effect in greater detail, the abundance of JAY-specific CD8+ T cells in bronchioalveolar lavage (BAL) fluid were measured 9 d.p.i., and it was found that IAV-specific CD8+ T cell numbers were significantly diminished in ripk3−/− mice (see, FIG. 11G, left). Moreover, responding ripk3−/− CD8+ T cells appeared less capable of mounting an efficient effector response, as evidenced by the lower frequencies of polyfunctional (IFN-γ+TNF-α+) CD8+ T cells in BAL fluid of ripk3−/− mice, compared to ripk3+/+ controls (see, FIG. 11G, right). Collectively, these findings denote that loss of RIPK3 results not only in increased IAV spread within the infected lung, but also in diminished antiviral CD8+ T cell responses to the infection.

Example 3: Determination of DAI Sensitization of Influenza a Virus to Activate RIPK3-Dependent Cell Death: Materials and Methods Mice and Cells. Zbp1−/−, Ripk3−/−, ripk1−/− and ripk3−/− mice were housed in SPF facilities in house, and all in vivo experiments were conducted under protocols approved by a Committee on Use and Care of Animals. All primary mouse embryo fibroblasts (MEFs) were generated in-house from E14.5 embryos and used within five passages in experiments. For stable reconstitution studies, zbp1−/− MEFs immortalized by SV40 Large T antigen were infected with retroviruses expressing DAI mutants from the pQCXIH vector (Clontech). All cells were cultured in high-glucose Dulbecco's Modified Eagle Medium (DMEM) supplemented with 10-15% heat-inactivated fetal bovine serum (Hyclone) and antibiotics.

Reagents. Biological and chemical reagents were from the following sources: cycloheximide (MP Biomedicals), zVAD.fmk (Bachem), interferon-β (PBL), and TNF-α (R&D systems). Antibodies to β-actin (Sigma), caspase 8 (Cell Signaling), cleaved caspase 8 (Cell Signaling), FADD (Millipore), IAV NS1 (Santa Cruz), MLKL (Abgent or Millipore), p-MLKL (Abcam), RIG-I (Enzo), PKR (Santa Cruz), RIP1 (BD Transduction lab), RIP3 (ProSci or Santa Cruz), STAT1 (BD Transduction labs), and p-STAT1 (Cell Signaling) were obtained from the indicated commercial sources. Secondary anti-mouse, -rabbit, and -rat IgG were purchased from Jackson ImmunoResearch.

Viruses and Virus Infections. Influenza virus A/Puerto Rico/8/34 (PR8) was generated by reverse genetics. All IAV and influenza type B (IBV) strains were propagated by allantoic inoculation of embryonated hen's eggs with diluted (1:106) seed virus. Virus titers were determined as 50% egg infectious dose ($EID_{50}$). For in vivo studies, recombinant PR8-GFP virus was provided. Mice were anesthetized with isofluorane and infected i.n. with virus inoculum diluted in 30 µL of endotoxin-free phosphate-buffered saline (PBS). Mice were either monitored for survival and weight-loss over a period of 18 days or sacrificed at defined time points for analysis of histology and virus replication. Mice losing >35% body-weight were considered moribund and euthanized by $CO_2$ asphyxiation. To determine progeny virus production in infected mice, lung homogenates were titered by plaque assay on Madin-Darby Canine Kidney cells.

Molecular Modeling. The murine DAI Zα2:zRNA complex was modeled based on the template of human ADAR Zα1 bound to zRNA (PDB code 2GXB, 33% identity, 53% similarity). DAI Zα2 was aligned with the HHpred portion of the MPI bioinformatics Toolkit, and a model built using MODELLER. Two mouse DAI Zα2 domains were superposed on the corresponding domains of the ADAR Zα structure with RNA using the UCSF Chimera software and the zRNA co-ordinates were copied over to make the final model. Side chain rotamers were also considered using the SCWRL4 frame option to account for steric packing to RNA.

Purification and Analysis of DAI-Associated IAV RNA. HEK 293T cells seeded in 10 cm dishes and transfected with FLAG-tagged RIG-I or DAI constructs for 24 hours were infected with PR8 (MOI=2) for 12 hours and disrupted in 1 mL lysis buffer (50 mM HEPES, 150 mM KCl, 2 mM EDTA, 1 mM NaF, 0.5% NP40, 0.5 mM DTT, protease inhibitor cocktail, 25 units RNasin). An aliquot (5%) of lysate was saved for total RNA input control and immunoblot analysis. Lysates were then incubated with 30 µL/sample anti-FLAG agarose bead slurry (Clone M2, Sigma-Aldrich) overnight with rotation at 4° C. Beads were collected by centrifugation, washed ten times with NT2 buffer (50 mM Tris pH 7.4, 150 mM NaCl, 1 mM $MgCl_2$, 0.05% NP40), resuspended in 250 µL of DNase digestion buffer (40 mM Tris pH 8.0, 10 mM $MgSO_4$, 1 mM $CaCl_2$) and treated with 25U RNasin (Promega) and 2U DNAse I (NEB) at 37° C. for 20 minutes. Beads were collected by centrifugation, washed with NT2, and resuspended in 100 µL NT2 buffer. 10% of each sample was removed for immunoblot analysis. Samples were treated with 4 units proteinase K at 55° C. for 30 minutes. 1 mL Tri-reagent (Sigma-Aldrich) was added to each sample, and RNA was harvested according to the manufacturer's instructions. For RNA Seq analyses, RNA was prepared using the TruSeq Stranded Total RNA Library Prep Kit (Illumina) Briefly, total RNA was depleted of ribosomal RNA (rRNA-removal beads), fragmented, and reverse transcribed into cDNA using reverse transcriptase and random primers. Following second strand cDNA synthesis by DNA Polymerase I in the presence of RNase H, an adenine was added to the 3'-end and specific Illumina adapters were ligated to cDNAs. The ligation products were purified and enriched by PCR to create the final cDNA library, which was loaded on the MiSeq platform (Illumina). Bowtie2 was used to map reads to the PR8 genome. For PCR detection of DI particle genomes, RNA was reverse transcribed into cDNA using reverse transcriptase (SuperScript® II RT, ThermoFisher) with a universal genomic viral RNA (vRNA) primer (5'-AGCAAAAGCAGG-3') (SEQ ID NO:18), per manufacturer's instructions. PCR was then performed using the following primers PB2: 5'-ATGGAAAGAATAAAAGA ACTAAG-3' (SEQ ID NO:19), and 5'-CTAATTGATGGC-CATCCGAATTC-3' (SEQ ID NO:20).

Figure 12A:
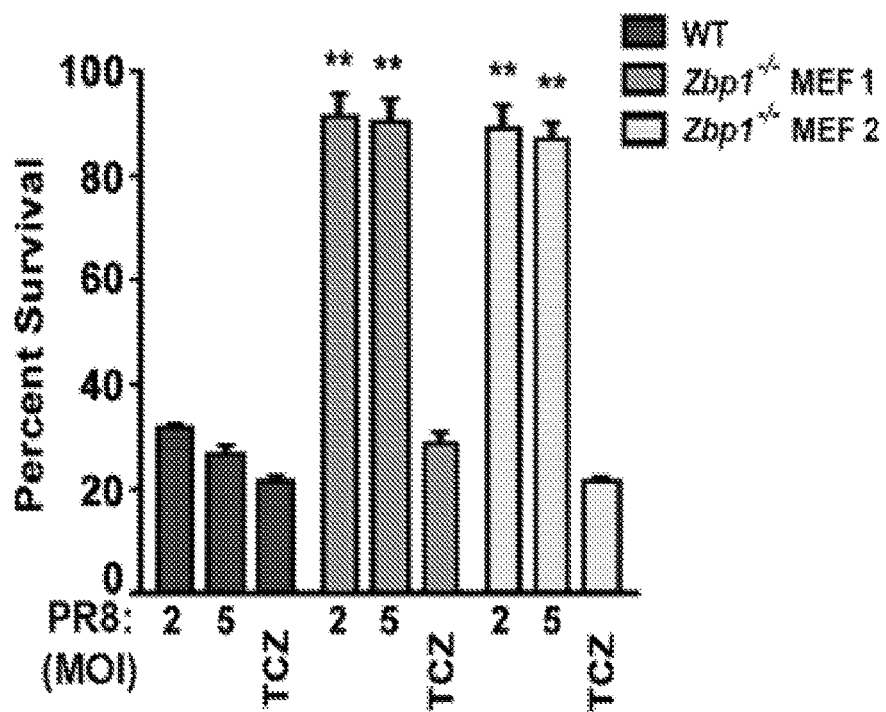
FIGS. 12A through 12G show DAI is essential for IAV-induced cell death in MEFs and airway epithelial cells.
Figure 12B:
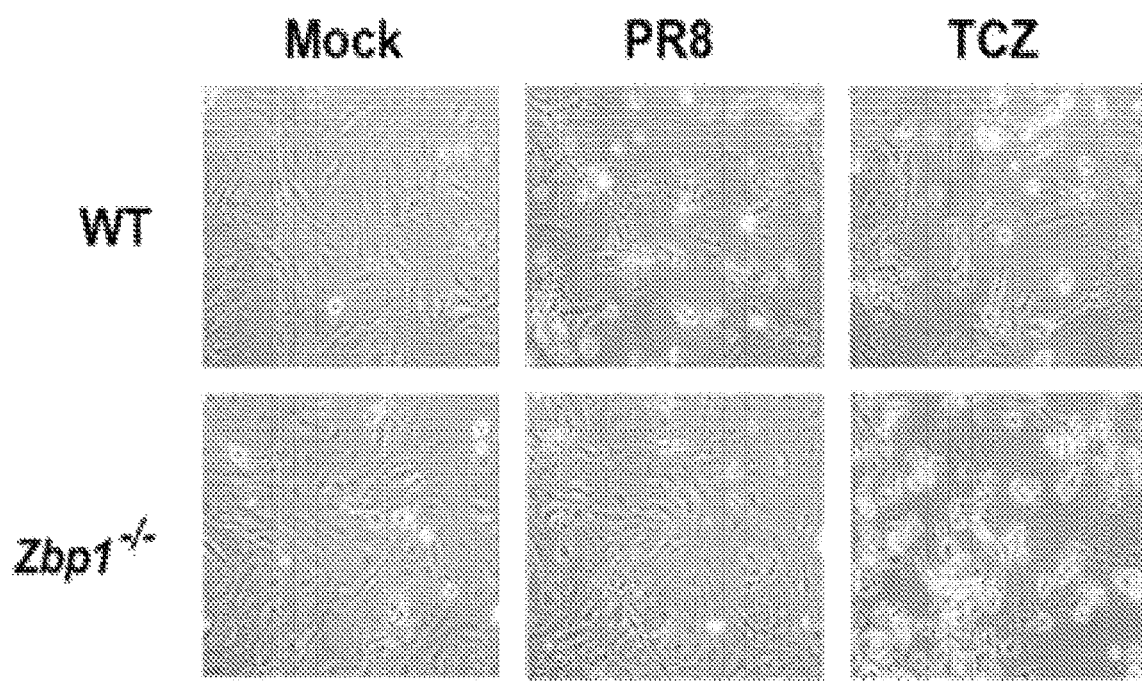
Figure 12C:
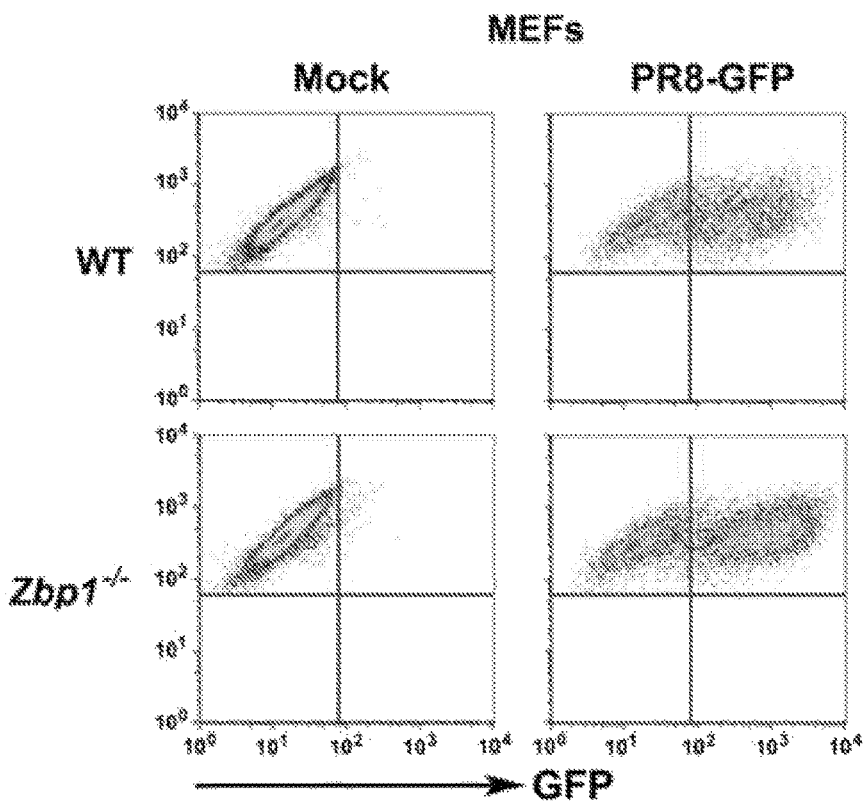
Figure 12D:
Figure 13A:
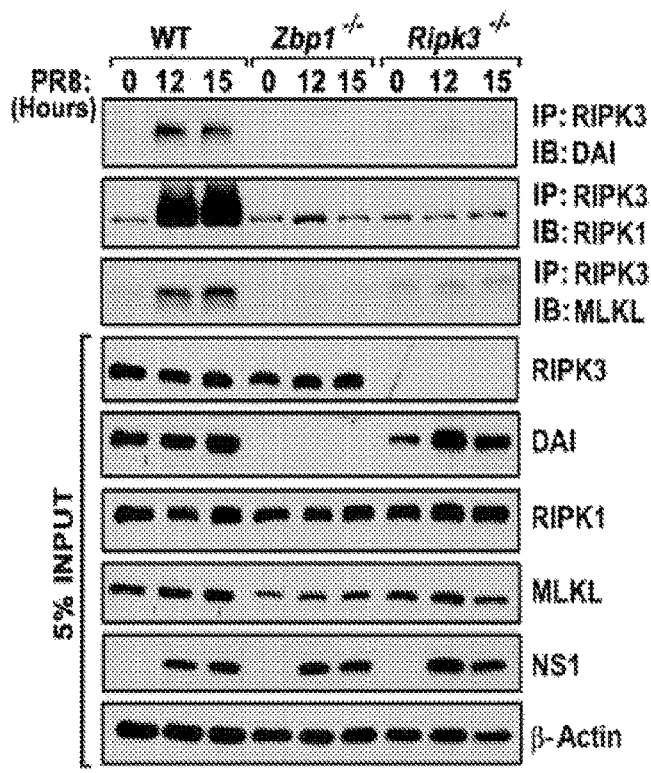
FIGS. 13A through 13F show DAI is required for IAV induced formation of RIPK3-containing necrosome complex.
Figure 13B:
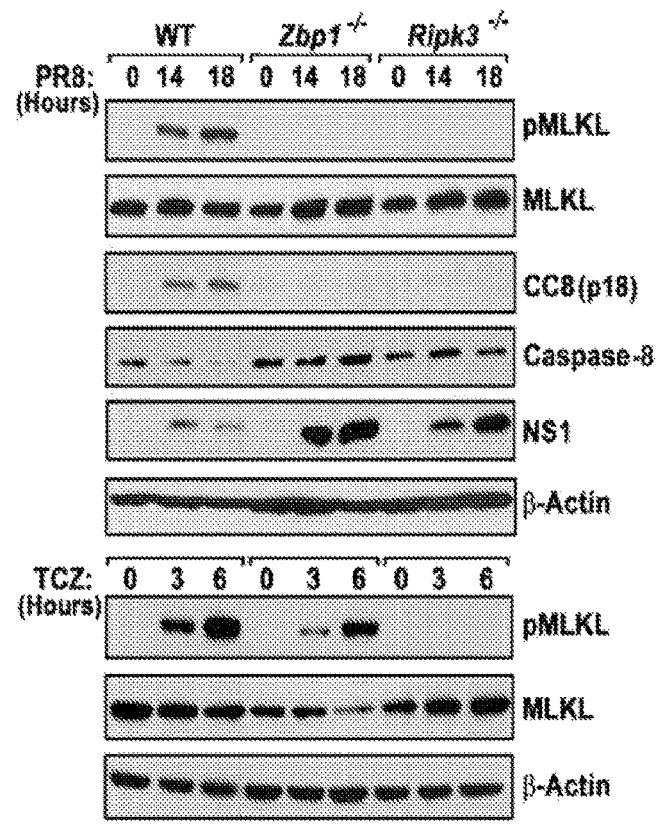
Figure 13C:
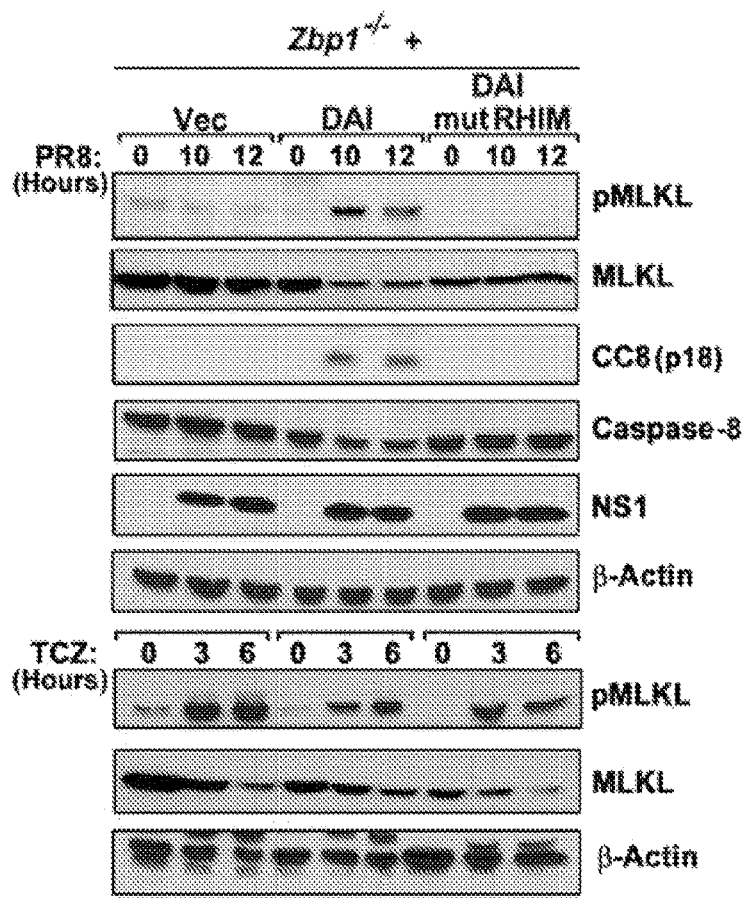
Figure 13D:
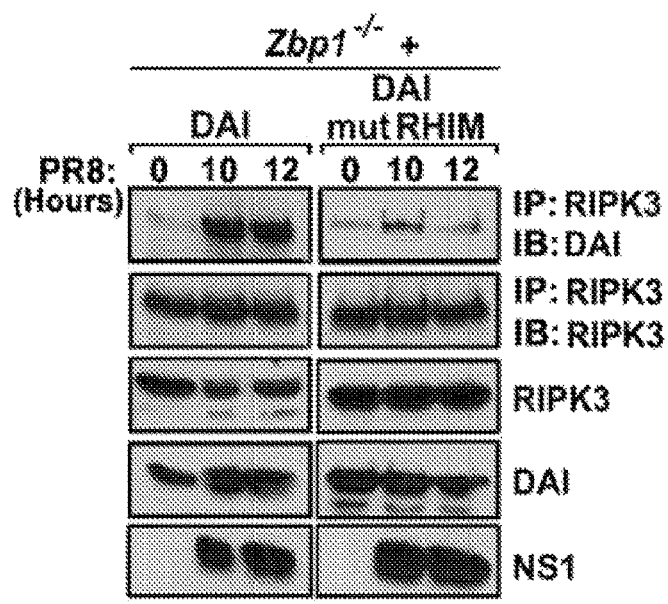

Example 4: Determination of DAI Sensitization of Influenza a Virus to Activate RIPK3-Dependent Cell Death: Experimental Results DAI is required for IAV-induced cell death. In a focused screen for mediators of IAV-activated cell death, it was observed that MEFs from DAI-deficient ($zbp1^{-/-}$) mice were extraordinarily resistant to death triggered by this virus. When evaluated over a period of 24 hours, near-confluent monolayers of primary, early-passage MEFs from two separately-housed $zbp1^{-/-}$ colonies uniformly displayed >90% viability when infected with IAV strain A/Puerto Rico/8/1934 (PR8, H1N1) while similarly-infected wild-type (C57BL/6) control MEFs manifested extensive cytopathic effect (CPE) and cell death by this time (see, FIGS. 12A and 12B). Notably, $zbp1^{-/-}$ MEFs were also resistant to cell death activated by seasonal H1N1 and H3N2 strains of IAV, as well as to IBV (see, FIG. 16A), although these cells displayed levels of death effector proteins equivalent to controls (see, FIG. 16B), and remained susceptible to necroptosis induced by TNF-α (see, FIG. 12A). IAV entry, as measured by GFP-positivity 18 h.p.i. with recombinant PR8 expressing GFP (PR8-GFP), was equivalent between wild-type and $zbp1^{-/-}$ MEFs (see, FIG. 12C). Virus proteins NP and NS1 were also produced at similar levels and with similar kinetics in PR8-infected wild-type and $zbp1^{-/-}$ MEFs (see, FIG. 13D), arguing against a non-permissive cellular environment or diminished virus replication as responsible for survival of IAV-infected $zbp1^{-/-}$ MEFs.

Figure 12E:
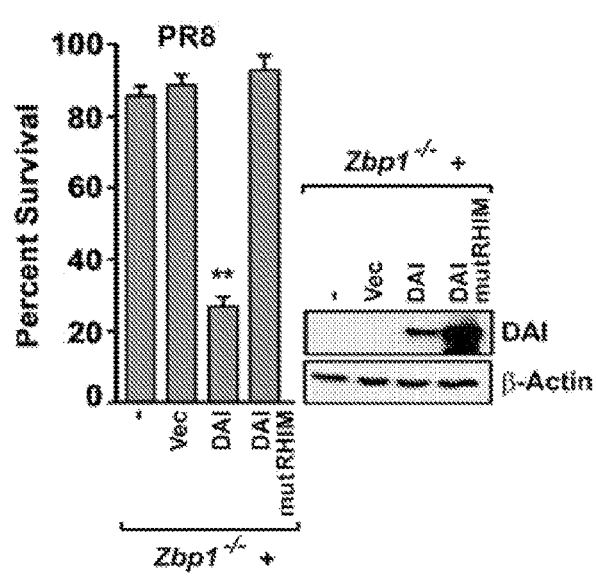
Figure 12F:
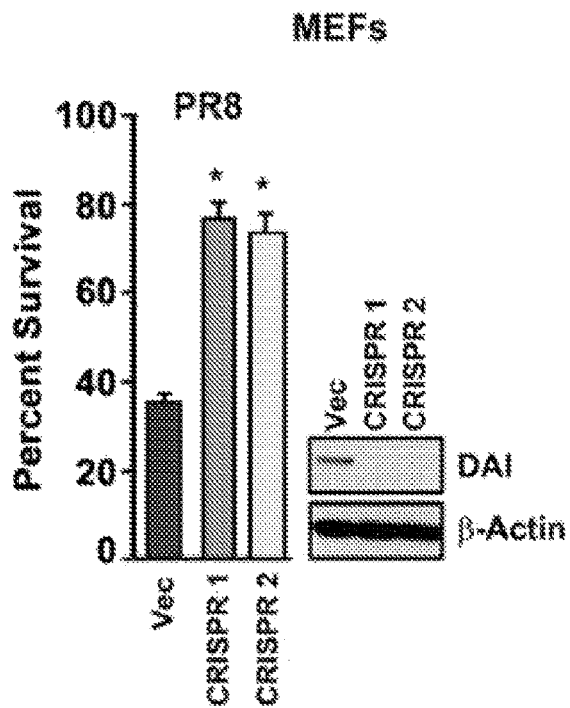
Figure 12G:
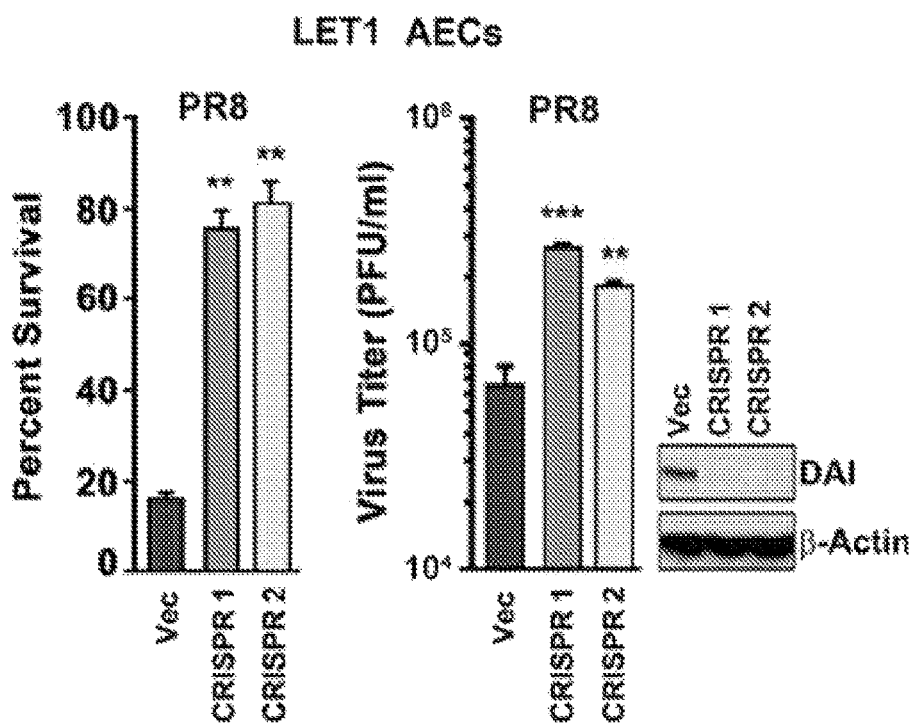

To confirm a role for DAI in induction of cell death following IAV infection, immortalized $zbp1^{-/-}$ MEFs were reconstituted with either full-length DAI, or with a mutant of DAI (DAI mutRHIM), carrying a tetra-alanine substitution of the core RHIM sequence IQIG (aa 192-195), analogous to a human DAI mutant incapable of RHIM-based interactions. While immortalized $zbp1^{-/-}$ MEFs were resistant to IAV-induced cell death, reintroduction of full-length wild type DAI, but not DAI mutRHIM, into these cells fully restored susceptibility to IAV (see, FIG. 12E). In a corollary experiment CRISPR/Cas9-based ablation of zbp1 expression in wild-type MEFs rendered these cells resistant to IAV-induced cell death (see, FIG. 12F). In neither case was susceptibility to TNF-α-induced necroptosis affected (see, FIGS. 16C and 16D).

To extend these findings to a cell type relevant to IAV replication in vivo, zbp1 expression wad ablated in LET1 cells before they were infected with IAV. The LET1 cell line is derived from type I alveolar epithelium, a primary early target of IAV in the lung. LET1 cells, unlike MEFs, support the complete IAV lifecycle, and produce progeny virions upon infection. It was previously observed that ablating ripk3 in these cells protects them from IAV induced cell death, allows unbridled virus replication, and increases progeny virion output. It has now been observed that ablating zbp1 in LET1 cells is similarly protective against cell death and supportive of increased productive virus replication: two distinct sgRNAs to murine zbp1 both reduced IAV-triggered cell death by ~70% in LET 1 cells (see, FIG. 13G), comparable to the protection afforded by ablation of ripk3 itself. Notably, LET1 cells in which zbp1 was ablated, unlike cells lacking ripk3, were still susceptible to TNF-α-induced necroptosis (see, FIG. 16E), underscoring the specific requirement for DAI in IAV, but not TNF-α, induced RIPK3-driven cell death in this cell type as well. LET1 cells lacking zbp1 produced significantly more progeny IAV that LET1 controls over a 30 hour timeframe, suggesting that these cells had become 'factories' for virus replication (see, FIG. 12H).

DAI associates with RIPK3 and mediates both apoptosis and necroptosis in IAV-infected cells. IAV, uniquely among viruses studied thus far, activates both apoptosis and necroptosis downstream of RIPK3. It does so by nucleating a RIPK3-containing necrosome complex that also comprises MLKL, which mediates necroptosis, as well as RIPK1 and FADD, which activate apoptosis. To test if DAI was required for necrosome assembly and consequent dual activation of apoptosis and necroptosis downstream of RIPK3, RIPK3 was immunoprecipitated from IAV-infected wild-type and zbp1$^{-/-}$ MEFs, and precipitates were examined for the presence of DAI, RIPK1, and MLKL. As negative controls, ripk3$^{-/-}$ MEFs were included in these experiments. It was found that IAV infection induced the robust association of DAI with RIPK3, and that DAI was essential for recruitment of both MLKL and RIPK1 to RIPK3 (see, FIG. 13A). zbp1$^{-/-}$ MEFs were completely defective in both MLKL and caspase-8 activation upon IAV infection (see, FIG. 13B), although necrosome assembly (not shown) and activation of MLKL (see, FIG. 13B) in response to TNF-α occurred normally in the absence of DAI. LET1 cells in which expression of zbp1 was ablated by CRISPR/Cas9 gene-targeting also failed to support either MLKL or caspase-8 activation flowing infection by IAV, although activation of MLKL by TNF-α was unaffected (see, FIG. 17). Loss of RIPK3, expectedly, resulted in abolishment of MLKL activation in both MEFs and LET1 cells following either infection by IAV or exposure to TNF-α (see, FIGS. 14B and 17). Reintroduction of wild type DAI, but not DAI mutRHIM, into immortalized zbp1$^{-/-}$ MEFs restored both phosphorylation of MLKL and cleavage of caspase-8 in response to IAV (see, FIG. 13C). In accordance with these findings, wild type DAI, but not DAI mutRHIM, robustly complexed with RIPK3 following IAV infection (see, FIG. 13D). Together, these results demonstrate that DAI lies upstream of RIPK3 in the pathways leading to activation of MLKL and caspase-8, and requires its RHIM to associate with RIPK3 and activate these pathways.

Figure 13E:
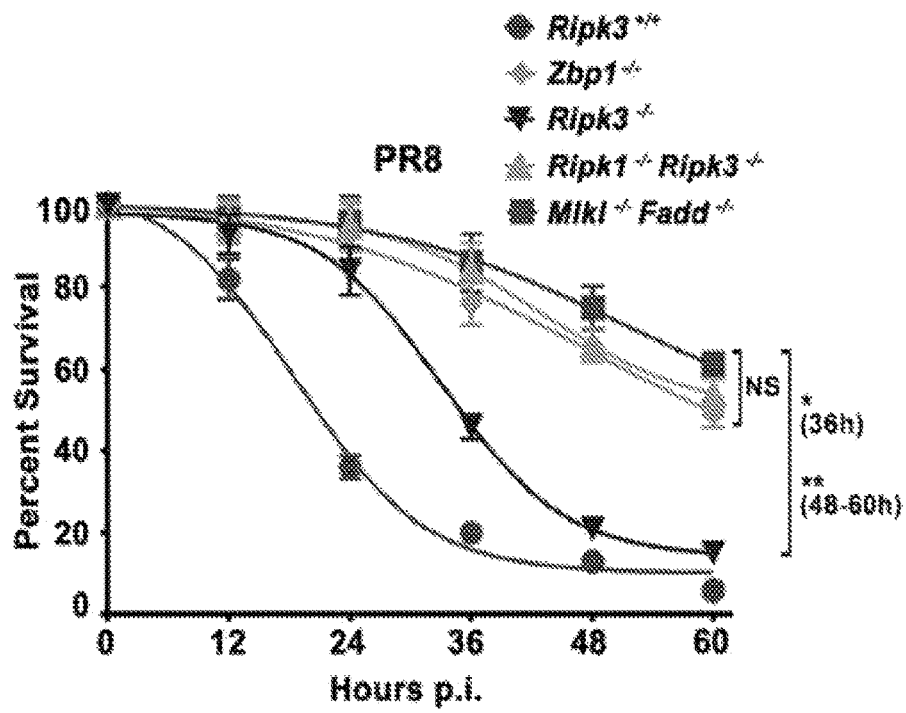
Figure 13F:
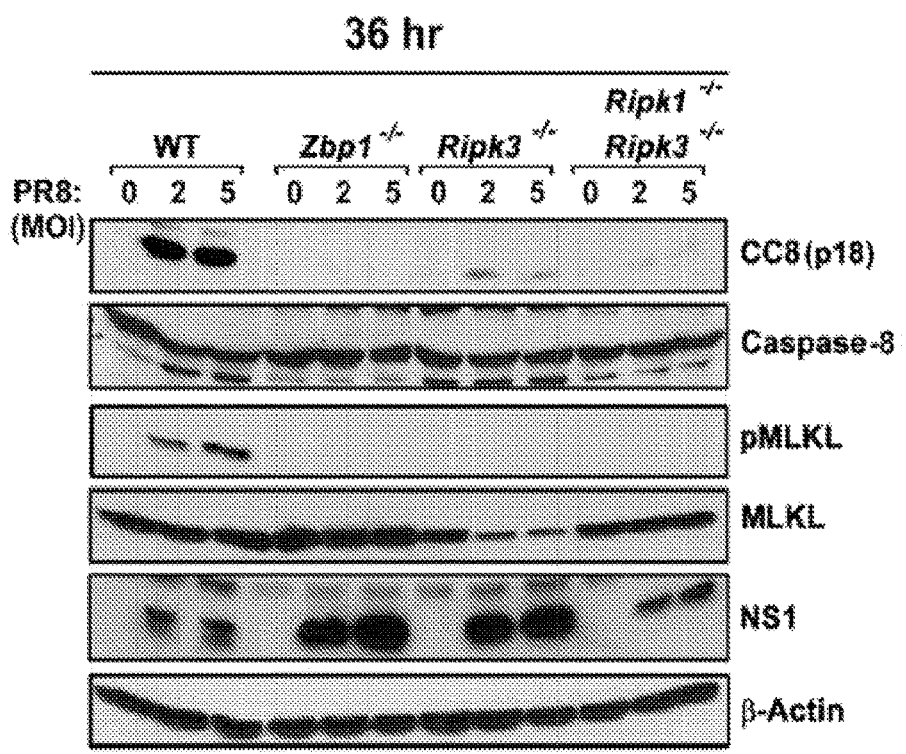

It was previously shown that IAV activates a delayed RIPK3-independent pathway of apoptosis that relies on FADD and caspase-8 and is activated between 24-36 h.p.i. Cells doubly-deficient in RIPK3 and FADD, RIPK3 and caspase-8, or MLKL and FADD, continue to survive past 36 hours, whereas >50% of ripk3$^{-/-}$ MEFs are dead by this time point. In fact, these double knockout MEFs (e.g., fadd$^{-/-}$mlkl$^{-/-}$ MEFs) survive for up to 60 h.p.i without any obvious abatement of virus replication, while ripk3$^{-/-}$ MEFs are mostly dead by 48 h.p.i. It was observed that zbp1$^{-/-}$ were significantly more resistant to IAV than ripk3$^{-/-}$ MEFs, phenocopying in this regard the resistance of MEFs doubly-deficient in apoptosis and necroptosis pathways (see, FIG. 13E) and suggesting that DAI may lie upstream of RIPK3-independent apoptosis as well.

It was hypothesized that, when RIPK3 is absent, DAI may instead employ RIPK1 as a RHIM-containing adaptor to link replicating IAV to FADD and caspase-8; thus, co-ablation of RIPK1 with RIPK3 will be needed to abrogate all major pathways of IAV-triggered programmed cell death. To test this idea, the kinetics of IAV-induced cell death were evaluated in ripk1$^{-/-}$ ripk3$^{-/-}$ double knockout MEFs, and it was found that these cells were as resistant to IAV as zbp1$^{-/-}$ MEFs and fadd$^{-/-}$mlkl$^{-/-}$ double knockout MEFs, each of which survived IAV beyond 36 h.p.i. (see, FIG. 13E). Moreover, delayed caspase-8 activity seen in ripk3$^{-/-}$ MEFs and completely absent in zbp1$^{-/-}$ MEFs was largely abolished in ripk1$^{-/-}$ripk3$^{-/-}$ double knockout MEFs (see, FIG. 13E). Thus, DAI also mediates IAV-activated RIPK3-independent apoptosis, likely via recruitment of RIPK1 and activation of a RIPK1-FADD-caspase-8 axis.

Figure 14A:
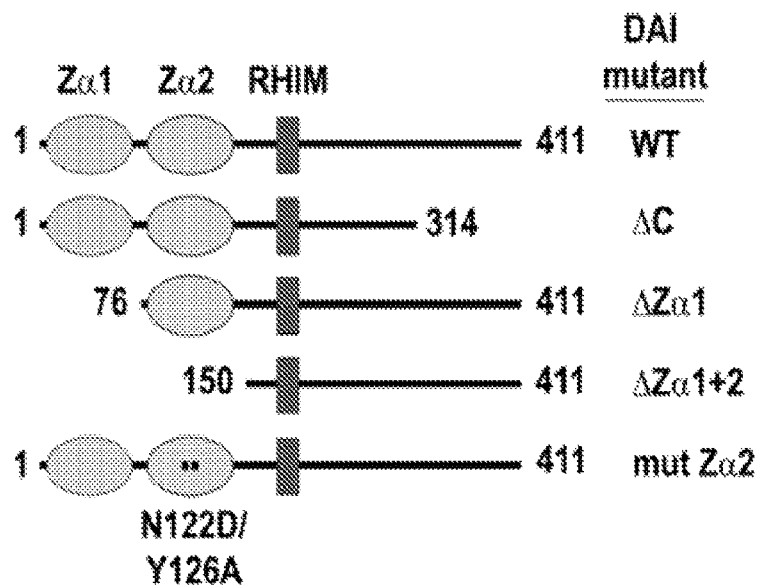
FIGS. 14A through 14E show DAI senses IAV RNA.

DAI senses IAV RNA. The results are believed to establish an absolute and specific role for DAI in RIPK3-driven cell death responses to IAV, but do not clarify if DAI functions at the level of RIPK3 (as a co-factor needed for its activation) or if it operates upstream of RIPK3. In the latter scenario, DAI, a nucleic acid binding protein, may directly sense IAV nucleic acids produced during viral replication and link proliferating IAV to RIPK3. To distinguish between these alternatives, a mutagenesis approach aimed at identifying regions of DAI required for activation of RIPK3 and induction of cell death was undertaken. DAI possesses two tandem Zα domains towards its N-terminus which, for convenience, were called Zα1 (a.a. 8-72) and Zα2 (aa 84-147) (see, FIG. 14A). Zα2 is sometimes referred to as 'Zβ' in previous studies, but Zα2 is a more authentic descriptor of this domain that distinguishes it from the functionally-distinct Zβ domain of ADAR1. These domains are followed by the RHIM (aa 184-200) and a C-terminal half containing a region (aa 314-411) shown to interact with TBK-1/IRF-3 in the pathway leading to production of type I IFNs (see, FIG. 14A).

Figure 14B:
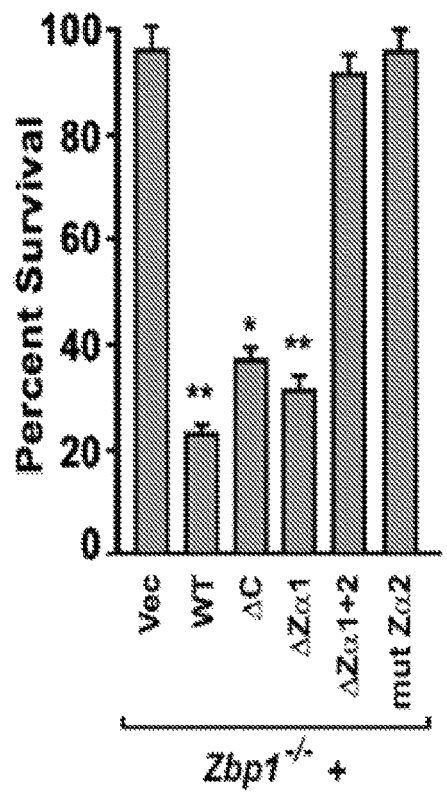
Figure 14C:
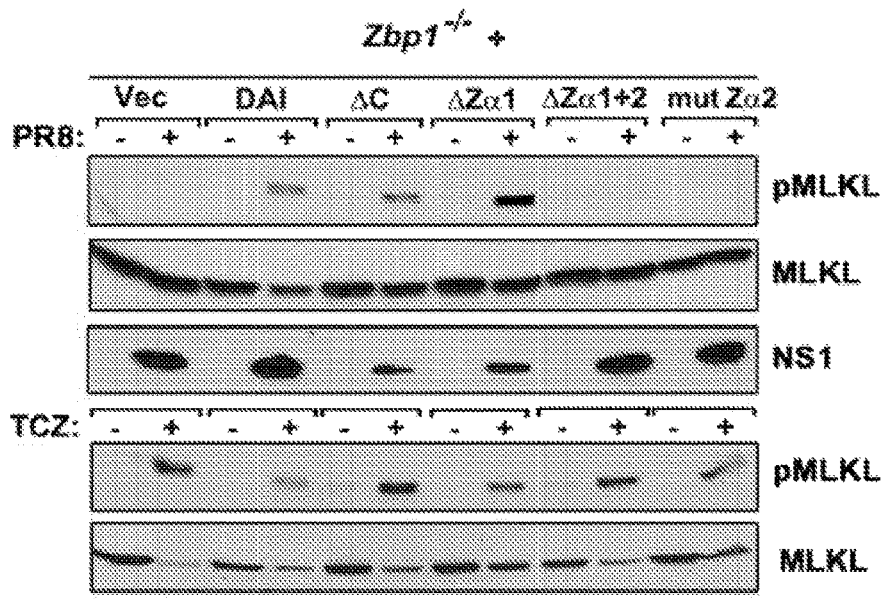

Deletion of the C-terminal TBK-1/IRF-3 binding region of DAI did not significantly impede the capacity of DAI to either trigger lysis of IAV infected cells or to activate RIPK3, as measured by phosphorylation of MLKL, in these cells (see, FIG. 14B). Similarly, singly deleting Zα1 had little effect on the magnitude of IAV-induced cell death (see, FIG. 14B) or RIPK3 activation at 24 hours (see, FIG. 14C), and only modestly affected the kinetics with which IAV killed the infected cell (see, FIG. 18A). But deleting both the Zα1 and Zα2 domains abolished cell death and RIPK3 activity.

Indeed, point mutations in two amino acids (N122 and Y126) in Zα2 of DAI, previously shown to be essential for binding to Z-DNA and analogous to residues in ADAR1 Zα known to contact Z-RNA, completely nullified the ability of DAI to induce cell death (see, FIG. 14B) or stimulate RIPK3 (see, FIG. 14C) upon IAV infection. Each of these mutants was expressed at levels comparable to wild type DAI (see, FIG. 18B), and none of the mutations affected TNF-α-induced necroptosis signaling in these cells (see, FIGS. 14C and 17C). Caspase-8 activity downstream of RIPK3, like phosphorylation of MLKL, also required Zα2 (not shown). Together, these results implicate the second Zα domain of DAI as critical for IAV-driven cell death responses, and suggest that this domain interacts with IAV RNA to initiate activation of DAI and subsequent signaling to RIPK3.

To determine if DAI bound RNA, a putative interaction between DAI Zα2 and RNA was modeled using as template the published co-crystal structures of Zα domains bound to Z-form DNA or RNA. The Zα:Z-DNA and Zα:Z-RNA structures bear remarkable similarity to each other (see, FIG. 15D, left two panels). The conserved nucleic acid residues in these structures that correspond to N122 and Y126 in the nucleic acid recognition helix of mDAI Zα2 are in identical positions, and very similar rotamers make contact with both Z-DNA and Z-RNA (see, FIG. 14D, two left panels). Correspondingly, the model of mDAI Zα2 complexed with Z-RNA strongly indicates that N122 and Y126 of mDAI Zα2 are capable of making identical contacts to either Z-form nucleic acid (see, FIG. 15D, third panel).

Figure 14D:
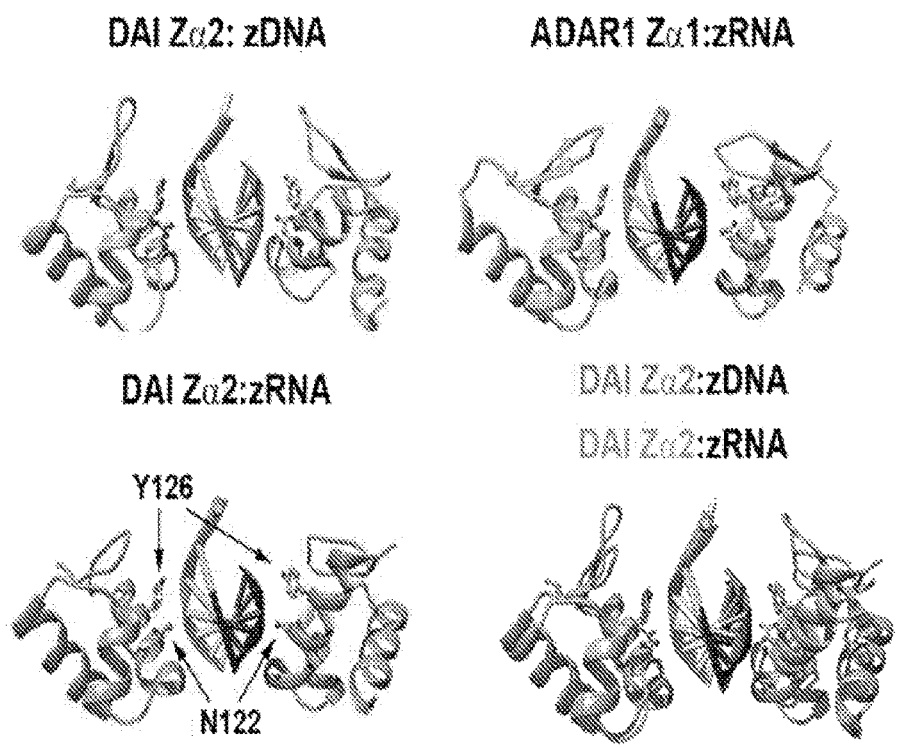

Indeed, when the mDAI Zα2:RNA model was superimposed over to the known structure of hDAI Zα2:DNA, Y126 is in an essentially identical rotamer conformation to the analogous tyrosine in hDAI Zα2:DNA, while minor differences in the position N122 relative to the analogous asparagine in hDAI positions reflect a subtle change in the confirmation of the nucleic acid recognition helix in its DNA- versus RNA-bound forms (see, FIG. 14D, fourth panel). The models are in general agreement with previous comparisons of Zα domains bound to Z-DNA or Z-RNA, indicating that the DAI Zα2 domain is similarly suited to bind either left-handed Z-form nucleic acid.

Figure 14E:
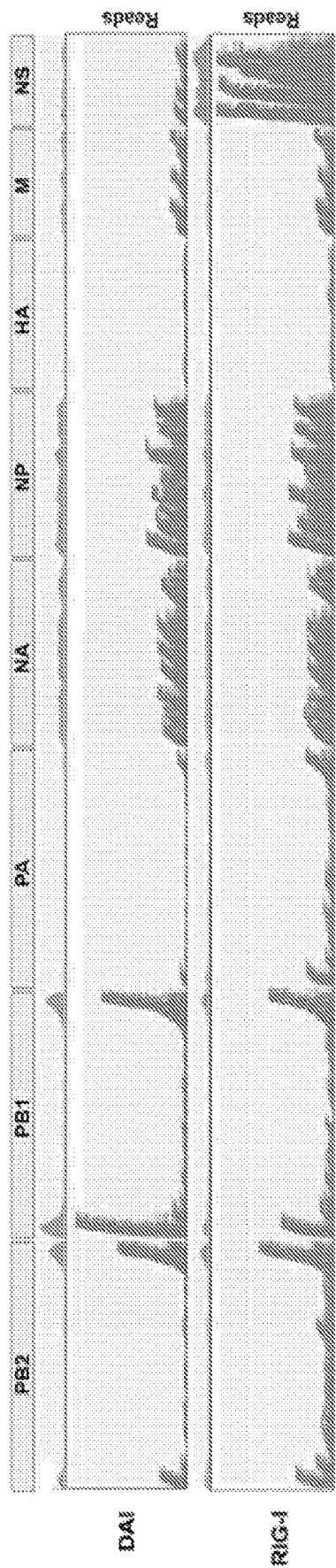

To test if DAI bound IAV RNA, and to identify these RNAs, FLAG-tagged DAI was transfected into 293T cells before these cells were infected with PR8. FLAG-affinity chromatography was then used to precipitate DAI from infected cells 12 h.p.i., eluted RNA co-precipitating with DAI, and eluates were examined for the presence of IAV RNA. In parallel, RNA co-precipitating with FLAG-RIG-I, a known sensor of IAV RNA, was also evaluated as a positive control. IAV-specific vRNA mapping to all eight IAV gene segments were readily detected in DAI immunoprecipitates (see, FIG. 14E, top), but in a manner that was neither uniform between vRNA segments, nor equivalent across each segment. Instead, bound vRNAs mapped predominantly to the 5' and 3' ends of the three longer polymerase-encoding gene segments (PB2, PB1, and PA). A significant number of reads also mapped to some of the shorter segments (e.g., NA and NP), this time more uniformly across the each individual segment, but not to others (e.g., HA). This pattern bears a resemblance to the spectrum of vRNAs co-precipitating with RIG-I (see, FIG. 14E, bottom), which was previously shown to represent IAV subgenomic material packaged into defective interfering (DI) particles.

While significant RNA yields from IAV-infected cells expressing wild-type (or mutRHIM) DAI were obtained, the amount of eluted RNA from similarly-infected cells expressing Zα2 mutants of DAI was far lower, and comparable to background yield from vector controls (see, FIG. 18D), despite equivalent expression of each FLAG-tagged DAI construct (see, FIG. 18C). Only wild-type DAI and DAI- mutRHIM, but not DAI Zα2 mutants, associated with IAV vRNA (see, FIG. 18E). Taken together, these results demonstrate that DAI binds IAV RNA in a manner requiring its Zα2 domain, and likely senses IAV RNA structures found in DI particle sub-genomes that are also recognized by RIG-I.

Figure 15A:
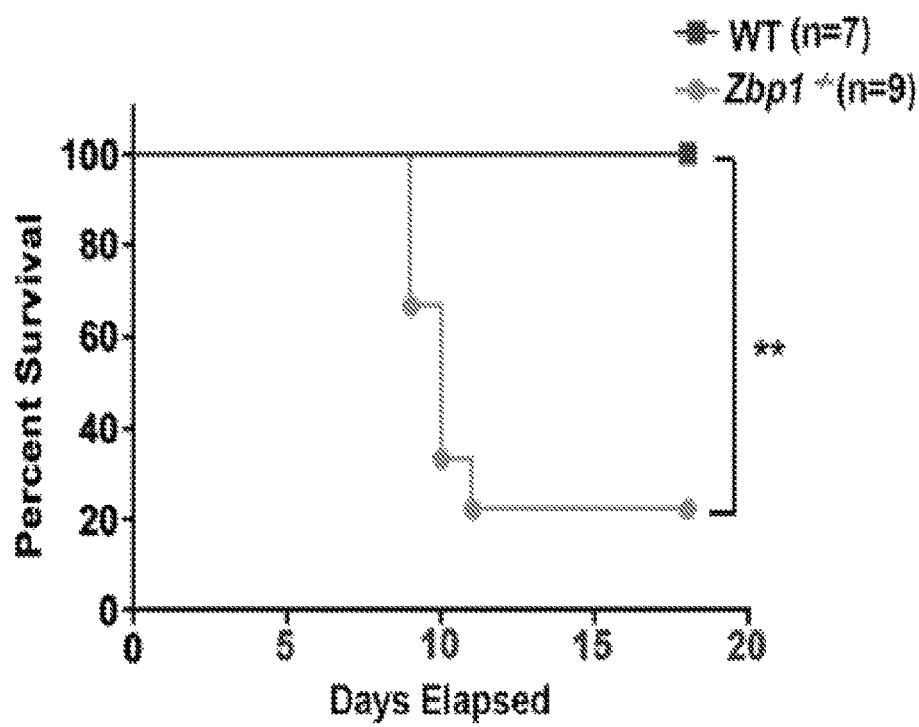
FIGS. 15A through 15E show DAI is required for protection against IAV in vivo.
Figure 15B:
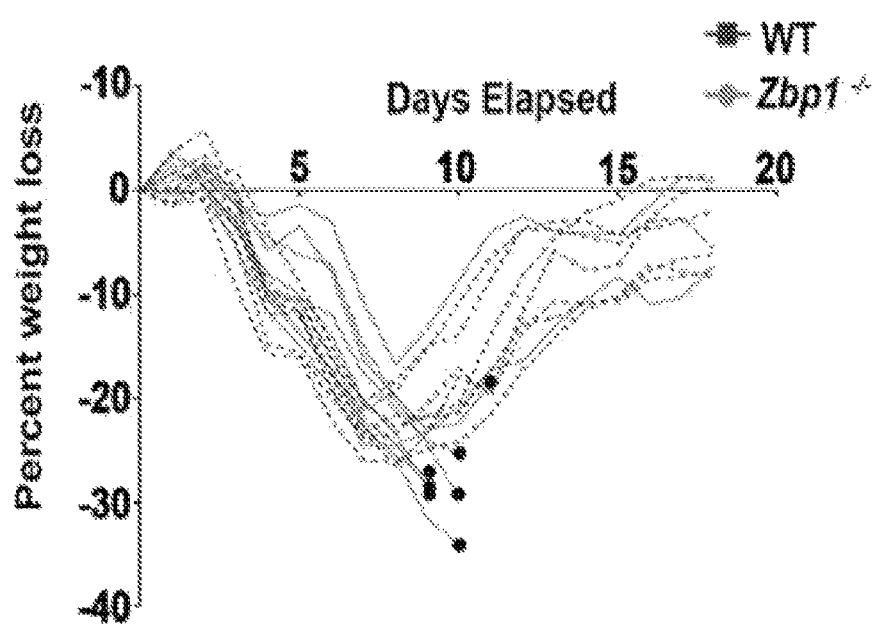

DAI is required for protection against IAV in vivo. To examine the role of DAI in host defense to IAV, zbp1$^{-/-}$ mice were infected with PR8 at a dose (1000 EID$_{50}$) that was not lethal to age- and sex-matched wild-type controls, and the survival of these mice was monitored over a time course of 18 days. All wild-type controls lost weight over the first week, but eventually recovered from infection by 15-18 dpi (see, FIGS. 15A and 15B). In contrast, ~80% of zbp1$^{-/-}$ mice perished between 9 and 12 dpi (see, FIGS. 15A and 15B).

Figure 15C:
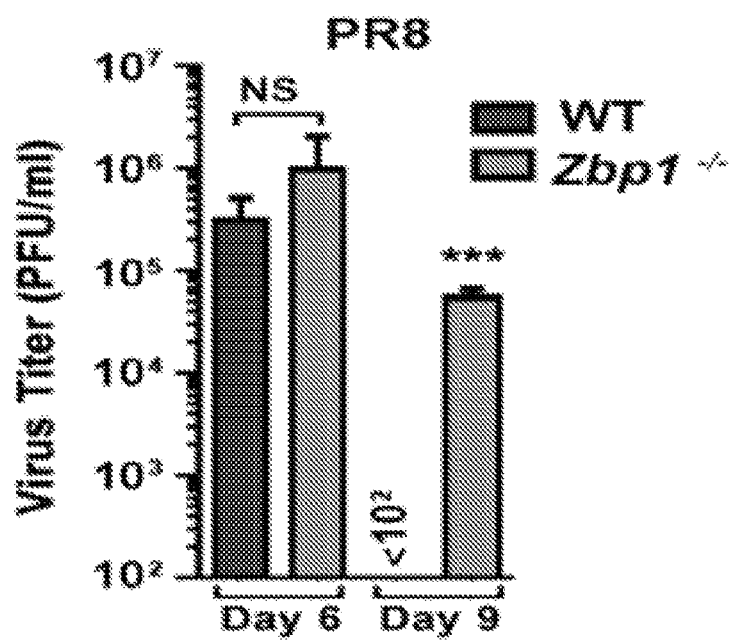
Figure 15D:
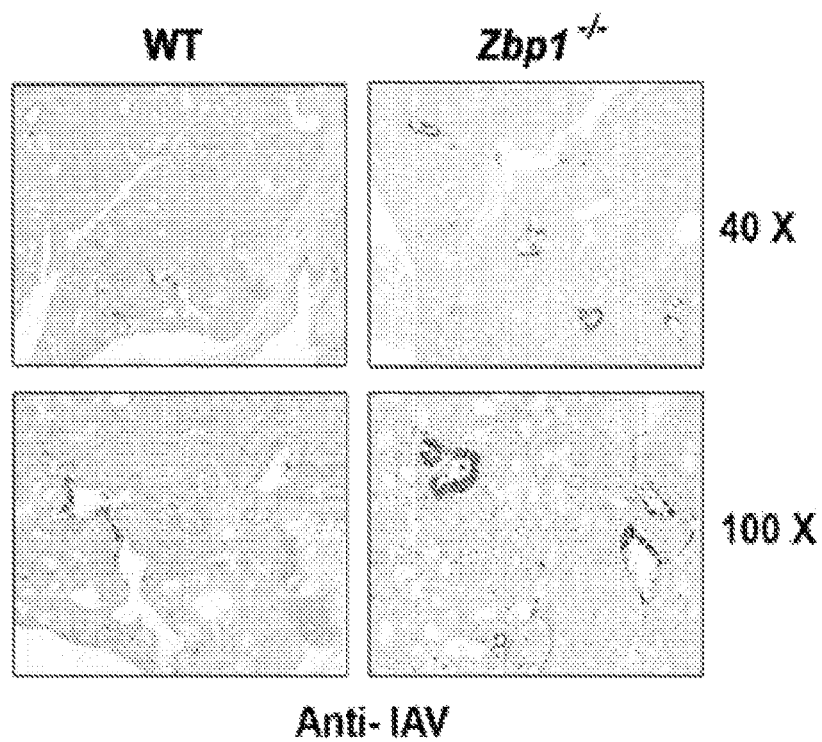

Next, virus replication was measured in lungs of mice infected with an even lower dose of PR8 (750 EID$_{50}$) to delay some the lethality associated with zbp1 loss. Progeny virion production was not notably different between lungs of wild type or zbp1$^{-/-}$ mice on day 6 p.i., but whereas virus was essentially cleared from wild-type lungs by 9 dpi, titers remained elevated in lungs from zbp1$^{-/-}$ animals (see, FIG. 15C). In agreement with these findings, numerous virus-positive bronchiolar epithelial cells were observed in zbp1$^{-/-}$ lungs 9 dpi, by which time wild type lungs had largely cleared virus, and only cellular debris in the lumens of certain airways remained virus antigen-positive (see, FIG. 15D). Moreover, hyaline membranes, indicative of diffuse severe alveolar damage in mice, were rarely seen in infected wild-type lungs 9 dpi, but were relatively common in zbp1$^{-/-}$ lungs (not shown). Without intending to be limited to any particular theory or mechanism of action, it is believed that these results signify that infected zbp1$^{-/-}$ bronchiolar epithelial cells have not undergone apoptosis or necroptosis and, thus, remain factories for virus production, greatly compromising lung function and resulting in mortality.

Figure 15E:
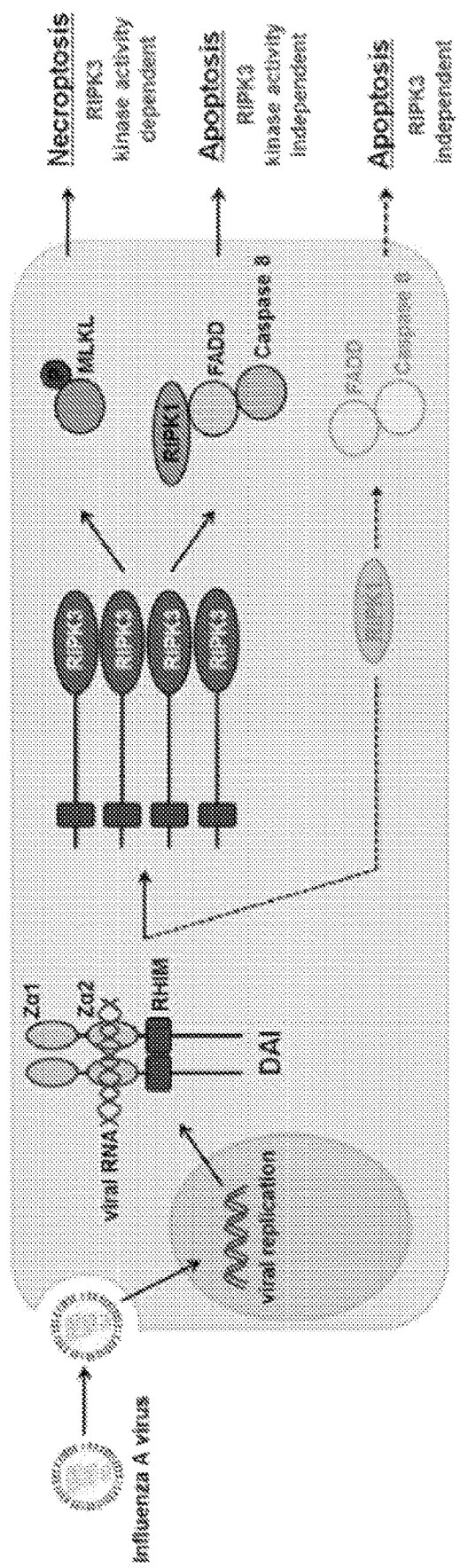

Example 5: Determination of DAI Sensitization of Influenza A Virus to Activate RIPK3-Dependent Cell Death: Summary Examples 3 and 4 provide evidence implicating DAI as the host sensor protein linking IAV replication to activation of RIPK3 and consequent induction of both necroptosis and apoptosis. A simple 'induced-proximity' model for how DAI senses IAV and stimulates RIPK3 is proposed (see, FIG. 15E). In this model, DAI recognizes RNA intermediates produced during the IAV life cycle, which induces the multimerization of DAI. This model is based, in part, on the published co-crystal structure of DAI Zα2 in complex with Z-DNA, which reveal dimers of Zα2 associating with a single dsDNA double helix. Crystallographic studies have found that Zα:Z-RNA complexes are conformationally very similar to Zα:Z-DNA complexes, and the in silico models based on these structures suggest that Zα2 domain of DAI associates with dsRNA as a dimer, bringing into proximity two or more molecules of DAI (see, FIG. 14E). Once juxtaposed, RHIM-based associations between DAI monomers allows further oligomerization of DAI, and recruitment and subsequent oligomerization of RIPK3 (see, FIG. 15E). Multimerization of DAI by IAV RNA may, at a minimum, suffice to recruit RIPK3, cluster this kinase, and initiate downstream death signaling (see, FIGS. 15A-15E). DAI also mediates RIPK3-independent cell death during IAV infection, via a FADD/caspase 8 axis. This pathway is at least partially dependent on RIPK1, suggesting that DAI may associate with RIPK1 to activate this alternative, delayed axis of RIPK3-independent cell death (see, FIG. 15E).

DAI appears to preferentially associate with shorter vRNAs, including internally-deleted variants of the polymerase gene segments previously identified as DI particle RNAs. Such subgenomic DI particle RNAs are produced when the IAV RNA dependent RNA polymerase (RdRp) falls off its antigenome template at the 5' end, but reattaches further downstream to continue transcription. These RNA segments are packaged in DI particles and retain the non-coding region, including the conserved 12 and 13 nucleotides at the 3' and 5' termini, respectively. The partial complementarity of these conserved nucleotides allows the formation of secondary 'corkscrew' structures that are recognized by the IAV RdRp. The profile of DAI-associated vRNA species bears similarity to vRNAs that associate with RIG-I during the course of IAV infection. It is believed that this suggests both DAI and RIG-I may recognize similar viral RNA species produced by IAV, with a propensity for subgenomic DI particle RNAs that may be improperly packaged and therefore more prone to detection by the host innate-immune machinery.

DAI also associates with some of the shorter IAV gene segments (most notably NA and NP) across their entire length, suggesting that dsRNA complexes of these genomic RNAs and their complementary antigenome templates serve as additional ligands for this sensor. The in silico models indicate that DAI Zα2 dimers are unlikely to make contacts with A-form dsRNA as they do with Z-RNA, so whether IAV dsRNAs that function as DAI ligands adopt the Z conformation, perhaps as a result of torsional stress induced by negative supercoiling during viral replication.

```
ZBP1 (DAI) cDNA (SEQ ID NO: 1):
agagctgcaa gaagcaccag gctcggccac ttcagaagcc ccagcctcga cctagcccacc ctctcaggg ccacagtgca gaagcctgca cacctgccaa gtctctccga ctccttgcagctgctgtcag catggcccag gctcctgctg acccgggcag agaaggccac cttgaacaaa gaatcctgca ggtgctgaca gaggctggct ccccggtgaa acttgcccag ctggtgaagg aatgccaagc acccaagagg gagctcaacc aagtcctcta ccgaatgaaa aaggagttga aagtctccct cacatcccct gccacctggt gcttgggcgg gactgatcct gaaggcgagg gtcctgcaga gctggccttg tccagccctg ccgagaggcc ccagcaacat gcagctacaa ttccagagac ccctggccct cagttcagcc aacaacggga ggaagacatc tacaggtttc tcaaagacaa tggtccccag agggccctgg tcatcgccca agcactggga atgaggacag caaaagatgt gaaccgagac ttgtacagga tgaagagcag gcaccttctg gacatggatg agcagtccaa agcatggacg atttaccgcc cagaagattc tggaagaaga gcaaagtcag cctcaattat ttaccagcac aatccaatca acatgatctg ccagaatgga cccaacagct ggatttccat tgcaaactcc gaagccatcc agattggaca cgggaacatc attacaagac agacagtctc cagggaggac ggttccgccg gtccacgcca cctcccttca atggcaccag gtgattcctc aacttggggg accctagttg atccctgggg gccccaggac atccacatgg agcagtccat actgagacgg gtgcagctgg acacagcaa tgagatgagg ctccacggcg tcccgtccga gggccctgcc cacatccccc ctggcagccc ccagtgttc cagtgcagtg ggaagcaggc agcagaggag agaggagctg aatcccagag gaagacactg acgtccagat cagccgggcg ggatcagtgg ggcagaccca ctgcgggatc agtggagcag aaagacgctt cccagacagc acaacgcac gagcggagtc tctgccactg ctgccggccc agaagcttcg tttgaagcaa gaattcccag tccaggaact caccctgagg gggaagccgc ccagagaatc cacatgaaat cgtgctttct cgaggacgcc accatcg RIPK3 cDNA SEQ ID NO: 2):
atgtcgtgcg tcaagttatg gcccagcggt gcccccgccc ccttggtgtc catcgaggaa ctggagaacc aggagctcgt cggcaaaggc gggttcggca cagtgttccg ggcgcaacat aggaagtggg gctacgatgt ggcggtcaag atcgtaaact caaaggcgat atccagggag gtcaaggcca tggcaagtct ggataacgaa ttcgtgctgc gcctagaagg ggttatcgag aaggtgaact gggaccaaga tcccaagccg gctctggtga ctaaattcat ggagaacggc tccttgtcgg ggctgctgca gtcccagtgc cctcggccct ggccgctcct ttgccgcctg ctgaaagaag tggtgcttgg gatgttttac ctgcacgacc agaacccggt gctcctgcac cgggacctca gccatccaa cgtcctgctg gacccagagc tgcacgtcaa gctggcagat tttggcctgt ccacatttca gggaggctca cagtcaggga cagggtccgg ggagccaggg ggcaccctgg gctacttggc cccagaactg tttgttaacg taaaccggaa ggcctccaca gccagtgacg tctacagctt cgggatccta atgtgggcag tgcttgctgg aagagaagtt gagttgccaa ccgaaccatc actcgtgtac gaagcagtgt gcaacaggca gaaccggcct tcattggctg agctgcccca agccgggcct gagactcccg gcttagaagg actgaaggag ctaatgcagc tctgctggag cagtgagccc aaggacagac cctccttcca ggaatgccta ccaaaaactg atgaagtctt ccagatggtg gagaacaata tgaatgctgc tgtctccacg gtaaaggatt tcctgtctca gctcaggagc agcaatagga gattttctat cccagagtca ggccaaggag ggacagaaat ggatggcttt aggagaacca gaaaaacca gcactctcgt aatgatgtca tggtttctga gtggctaaac aaactgaatc tagaggagcc tcccagctct gttcctaaaa aatgcccgag ccttaccaag aggagcaggg cacaagagga gcaggttcca caagcctgga cagcaggcac atcttcagat tcgatggccc aacctcccca gactccagag acctcaactt tcagaaacca gatgcccagc cctacctcaa ctgaacacc aagtcctgga ccccgaggga atcaggggc tgagagacaa ggcatgaact ggtcctgcag gaccccggag ccaaatccag taacagggcg accgctcgtt aacatataca actgctctgg ggtgcaagtt ggagacaaca actacttgac tatgcaacag acaactgcct tgcccacatg gggcttggca ccttcgggca aggggagggg cttgcagcac cccccaccag taggttcgca agaaggccct aaagatcctg aagcctggag
```

-continued

MLKL cDNA (SEQ ID NO: 3):
atccagcaca gagaagcaaa caccagaagc ttctctccaa ctttcagttt ttctctaaac ttccagtcct tctcatactg tgtcctggtt
ataatagttg ctgggacctt attctattct gaatcccag cccctaaaga aggcttggta ctgacgtgta cagcgtagtt acccagtgac
tttggggaag gcaggaagag tgtgaaaggg acaggaggaa ggaagggagg ggccgtggct ccgagctgcc tagaaagcgg
ctccagggag ccagggcacc gtgagcctgg tggttggcag ctggagccac gtcggagggg gaagtgtcgc agcattctct
gcaggcatca cagacctgag gcagtggcct ccggagggca ctggacagaa acagccatcc aagtggctga gtggagggac
cctgctcaag tgcagctgca gtggccgggg tttccctcag gtagggatcg gggcgccttg tcgccgccag ccacgtgtgg
cgtccggtac agtcagcaga gtgcaggtg cgggcaccag gaaaggggc gcaggggaac tcccgcgggc ctcgcgtttg
caaacttctc gcctgggcag gaggcggtcg tgggaaagaa ggtggaagag cgagcttttt ggaactgtgc acgggacaga
ttggacgcac acccctcggg aggcgcgaag gcatggaaaa tttgaagcat attatcaccc ttgccaggt catccacaaa
cggtgtgaag agatgaaata ctgcaagaaa cagtgccggc gcctgggcca ccgcgtcctc ggcctgatca gcctctgga
gatgctccag gaccaaggaa agaggagcgt gccctctgag aagttaacca cagccatgaa ccgcttcaag gctgccctgg
aggaggctaa tggggagata gaaaagttca gcaatagatc caatatctgc aggtttctaa cagcaagcca ggacaaaata
ctcttcaagg acgtgaacag gaagctgagt gatgtctgga aggagctctc gctgttactt caggttgagc aacgcatgcc
tgtttcaccc ataagccaag gagcgtcctg gcacaggaa gatcagcagg atgcagacga agacaggcga gctttccaga
tgctaagaag agataatgaa aaaatagaag cttcactgag acgattagaa atcaacatga agaaatcaa ggaaactttg
aggcagtatt taccaccaaa atgcatgcag gagatcccgc aagagcaaat caaggagatc aagaaggagc agctttcagg
atccccgtgg attctgctaa gggaaaatga agtcagcaca ctttataaag gagaatacca cagagctcca gtggccataa
aagtattcaa aaaactccag gctggcagca ttgcaatagt gaggcagact ttcaataagg agatcaaaac catgaagaaa
ttcgaatctc ccaacatcct gcgtatattt gggatttgca ttgatgaaac aggctacacc attcagaagc acctgaactc
cacggaaaaa tcagaagctc aaacttcctg gtaactcaag gctaccaagt gaagatttgg gtacctggct gagtttgggg
ctggcagcct tcagcacacc aatggtgtca atggcaggtg tgcatgggac aagaacatat gc ZBP1 (DAI) RNA (SEQ ID NO: 4):
agagcugcaa gaagcaccag gcucggccac uucagaagcc ccagccucga ccuagcccac ccucucaggg ccacagugca
gaagccugca caccugccaa gucucuccga cuccuugcag cugcugucag cauggcccag gcuccugcug cccgggcag
agaaggccac cuugaacaaa gaauccugca ggugcugaca gaggcuggcu ccccggugaa acuugcccag uggugaagg
aaugccaagc acccaagagg gagcucaacc aaguccucua ccgaaugaaa aaggaguuga aagucucccu cacaucccu
gccaccuggu gcuugggcgg gacugauccu gaaggcgagg guccugcaga gcuggccuug uccagcccug
ccgagaggcc ccagcaacau gcagcuacaa uuccagagac cccuggcccu caguucagcc aacaacggga ggaagacauc
uacagguuuc ucaaagacaa uggucccag aggggcccugg ucaucgccca agcacuggga augaggacag
caaaagaugu gaaccgagac uuguacagga ugaagagcag gcaccuucug gacauggaug agcaguccaa
agcauggacg auuuaccgcc cagaagauuc uggaagaaga gcaaagucag ccucaauuau uuaccagcac
aauccaauca acaugaucug ccagaaugga cccaacagcu ggauuuccau ugcaaacucc gaagccaucc agauuggaca
cgggaacauc auuacaagac agacagucuc cagggaggac gguuccgccg guccacgcca ccucccuuca
auggcaccag gugauuccuc aacuuggggg acccuaguug aucccugggg gcccaggac auccacaugg
agcaguccau acugagacgg gugcagcugg acacagcaa ugagaugagg cuccacgcg ucccguccga
gggcccugcc cacaucccc cuggcagccc cccagguuc cagugcagug ggaagcaggc agcagaggag
agaggagcug aauccccagag gaagcacacug acguccagau cagccgggcg ggaucagugg ggcagaccca
cugcgggauc aguggagcag aaagacgcuu cccagacagc acaacagcac gagcggaguc ucugccacug
cugccggccc agaagcuucg uuugaagcaa gaauucccag uccaggaacu cacccugagg gggaagccgc
ccagagaauc cacaugaaau cgugcuuucu cgaggacgcc accaucg -continued RIPK3 RNA (SEQ ID NO: 5):
augucgugcg ucaaguuaug gcccagcggu gcccccgccc ccuuggvguc caucgaggaa cuggagaacc
aggagcucgu cggcaaaggc ggguucggca caguguccg gcgcaacau aggaagugggg cuacgaugu
ggcggucaag aucguaaacu caaaggcgau auccagggag gucaaggcca uggcaagucu ggauaacgaa
uucgugcugc gccuagaagg gguuaucgag aaggugaacu gggaccaaga ucccaagccg cucuggugca
cuaaauucau ggagaacggc uccuugucgg ggcugcugca gucccagugc ccucggcccu ggccgcuccu
uugccgccug cugaaagaag uggugcuugg gauguuuuac cugcacgacc agaacccggu gcuccugcac
cgggaccuca agccauccaa cguccugcug acccagagc ugcacgucaa gcuggcagau uuuggccugu
ccacauuuca gggaggcuca cagucaggga caggguccgg ggagccaggg ggcacccugg gcuacuuggc
cccagaacug uuuguuaacg uaaaccggaa ggccuccaca gccagugacg ucuacagcuu cgggauccua
augugggcag ugcuugcugg aagagaaguu gaguugccaa ccgaaccauc acucguguac gaagcagugu
gcaacaggca gaaccggccu ucauuggcug agcugcccca agccggggccu gagacucccg gcuuagaagg
acugaaggag cuaaugcagc ucugcuggag cagugagccc aaggacagac ccuccuucca ggaaugccua
ccaaaaacug augaagucuu ccagaugguu gagaacaaua ugaaugcugc ugucuccacg guaaaggauu
uccugucuca gcucaggagc agcaauagga gauuucuau cccagaguca ggccaaggag ggacagaaau
ggauggcuu aggagaacca uagaaaacca gcacucucgu aaugaaguca ugguuucuga guggcuaaac
aaacugaauc uagaggagcc ucccagcucu guuccuaaaa aaugcccgag ccuuaccaag aggagcaggg
cacaagagga gcagguucca caagccugga cagcaggcac aucuucagau cgauggccc aaccuccca gacuccagag
accucaacuu ucagaaacca gaugcccagc ccuaccucaa cuggaacacc aagccugga ccccgaggga aucagggggc
ugagagacaa ggcaugaacu gguccugcag gaccccggag ccaaauccag uaacagggcg accgcucguu
aacauauaca acugcucugg ggucaaguu ggagacaaca acuacuugac uaugcaacag acaacugccu
ugcccacaug gggcuuggca ccuucgggca aggggagggg cuugcagcac cccccaccag uagguucgca
agaaggcccu aaagauccug aagccuggag caggccacag gguugguaua ucauagcgg gaaauaa
MLKL RNA (SEQ ID NO: 6):
auccagcaca gagaagcaaa caccagaagc uucucuccaa cuuucaguuu uucucuaaac uuccagcu
ucucauacug uguccugguu auaauaguug cugggaccuu auucuauucu gaaucccccag cccccuaaaga
aggcuuggua cugacgugua cagcguaguu acccagugac uuuggggaag gcaggaagag uguggaaagg
acaggaggaa ggaagggagg ggccguggcu ccgagcugcc uagaaagcgg cuccaggag ccagggcacc
gugagccugg ugguuggcag cuggagccac gucggaggg gaagugucgc agcauucucu gcaggcauca
cagaccugag gcaguggccu ccggagggca cuggacagaa acagccaucc aaguggcuga guggagggac
ccugcucaag ugcagcugca guggccgggg uuucccucag guagggaucg gggcgccuug ucgccgccag
ccacgugugg cguccgguac agucagcaga gugcaggugu cgggcaccag gaaaggggggc cagggggaac
ucccgcgggc cucgcguuug caaacuucuc gccugggcag gaggcggucg uggggaaagaa ggguggaagag
cgagcuuuuu ggaacugugc acgggacaga uuggacgcac accccucggg aggcgcgaag gcauggaaaa
uuugaagcau auuaucaccc uuggccaggu cauccacaaa cggugugaag agaugaaaua cugcaagaaa
cagugccggc gccugggcca ccgcguccuc ggccugauca agccucugga gaugcuccag gaccaaggaa
agaggagcgu gcccucugag aaguuaacca cagccaugaa ccgcuucaag gcugcccugg aggaggcuaa
uggggagaua gaaaaguuca gcaauagauc caauaucgc agguuucuaa cagcaagcca ggacaaaaua
cucuucaagg acgugaacag gaagcugagu gaugucugga aggagcucuc gcuguuacuu cagguugagc
aacgcaugcc uguucacccc auaagccaag gagcguccug ggcacaggaa gaucagcagg augcagacga
agacaggcga gcuuuccaga ugcuaagaag agauaaugaa aaaauagaag cuucacugag acgauuagaa aucaacauga aagaaaucaa ggaaacuuug aggcaguauu uaccaccaaa augcaugcag gagaucccgc aagagcaaau caaggagauc aagaaggagc agcuuucagg auccccgugg auucugcuaa gggaaaauga agucagcaca cuuuauaaag gagaauacca cagagcucca gugggccauaa aaguauucaa aaaacuccag gcuggcagca uugcaauagu gaggcagacu uucauuaagg agaucaaaac caugaagaaa uucgaaucuc ccaacauccu gcguauauuu gggauuugca uugaugaaac aggcuacacc auucagaagc accugaacuc cacggaaaaa ucagaagcuc aaacuuccug guaacucaag gcuaccaagu gaagauuugg guaccuggcu gaguuugggg cuggcagccu ucagcacacc aaugguguca auggcaggug ugcaugggac aagaacauau gc ZBP1 cDNA complement (DAI) (SEQ ID NO: 7):
tctcgacgtt cttcgtggtc cgagccggtg aagtcttcgg ggtcggagct ggatcgggtg ggagagtccc ggtgtcacgt cttcggacgt gtggacggtt cagagaggct gaggaacgtc gacgacagtc gtaccgggtc cgaggacgac tgggcccgtc tcttccggtg gaacttgttt cttaggacgt ccacgactgt ctccgaccga ggggccactt gaacgggtc gaccacttcc ttacggttcg tgggttctcc ctcgagttgg ttcaggagat ggcttacttt ttcctcaact ttcagaggga gtgtagggga cggtggacca cgaacccgcc ctgactagga cttccgctcc caggacgtct cgaccggaac aggtcgggac ggctctccgg ggtcgttgta cgtcgatgtt aaggtctctg gggaccggga gtcaagtcgg ttgttgccct ccttctgtag atgtccaaag agtttctgtt accagggtc tcccgggacc agtagcgggt tcgtgaccct tactcctgtc gttttctaca cttggctctg aacatgtcct acttctcgtc cgtggaagac ctgtacctac tcgtcaggtt tcgtacctgc taaatggcgg gtcttctaag accttcttct cgtttcagtc ggagttaata aatggtcgtg ttaggttagt tgtactagac ggtcttacct gggttgtcga cctaaaggta acgtttgagg cttcggtagg tctaacctgt gcccttgtag taatgttctg tctgtcagag gtccctcctg ccaaggcggc caggtgcggt ggagggaagt taccgtggtc cactaaggag ttgaaccccc tgggatcaac tagggacccc cggggtcctg taggtgtacc tcgtcaggta tgactctgcc cacgtcgacc ctgtgtcgtt actctactcc gaggtgccgc agggcaggct cccgggacg gtgtaggggg gaccgtcggg gggtcacaag gtcacgtcac ccttcgtccg tcgtctcctc tctcctcgac ttagggtctc cttctgtgac tgcaggtcta gtcggcccgc cctagtcacc ccgtctgggt gacgccctag tcacctcgtc tttctgcgaa gggtctgtcg tgttgtcgtg ctcgcctcag agacggtgac gacggccggg tcttcgaagc aaacttcgtt cttaagggtc aggtccttga gtgggactcc cccttcggcg ggtctcttag gtgtacttta gcacgaaaga gctcctgcgg tggtagc RIPK3 cDNA complement (SEQ ID NO: 8):
tacagcacgc agttcaatac cggggtcgcca cggggggcggg ggaaccacag gtagctcctt gacctcttgg tcctcgagca gccgtttccg cccaagccgt gtcacaaggc ccgcgttgta tccttcaccc cgatgctaca ccgccagttc tagcatttga gtttccgcta taggtccctc cagttccggt accgttcaga cctattgctt aagcacgacg cggatcttcc ccaatagctc ttccacttga ccctggttct agggttcggc cgagaccact gatttaagta cctcttgccg aggaacagcc ccgacgacgt cagggtcacg ggagccggga ccggcgagga aacgcggac gactttcttc accacgaacc ctacaaaatg gacgtgctgg tcttgggcca cgaggacgtg gccctggagt tcggtaggtt gcaggacgac ctgggtctcg acgtgcagtt cgaccgtcta aaaccggaca ggtgtaaagt ccctccgagt gtcagtccct gtcccaggcc cctcggtccc cgtgggaccc cgatgaaccg ggtcttgac aaacaattgc atttggcctt ccggaggtgt cggtcactgc agatgtcgaa gccctaggat tacacccgtc acgaacgacc ttctcttcaa ctcaacgttt ggcttggtag tgagcacatg cttcgtcaca cgttgtccgt cttggccgga agtaaccgac tcgacgggt tcggcccgga ctctgagggc cgaatcttcc tgacttcctc gattacgtcg agacgacctc gtcactcggg ttcctgtctg ggaggaaggt ccttacggat ggttttgac tacttcagaa ggtctaccac ctcttgttat acttacgacg acagaggtgc catttcctaa aggacagagt cgagtcctcg tcgttatcct ctaaaagata gggtctcagt ccggttcctc cctgtctta cctaccgaaa tcctcttggt atcttttggt cgtgagagca ttactacagt accaaagact caccgatttg tttgacttag atctcctcgg agggtcgaga caaggatttt ttacgggctc ggaatggttc tcctcgtccc gtgttctcct cgtccaaggt gttcggacct gtcgtccgtg tagaagtcta agctaccggg ttgagggggt ctgaggtctc tggagttgaa agtctttggt ctacgggtcg ggatggagtt gaccttgtgg ttcaggacct ggggctccct tagtccccg actctctgtt ccgtacttga ccaggacgtc ctgggcctc ggtttaggtc attgtcccgc tggcgagcaa ttgtatatgt tgacgagacc ccacgttcaa cctctgttgt tgatgaactg atacgttgtc tgttgacgga -continued acgggtgtac cccgaaccgt ggaagcccgt tccctcccc gaacgtcgtg ggggtggtc atccaagcgt tcttccggga tttctaggac ttcggacctc gtccggtgtc ccaaccatat tagtatcgcc ctttatt MLKL cDNA complement (SEQ ID NO: 9):
taggtcgtgt ctcttcgttt gtggtcttcg aagagaggtt gaaagtcaaa aagagatttg aaggtcagga agagtatgac acaggaccaa tattatcaac gaccctggaa taagataaga cttaggggtc ggggatttct tccgaaccat gactgcacat gtcgcatcaa tgggtcactg aaaccccttc cgtccttctc cacctttcc tgtcctcctt ccttccctcc ccggcaccga ggctcgacgg atctttcgcc gaggtccctc ggtcccgtgg cactcggacc accaaccgtc gacctcggtg cagcctcccc cttcacagcg tcgtaagaga cgtccgtagt gtctggactc cgtcaccgga ggcctcccgt gacctgtctt tgtcggtagg ttcaccgact caccctccctg gacgagttc acgtcgacgt caccggcccc aaagggagtc catccctagc cccgcggaac agcggcggtc ggtgcacacc gcaggccatg tcagtcgtct cacgtccac gcccgtggtc ctttccccg cgtcccttg agggcgcccg gagcgcaaac gtttgaagag cggaccgtc ctccgccagc acctttctt ccacttctc gctcgaaaaa ccttgacacg tgccctgtct aacctgcgtg tggggagccc tccgcgcttc cgtaccttt aaacttcgta taatagtggg aaccggtcca gtaggtgttt gccacacttc tctactttat gacgttcttt gtcacggccg cggacccggt ggcgcaggag ccggactagt tcggagacct ctacgaggtc ctggttcctt tctcctcgca cgggagactc ttcaattggt gtcggtactt ggcgaagttc cgacgggacc tcctccgatt accctctat ctttcaagt cgttatctag gttatagacg tccaaagatt gtcgttcggt cctgttttat gagaagttcc tgcacttgtc cttcgactca ctacagacct tcctcgagag cgacaatgaa gtccaactcg ttgcgtacgg acaaagtggg tattcggttc ctcgcaggac ccgtgtcctt ctagtcgtcc tacgtctgct tctgtccgct cgaaaggtct acgattcttc tctattactt ttttatcttc gaagtgactc tgctaatctt tagttgtact ttctttagtt cctttgaaac tccgtcataa atggtggttt tacgtacgtc ctctagggcg ttctcgttta gttcctctag ttcttcctcg tcgaaagtcc taggggcacc taagacgatt ccctttact tcagtcgtgt gaaatatttc ctcttatggt gtctcgaggt caccggtatt ttcataagtt ttttgaggtc cgaccgtcgt aacgttatca ctccgtctga aagttattcc tctagttttg gtacttcttt aagcttagag ggttgtagga cgcatataaa ccctaaacgt aactactttg tccgatgtgg taagtcttcg tggacttgag gtgccttttt agtcttcgag tttgaaggac cattgagttc cgatggttca cttctaaacc catgaccga ctcaaacccc gaccgtcgga agtcgtgtgg ttaccacagt taccgtccac acgtaccctg ttcttgtata cg ZBP1 (DAI) RNA complement (SEQ ID NO: 10):
ucucgacguu cuucguggu cgagccggug aagucuucgg ggucggagcu ggaucggguq ggagagucccc ggugucacgu cuucggacgu guggacgguu cagagaggcu gaggaacguc gacgacaguc guaccggguc cgaggacgac ugggcccguc ucuuccggug gaacuuguuu cuuaggacgu ccacgacugu uccgaccga ggggccacuu ugaacggguc gaccacuucc uuacgguucg uggguucucc cucgaguugg uucaggagau ggcuuacuuu uuccucaacu uucagaggga guguagggga cgguggacca cgaacccgcc cugacuagga cuuccgcucc caggacgucu cgaccggaac aggucgggac ggcucuccgg ggucguugua cgucgauguu aaggucucug gggaccggga gucaagucgg uuguugcccu ccuucuguag auguccaaag aguuucuguu accagggguc ucccgggacc aguagcgggu ucgugacccu uacuccuguc guuucuaca cuuggcucug aacauguccu acuucucguc cguggaagac cuguaccuac ucgucagguu ucguaccugc uaaauggcgg gucuucuaag accuucuucu cguuucaguc ggaguuaaua aauggucgug uuagguuagu uguacuagac ggucuuaccu ggguugucga ccuaaaggua acguuugagg cuucgguagg ucuaaccugu gcccuuguag uaauguucug ucugucagag gucccuccug ccaaggcggc caggugcggu ggagggaagu uaccgggguc cacuaaggag uugaacccccc uggggaucaac uagggacccc cggggguccug uaggguguacc ucgucaggua ugacucugcc cacgucgacc cuguguccguu acucuacucc gagguggccgc agggcaggcu cccgggacgg guguagggg gaccgucggg gggucacaag gucacgucac ccuucguccg ucgucuccuc ucuccucgac uuagggucuc cuucugugac ugcaggucua gucggcccgc ccuagucacc ccgcucggu gacgcccuag ucaccucguc uuucugcgaa gggucugucg uguugucgug cucgccucag agacggugac gacggccggg -continued ucuucgaagc aaacuucguu cuuaagggguc agguccuuga gugggacucc cccuucggcg ggucucuuag guguacuuua gcacgaaaga gcuccugcgg ugguagc RIPK3 RNA complement (SEQ ID NO: 11):
uacagcacgc aguucaauac cgggucgcca cgggggcggg ggaaccacag guagcuccuu gaccucuugg uccucgagca gccguuuccg cccaagccgu gucacaaggc ccgcguugua ccuucacccc cgaugcuaca ccgccaguuc uagcauuuga guuccgcua uagguccccuc caguuccggu accguucaga ccuauugcuu aagcacgacg cggaucuucc ccaauagcuc uuccacuuga cccugguucu aggguucggc cgagaccacu gauuuaagua ccucuugccg aggaacagcc ccgacgacgu cagggucacg ggagccggga ccggcgagga aacggcggac gacuuucuuc accacgaacc cuacaaaaug gacgugcugg cuuggggcca cgaggacgug gcccuggagu ucgguagguu gcaggacgac cuggguucucg acgugcaguu cgaccgucua aaaccggaca gguguaaagu cccuccgagu gucaguccccu gucccaggcc ccucggucccc ccgugggacc cgaugaaccg ggucuugac aaacaauugc auuggccuu ccggaggugu cggcacugc agaugucgaa gcccuaggau uacacccguc acgaacgacc uucucuucaa cucaacgguu ggcuugguag ugagcacaug cuucgucaca cguuguccgu cuuggccgga aguaaccgac ucgacgggu ucggcccgga cucugagggc cgaaucuucc ugacuuccuc gauuacgucg agacgacccu gucacucggg uuccugucug ggaggaaggu ccuuacggau gguuuuugac uacuucagaa ggcuaccac cucuuguuau acuuacgacg acagaggugc cauuuccuaa aggacagagu cgagucccucg ucguuauccu cuaaaagaua gggucucagu ccgguuccuc ccugucuuua ccuaccgaaa uccucuuggu aucuuuggu cgugagagca uuacuacagu accaaagacu caccgauuug uuugacuuag aucuccucgg agggucgaga caaggauuuu uuacgggcuc ggaauggguc uccucguccc guguucuccu cgccaagggu guucggaccu gucguccgug uagaagucua agcuaccggg uuggaggggu cugaggucuc uggaguugaa agucuuuggu cuacggggucg ggauggaguu gaccuugugg uucaggaccu ggggcucccu uaguccccccg acucucuguu ccguacuuga ccaggacguc cuggggccuc gguuuaggucc auugucccgc uggcgagcaa uuguauaugu ugacgagacc ccacguucaa ccucuguugu ugaugaacug auacguuguc uguugacgga acggguguac cccgaaccgu ggaagcccgu uccccucccc gaacgucgug ggggguggguc auccaagcgu ucuuccggga uuucuaggac uucggaccuc guccgguguc ccaaccauau uaguaucgcc cuuuauu MLKL RNA complement (SEQ ID NO: 12):
uaggucgugu cucuucguuu guggucuucg aagagagggu gaaagucaaa aagagauuug aaggucagga agaguaugac acaggaccaa uauuaucaac gaccccuggaa uaagauaaga cuuaggggguc gggggauuucu uccgaaccau gacugcacau gucgcaucaa ugggucacug aaaccccuuc cgucccuuucu cacccuuuccc uguccuccuu ccuucccucc ccggcaccga ggcucgacgg aucuuucgcc gagguccccuc gguccccgugg cacucggacc accaaccguc gaccucggug cagccucccc cuucacagcg ucguaagaga cguccguagu gucuggacuc cgucaccgga ggccucccgu gaccugucuu ugucgguagg uucaccgacu caccucccug ggacgaguuc acgucgacgu caccggcccc aaagggaguc cauccccuagc cccgcgaaac agcggcgguc ggugcacacc gcaggccaug ucagcgucu cacgucccac gcccgugguc cuuuccccccg cguccccuug agggcgcccg gagcgcaaac guuugaagag cggacccguc uccgccagc accccuuucuu ccaccuucuc gcucgaaaaa ccuugacacg ugcccugucu aaccugcgug uggggagccc uccgcgcuuc cguaccuuuu aaacuucgua uaauaguggg aaccggucca guaggugguu gccacacuuc ucuacuuuau gacguucuuu gucacggccg cggacccggu ggcgcaggag ccggacuagu ucgagaccu cuacgaguc cugguuccuu ucccucgca cgggagacuc uucaauuggu gucgguacuu ggcgaaguuc gacgggaccc uccuccgauu acccccucuau cuuuucaagu cguuaucag guuuaugacg uccaaagauu gucguucggu ccuguuuuau gagaaguucc ugcacuuguc cuucgacuca cuacagaccu uccucgagag cgacaaugaa guccaacucg -continued

```
uugcguacgg acaaaguggg uauucgguuc cucgcaggac ccguguccuu cuagucgucc uacgucugcu
ucugccgcu cgaaaggucu acgauucuuc ucuauuacuu uuuuaucuuc gaagugacuc ugcuaaucuu
uaguuguacu uucuuuaguu ccuuugaaac uccgucauaa auggugguuu uacguacguc cucuagggcg
uucucguuua guuccucuag uucuuccucg ucgaaaguac uagggggcacc uaagacgauu cccuuuuacu
ucagucugu gaaauauuuc cucuuauggu gucucgaggu caccgguauu uucauaaguu uuugaagguc
cgaccgucgu aacguuauca cuccgucuga aaguuauucc ucuaguuuug guacuucuuu aagcuuagag
gguuguagga cgcauauaaa cccuaaacgu aacuacuuug uccgaugugg uaagucuucg uggacuugag
gugccuuuuu agucucgag uuugaaggac cauugaguuc cgaugguuca cuucuaaacc cauggaccga
cucaaaccccc gaccgucgga agucgugugg uuaccacagu uaccguccac acguacccug uucuuguaua cg
```

ZBP1 (DAI) Protein (SEQ ID NO: 13):
MAQAPADPGR EGHLEQRILQ VLTEAGSPVK LAQLVKECQA PKRELNQVLY
RMKKELKVSL TSPATWCLGG TDPEGEGPAE LALSSPAKRP QQHAATIPET
PGPQFSQQRE EDIYRFLKDN GPQRALVIAQ ALGMRTAKDV NRDLYRMKSR
HLLDMDEQSK AWTIYRPEDS GRRAKSASII YQHNPINMIC QNGPNSWISI
ANSEAIQIGH GNIITRQTVS REDGSAGPRH LPSMAPGDSS TWGTLVDPWG
PQDIHMERSI LRRVQLGHSN EMRLHGVPSE GPAHIPPGSP PVSATAAGPE
ASFEARIPSP GTHPEGEAAQ RIHMKSCFLE DATIGNSNKM SISPGVAGPG
GVAGSGEGEP GEDAGRRPAD TQSRSHFPRD IGQPITPSHS KLTPKLETMT
LGNRSHKAAE GSHYVDEASH EGSWWGGGI RIPK3 Protein (SEQ ID NO: 14):
MSCVKLWPSG APAPLVSIEE LENQELVGKG GFGTVFRAQH RKWGYDVAVK
IVNSKAISRE VKAMASLDNE FVLRLEGVIE KVNWDQDPKP ALVTKFMENG
SLSGLLQSQC PRPWPLLCRL LKEVVLGMFY LHDQNPVLLH RDLKPSNVLL
DPELHVKLAD FGLSTFQGGS QSGTGSGEPG GTLGYLAPEL FVNVNRKAST
ASDVYSFGIL MWAVLAGREV ELPTEPSLVY EAVCNRQNRP SLAELPQAGP
ETPGLEGLKE LMQLCWSSEP KDRPSFQECL PKTDEVFQMV ENNMNAAVST
VKDFLSQLRS SNRRFSIPES GQGGTEMDGF RRTIENQHSR NDVMVSEWLN
KLNLEEPPSS VPKKCPSLTK RSRAQEEQVP QAWTAGTSSD SMAQPPQTPE
TSTFRNQMPS PTSTGTPSPG PRGNQGAERQ GMNWSCRTPE PNPVTGRPLV
NIYNCSGVQV GDNNYLTMQQ TTALPTWGLA PSGKGRGLQH PPPVGSQEGP
KDPEAWSRPQ GWYNHSGK MLKL Protein (SEQ ID NO: 15):
MENLKHIITL GQVIHKRCEE MKYCKKQCRR LGHRVLGLIK PLEMLQDQGK
RSVPSEKLTT AMNRFKAALE EANGEIEKFS NRSNICRFLT ASQDKILFKD
VNRKLSDVWK ELSLLLQVEQ RMPVSPISQG ASWAQEDQQD ADEDRRAFQM
LRRDNEKIEA SLRRLEINMK EIKETLRQYL PPKCMQEIPQ EQIKEIKKEQ LSGSPWILLR
ENEVSTLYKG EYHRAPVAIK VFKKLQAGSI AIVRQTFNKE IKTMKKFESP NILRIFGICI
DETVTPPQFS IVMEYCELGT LRELLDREKD LTLGKRMVLV LGAARGLYRL
HHSEAPELHG KIRSSNFLVT QGYQVKLAGF ELRKTQTSMS LGTTREKTDR
VKSTAYLSPQ ELEDVFYQYD VKSEIYSFGI VLWEIATGDI PFQGCNSEKI
RKLVAVKRQQ EPLGEDCPSE LREIIDECRA HDPSVRPSVD EILKKLSTFS K

CRISPR 1 (SEQ ID NO: 16):

tctggagtcacacaagagtccct

CRISPR 2 (SEQ ID NO: 17):
gctcagtacatctacatggacaagtccttg

Universal genomic viral RNA (vRNA) primer (SEQ ID NO: 18):
agcaaaagcagg

Primer 1 (SEQ ID NO: 19):
atggaaagaataaaagaactaag

Primer 2 (SEQ ID NO: 20):
ctaattgatggccatccgaattc

Targeted sequence (SEQ ID NO: 21):
tgagaacgttctgctcctgc

The present disclosure is not limited to the embodiments described and exemplified above, but is capable of variation and modification within the scope of the appended claims.

---

What is claimed is:

1. An RNA virus vector comprising an RNA virus comprising a gene encoding the human DNA-dependent activator of interferon-regulatory factors (DAI) protein and a gene encoding the human receptor-interacting serine/threonine-protein kinase 3 (RIPK3) protein, wherein the RNA virus further comprises a gene encoding the human mixed lineage kinase domain-like (MLKL) protein.

2. The RNA virus vector according to claim 1, wherein the gene encoding the human MLKL protein comprises a nucleic acid sequence encoding the amino acid sequence of SEQ ID NO:15.

3. The RNA virus vector according to claim 1, wherein the gene encoding the human MLKL protein is RNA.

4. The RNA virus vector according to claim 1, wherein the gene encoding the human MLKL protein comprises the nucleic acid sequence of SEQ ID NO:3, SEQ ID NO:6, or the complement of SEQ ID NO:3 or SEQ ID NO:6.

5. An RNA virus vector comprising an RNA virus comprising a gene encoding the human DNA-dependent activator of interferon-regulatory factors (DAI) protein, wherein the gene encoding the human DAI protein comprises the nucleic acid sequence of SEQ ID NO:1, SEQ ID NO:4, or the complement of SEQ ID NO:1 or SEQ ID NO:4.

* * * * *